(12) United States Patent
Unuma et al.

(10) Patent No.: US 6,571,193 B1
(45) Date of Patent: May 27, 2003

(54) METHOD, APPARATUS AND SYSTEM FOR RECOGNIZING ACTIONS

(75) Inventors: Munetoshi Unuma, Hitachi (JP); Shiro Nonaka, Hitachianaka (JP); Shigeru Oho, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/688,195

(22) Filed: Oct. 16, 2000

Related U.S. Application Data

(63) Continuation of application No. 08/886,730, filed on Jul. 1, 1997, now abandoned.

(30) Foreign Application Priority Data

Jul. 3, 1996 (JP) .............................................. 8-173453

(51) Int. Cl.[7] .............................. H04B 7/05; A61B 5/00
(52) U.S. Cl. ..................... 702/141; 702/189; 340/853.2
(58) Field of Search ................................. 702/141, 188, 702/189; 345/115, 440, 420, 475, 473; 73/379.01; 340/323 R, 384.71, 665, 853.2; 455/427, 504

(56) References Cited

U.S. PATENT DOCUMENTS

| 5,267,154 A | 11/1993 | Takeuchi et al. ............ 345/419 |
| 5,483,630 A | 1/1996 | Unuma et al. .............. 345/473 |

FOREIGN PATENT DOCUMENTS

| JP | 7-96014 | 10/1995 |

OTHER PUBLICATIONS

K. Noro, "Ergonimics Illustrated", Nippon Kikaku Kyokai, Feb. 14, 1990, pp. 538–544.

M. Unuma et al, "Generation of Human Walking Motion with Emotion for Computer Animation", Academic Society of Electronic, Information and Communication Engineers, D–11, vol. J76–D–11, No. 8, Aug. 1993, pp. 1822–1831.

M. Unuma et al, "Fourier Principles for Emotion–Based Human Figure Animation", Computer Graphics Proceedings, pp. 91–96.

*Primary Examiner*—Kamini Shah
(74) *Attorney, Agent, or Firm*—Mattingly, Stanger & Malur, P.C.

(57) ABSTRACT

An object of the present invention is to provide a method, an apparatus and a system for automatically recognizing motions and actions of moving objects such as humans, animals and machines. Measuring instruments are attached to an object under observation to measure a status change entailing the object's motion or action and to issue a signal denoting the measurements. A characteristic quantity extraction unit extracts a characteristic quantity from the measurement signal received which represents the motion or action currently performed by the object under observation. A signal processing unit for motion/action recognition correlates the extracted characteristic quantity with reference data in a database containing previously acquired characteristic quantities of motions and actions. The motion or action represented by the characteristic quantity with the highest degree of correlation is recognized and output.

29 Claims, 45 Drawing Sheets

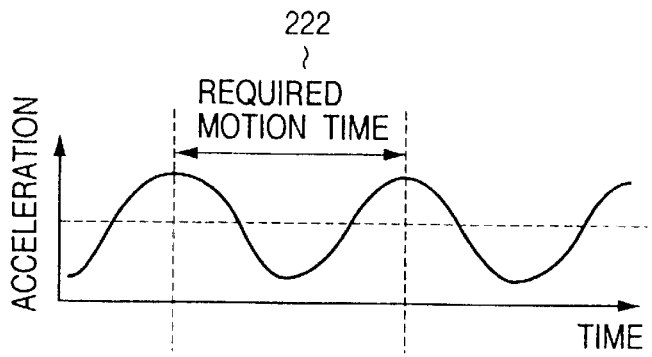
FIG. 5(a) OBSERVED WAVEFORM
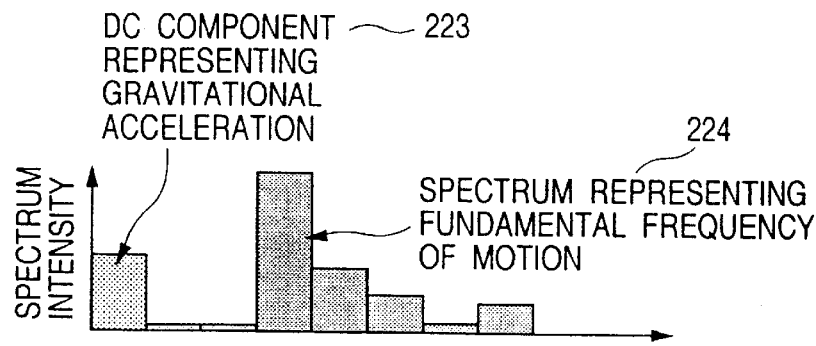
FIG. 5(b) TYPICAL RESULT OF HAVING OBSERVED WAVEFORM PARTITIONED BY WINDOW FUNCTION AND SUBJECTED TO SPECTRUM ANALYSIS
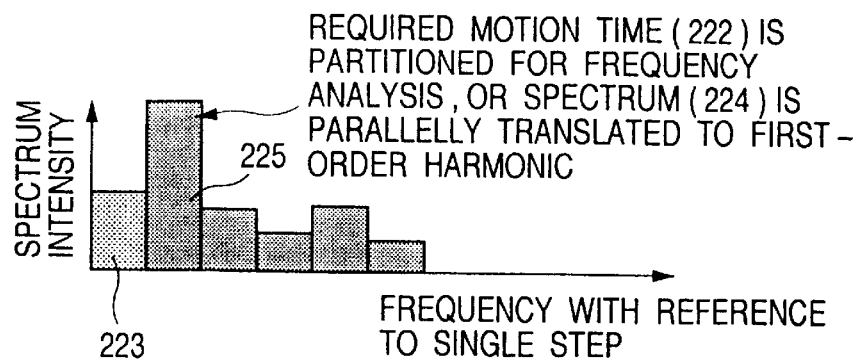
FIG. 5(c) CHARACTERISTIC QUANTITIES NORMALIZED BY USE OF MOTION TIME

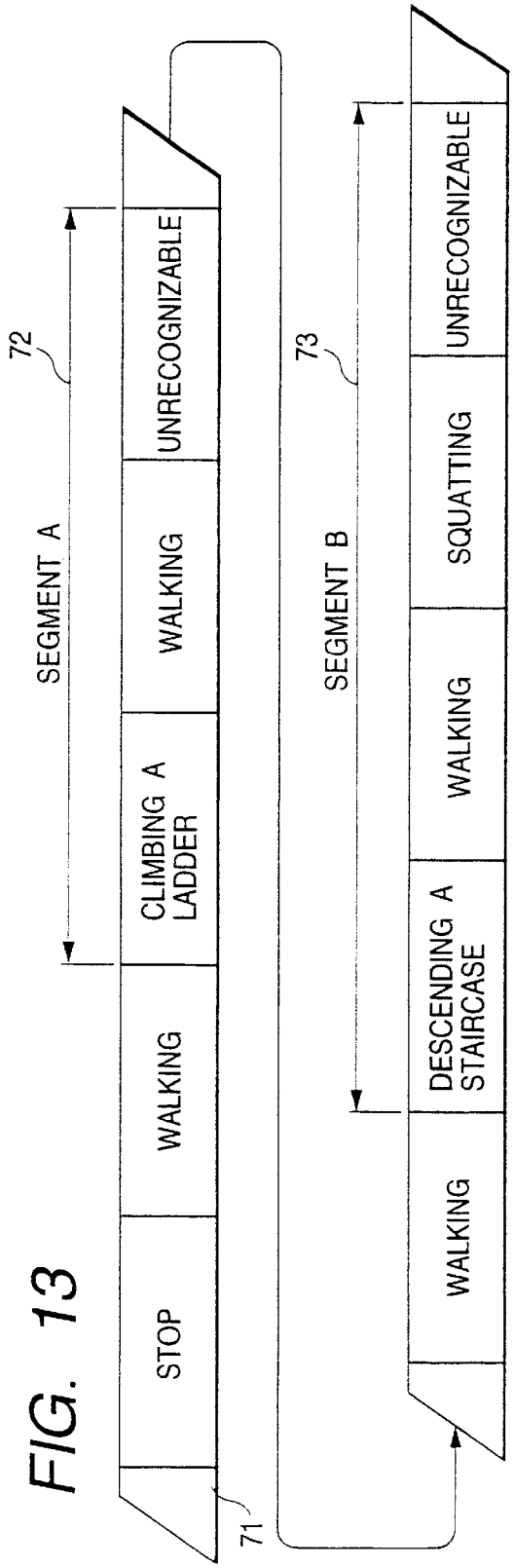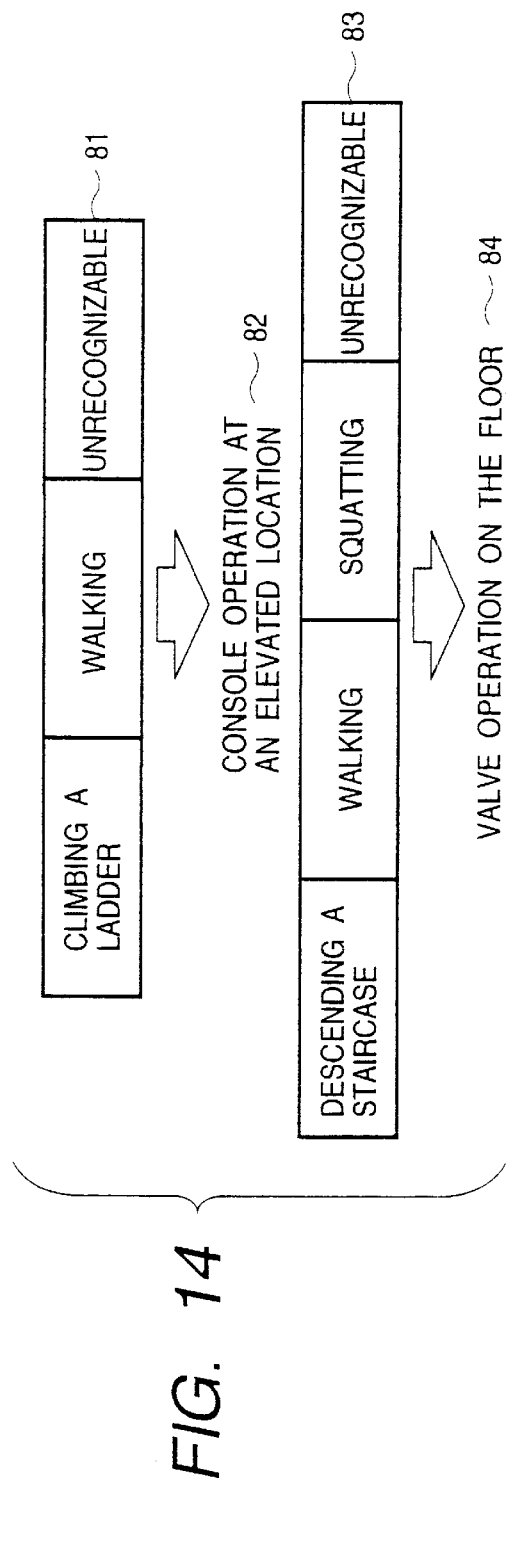
FIG. 13
FIG. 14

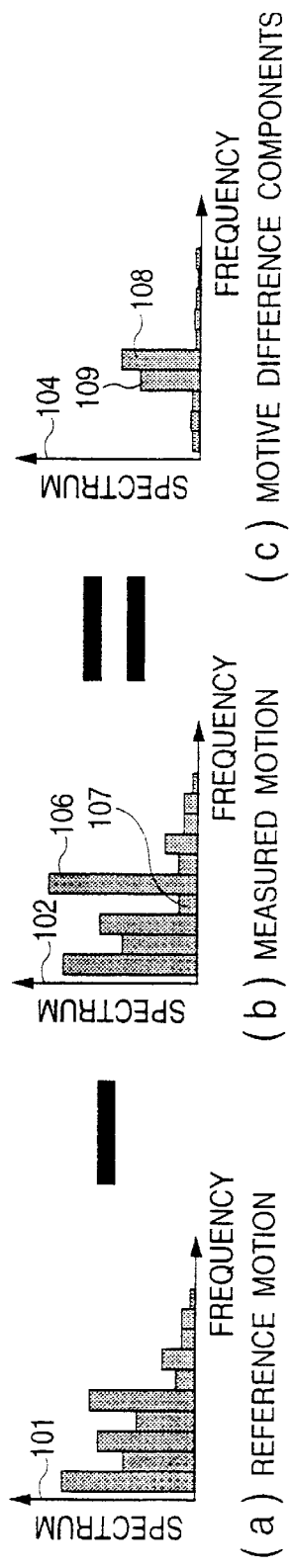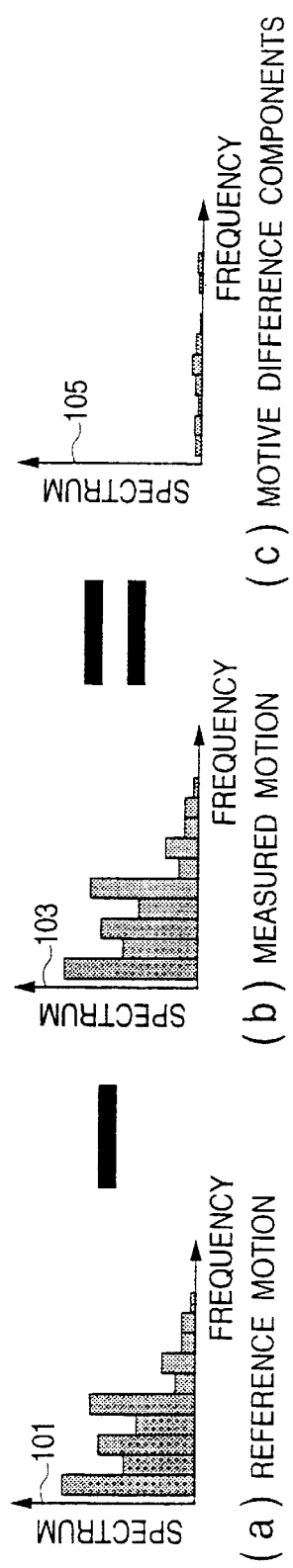

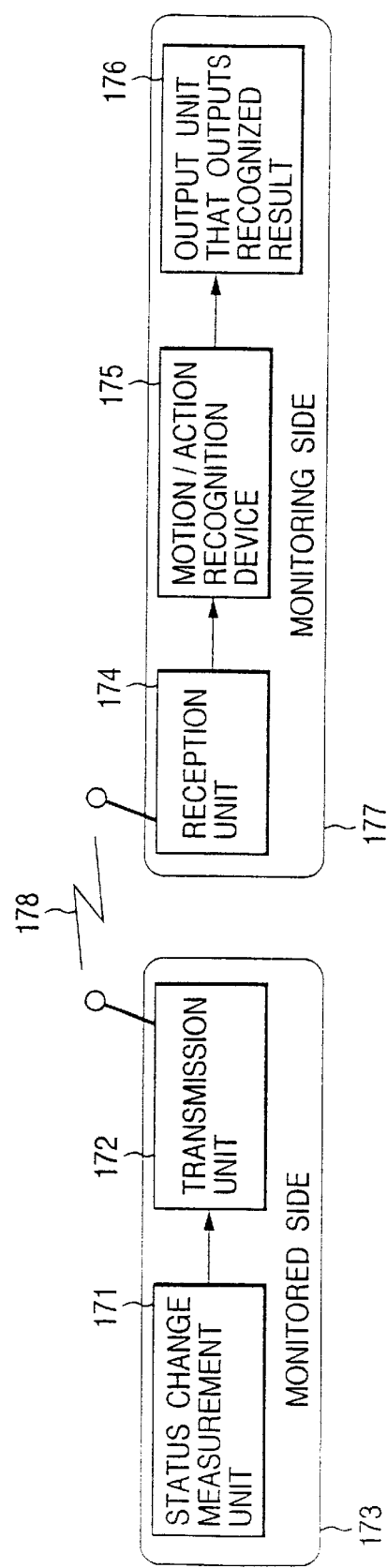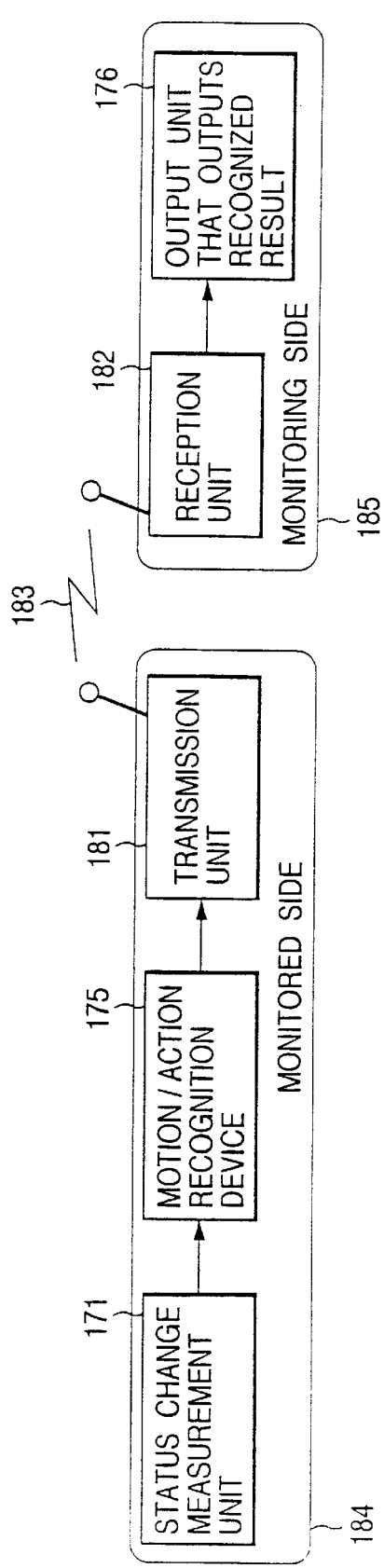

FIG. 42

| BRISKLY WALKING | BRISKLY WALKING | BRISKLY WALKING | WALKING |
|---|---|---|---|
| t : □□sec<br>x : ○○m<br>y : △△m<br>z : ××m | t : △□sec<br>x : ×○m<br>y : △□m<br>z : ××m | t : ×□sec<br>x : ○□m<br>y : ×△m<br>z : ××m | t : ○□sec<br>x : △○m<br>y : ◇△m<br>z : ×□m |

1124

| WALKING | WALKING | STANDING STILL | STANDING STILL |
|---|---|---|---|
| t : □△sec<br>x : △◎m<br>y : △○m<br>z : △×m | t : △△sec<br>x : ○□m<br>y : □△m<br>z : ×○m | t : ×△sec<br>x : ○○m<br>y : △△m<br>z : ××m | t : ○△sec<br>x : △△m<br>y : △△m<br>z : □□m |

1122, 1123

| COLLAPSING | LYING DOWN | LYING DOWN | LYING DOWN |
|---|---|---|---|
| t : □×sec<br>x : ××m<br>y : □○m<br>z : △×m | t : △×sec<br>x : ○○m<br>y : □□m<br>z : ××m | t : ××sec<br>x : ○○m<br>y : □□m<br>z : ××m | t : ○×sec<br>x : ○○m<br>y : □□m<br>z : ××m |

1125

SPECIFIC MOTION PATTERN — 1121

STANDARD WALKING
(WITH A GAIT CYCLE OF
ABOUT 1.0 SECOND)

LEISURELY WALKING
(WITH A GAIT CYCLE OF
ABOUT 1.5 SECONDS)

PRINCIPLE OF THE EXTRACTING METHOD

MEASURED WAVEFORM OF WALKING

MEASURED WAVEFORM OF RUNNING

METHOD, APPARATUS AND SYSTEM FOR RECOGNIZING ACTIONS

This is a continuation application of U.S. application Ser. No. 08/886,730, filed Jul. 1, 1997, now abandoned.

BACKGROUND OF THE INVENTION

1. Field of the Invention

The present invention relates to techniques for measuring a status change entailing motions and/or actions of a human being, an animal or a machine (generically called the object under observation hereunder). More particularly, the invention relates to a method for recognizing such motions and/or actions, as well as to an apparatus adopting that method and a system comprising that apparatus.

2. Description of Prior Art

The basic prior art pertaining to measuring human motions and work is described illustratively in "Ergonomics Illustrated" (by Kageo Noro, a Japanese publication from Nippon Kikaku Kyokai, Feb. 14, 1990, pp. 538–544). This publication discloses typical methods for measuring motions and work of humans through VTR-based observation or by direct visual observation.

Japanese Patent Publication No. Hei 7-96014 discloses a technique for using acceleration sensors to measure motions and the work of humans. This technique involves acquiring vibration waveforms from acceleration sensors attached to the human body as the latter performs each motion, subjecting the acquired vibration waveforms to analog-digital conversion, composing discrete A/D converted values thus obtained into a vibration pattern table, and comparing for judgment any A/D converted value resulting from an input vibration waveform with the vibration pattern table in synchronism with a timing signal output by a clock in appropriate timings. This technique permits recognition processing in the same motion or at the same speed as that in or at which the vibration pattern table is created.

The initially-mentioned conventional methods for measuring motions and work of humans through VTR-based or direct visual observation have the following major disadvantages:

(1) Analysis through VTR-based or direct visual observation requires the observer to continuously record positions of the object under observation and the work done thereby. It takes many hours and enormous effort for the observer to perform the task.

(2) Blind spots of the object under observation cannot be inspected through VTR-based or direct visual observation.

(3) If the object under observation is in motion, the observer must follow the object by moving likewise.

(4) The object under observation is liable to remain conscious of the VTR or of the eyes of the observer.

(5) In observing where the articulations of the object under observation are positioned, the conventional methods merely measure and reproduce the articulation positions; the methods do not allow actions or work of the object to be recognized automatically. It takes human observers to recognize the reproduced motions.

The conventional technique subsequently mentioned above has the following major disadvantages:

(6) Pitch differences are apt to occur between motions of walking and running. For example, a leisurely walk and a brisk walk fall within the same "walking" category but have different speed's entailing different lengths in the time base direction between the vibration pattern table and input vibration wave forms. This makes it impossible to detect correlations between the vibration waveform derived from the actual walk and the putatively corresponding vibration pattern table. The result is that motions of the same kind are erroneously recognized as two different motions. To recognize correctly the same kind of motions having different pitches requires additionally furnishing vibration pattern tables corresponding to different pitches. Furthermore, because pitches usually vary continuously, it takes many more vibration patterns to achieve more precise recognition. In short, to accomplish recognition of ever-higher precision requires a progressively large number of vibration pattern tables.

(7) Where a plurality of motions are to be recognized in combination, such as when the object is fanning himself while walking or when the object is walking inside a train in motion, it is necessary to establish a distinct vibration pattern for each of the combinations of motions (e.g., "fanning during walking," "walking inside a running train," etc.) In addition, where the object is, for example fanning himself while walking, it is also necessary to establish a vibration pattern for a case in which the fan is facing upward the moment the subject's foot contacts the ground, and another vibration pattern for a case where the fan is facing downward the moment the subject's foot touches the ground. In practice, viable recognition requires setting up a very large number of vibration pattern tables to address diverse instances of motions.

(8) The conventional technique measures only the acceleration applied to the human body and recognizes that parameter as data subject to recognition. This makes it difficult to recognize motions such as twisting or like motion of the body characterized by angular acceleration.

(9) The objective of recognition is limited to intermittent motions, whereas a human action is generally achieved as a combination of a plurality of motions. For example, the action of "sitting on a chair" is composed of motions "walking," "stopping" and "sitting" executed continuously in that order. The disclosed conventional technique has yet to address ways to recognize correctly the action made up of a plurality of motions.

SUMMARY OF THE INVENTION

An object of the present invention is to overcome the above and other deficiencies and disadvantages of the prior art and to provide a method for recognizing with more precision motions and actions of a moving object such as humans, animals and machines, as well as an apparatus adopting that method and a system comprising that apparatus.

A more specific object of the present invention is to provide a method, an apparatus and a system for recognition capable of achieving the following technical objectives:

(1) Motions, actions and work are automatically recognized so that the observer is free of undue operative burdens.

(2) Blind spots such as shadows of objects are eliminated.

(3) Observation will not be hampered or interrupted when the object under observation is in motion.

(4) The object under observation is free of burdens associated with conventional observation schemes.

(5) The object under observation is not merely measured for its motions, but also subjected to the recognition or estimation of its motions, actions and work on the basis of measured results.

(6) Measurements are not influenced by speeds of motions.

(7) A plurality of motions are recognized in combination.

(8) More kinds of motion than ever are recognized with reference to parameters other than acceleration.

(9) The object under observation (biological or mechanical) is not merely measured for its intermittent motions, but also subjected to the recognition or estimation of its motions, actions and work on the basis of a history of motions.

In carrying out the invention and according to one aspect thereof, there is provided a recognition apparatus for recognizing motions and actions of an object under observation, the recognition apparatus comprising: measurement means attached to the object under observation in order to measure a status change entailing the motions and actions of the object under observation; characteristic quantity extraction means for extracting characteristic quantities from the measurements taken by the measurement means; storage means for storing characteristic quantities of the motions and actions to be recognized by the recognition apparatus; recognition means for recognizing the motions and actions of the object under observation in accordance with the characteristic quantities extracted from the measurements and with the stored characteristic quantities; and output means for outputting a recognized result.

More specifically, a method, an apparatus and a system for recognition according to the invention illustratively comprise steps or means for performing the following:

(1) measuring instruments are attached to the object under observation. The instruments automatically take measurements of a status change entailing motions and actions of the object under observation. The measured data are transmitted to the observer.

(2) The status change of the object under observation is measured by use of an acceleration sensor, a velocity sensor or a position sensor free of visual or audio means.

(3) Observed results are transmitted by radio.

(4) Status changes are measured at a small number of observation points where these changes entailing motions and actions of the object under observation are pronounced.

(5) Characteristic quantities of typical motions or actions are extracted in advance. The predetermined characteristic quantities are compared in terms of correlation with characteristic quantities extracted from the measured data. From the comparison, a motion or an action represented by the characteristic quantities of high correlation is output as a recognized result.

(6) A previously measured waveform representing a single motion is normalized for duration from the time the motion is started until it ends. Normalization involves regarding the duration from start to end of a motion as "1." Illustratively, two steps of a walk constitute one cycle when normalized. Thereafter, characteristic components of each motion are extracted through functionalization, Fourier transformation or wavelet transformation. Coefficients used in the normalization or the extracted components from the transformation (Fourier, etc.) are established as characteristic quantities of the motions to be referenced. When the start and end of a motion are to be recognized from an input waveform derived from the motion, the waveform is normalized on the basis of the motion duration. Thereafter, coefficients or characteristic components are extracted through the above-mentioned functionalization or Fourier/wavelet transformation. The extracted coefficients or components are compared with the previously stored characteristic quantities for motion recognition.

(7) The characteristic quantities of different motions are superposed on each other. The result of the overlaying is recognized through observation. For example, the characteristic quantities of "walking" and those of "fanning oneself" are superposed on each other.

(8) For observation of motions and actions, not only acceleration data bus also other physical quantity data such as the velocity, position, angular acceleration, angular velocity, rotation angle and biological data entailing the motions and actions of the object under observation are acquired. The data thus obtained are used in the recognition process.

(9) Actions associated with a history of motions are previously established as associated motions. A history of observed and recognized motions is compared with the associated motions, whereby the actions of the object under observation are associated.

The steps or means outlined above accomplish illustratively the following effects when carried out or implemented:

(1) Measured data are automatically sent in, freeing the observer of operative chores conventionally associated with data gathering.

(2) The sensors used leave no blind spots.

(3) Because measurements are transmitted by radio, the object under observation may move about freely without the observer having to track him or her.

(4) A smaller number of observation points than in conventional setups reduce observation-related burdens on the object under observation. Without the observer watching the object, the latter is free from psychological constraints associated with the observer's glances.

(5) The automatic recognition process makes it unnecessary for the observer directly to handle raw data measured.

(6) The normalized time base permits motion recognition free of the influence by motion velocity.

(7) Because characteristic quantities are considered in combination, more complicated motions can also be recognized.

(8) Recognition is carried out through the use of not only acceleration but also other physical quantities. This makes it possible to recognize motions characterized only insignificantly by acceleration.

(9) An action made up of a plurality of motions (called work hereunder) is also recognized.

BRIEF DESCRIPTION OF THE DRAWINGS

FIG. 5A is a graphic representation of a waveform observed by the embodiment of FIG. 4;

FIG. 5B is a graphic representation of typical results of spectrum analysis applied to the data in FIG. 5A;

FIG. 5C is a graphic representation of typical results of spectrum analysis after normalization;

FIG. 13 is an explanatory view showing a typical history of motions or actions accumulated by the embodiment of FIG. 12;

FIG. 14 is an explanatory view of associative patterns used by the embodiment of FIG. 12;

FIG. 16A is an explanatory view showing an example of calculating the difference between a measured motion and a reference motion;

FIG. 16B is an explanatory view showing another example of calculating the difference between a measured motion and a reference motion;

FIG. 23 is a block diagram of a recognition device equipped with radio communication means to embody the invention;

FIG. 24 is a block diagram of another recognition device equipped with ratio communication means to embody the invention;

FIG. 42 is an example of the structure of data stored in a storage unit to represent the recognized motion, action and/or work of an object under observation as well as the position and the point of time at which the motion, the action and/or the work are recognized;

DETAILED DESCRIPTION OF THE PREFERRED EMBODIMENTS

Figure 1:
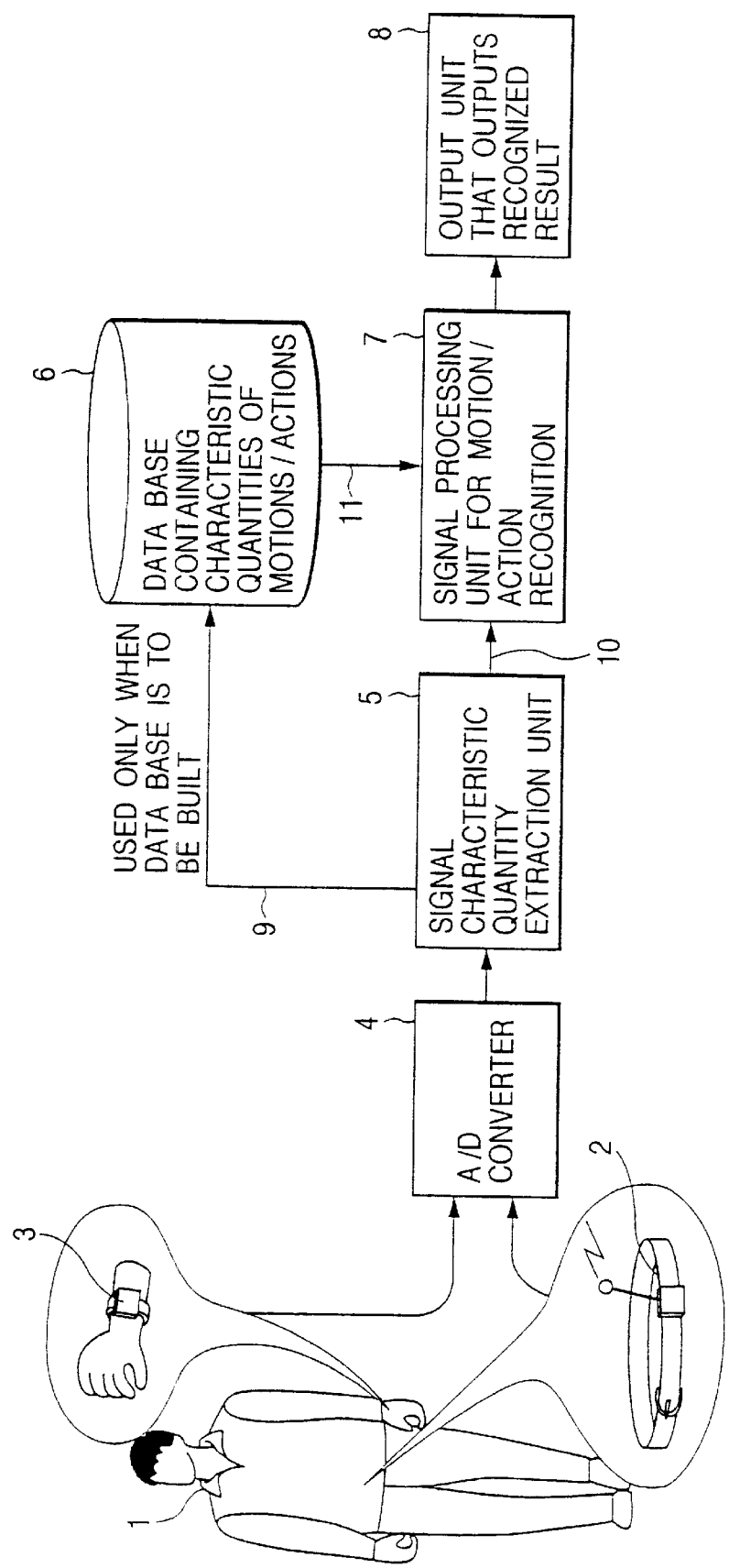
FIG. 1 is a block diagram of a motion and action recognition device practiced as one embodiment of the invention.

One preferred embodiment of the invention will now be described with reference to FIG. 1. With this embodiment, an object 1 under observation is assumed as the target to be recognized for its motions or actions (abbreviated to motions/actions hereunder where appropriate).

A recognition apparatus practiced as an embodiment of the invention for recognizing motions and actions comprises: measuring instruments 2 and 3 attached to the object 1 under observation; an A/D converter 4 for digitizing measured results from the measuring instruments 2 and 3; a characteristic quantity extraction unit 5 for extracting a characteristic quantity from the measured results digitized; a characteristic quantity database 6 for storing premeasured and preextracted characteristic quantities of various motions and actions; a signal processing unit 7 which, using data held in the characteristic quantity database 6, recognizes motions/actions represented by the characteristic quantity extracted by the characteristic quantity extraction unit 5; and an output unit 8 for outputting a recognized result.

The characteristic quantity extraction unit 5 and signal processing unit 7 are implemented illustratively by use of a memory and a data processor. The memory stores programs for executing a characteristic quantity extraction process and a motion/action recognition process, as will be described below. The data processor comprises a DSP or MPU for carrying out these programs. The output unit 8 is implemented by use o a display unit comprising an LCD panel or a CRT.

With this embodiment, the object 1 under observation is equipped with the measuring instruments 2 and 3 for measuring a status change entailing motions/actions of the object. The typical setup in FIG. 1 shows that the measuring instrument 2 is attached to the object's waist position while the instrument 3 is mounted on the object's arm for taking measurements of the status change. These measuring instruments are positioned where the readings of the status change are the most pronounced. For example, if the status change to be observed is likely to occur at the feet, the instruments may be attached to a foot or the feet. Either a single or a plurality of measuring instruments may be used.

The measurements taken by the status change measuring instruments 2 and 3 are converted continuously from analog to digital format by the A/D converter 4. After the analog-to-digital conversion, the digital signal reaches the characteristic quantity extraction unit 5 whereby the characteristic quantity specific to the signals is extracted. How the characteristic extraction process is performed will now be described with reference to FIG. 2.

Figure 2:
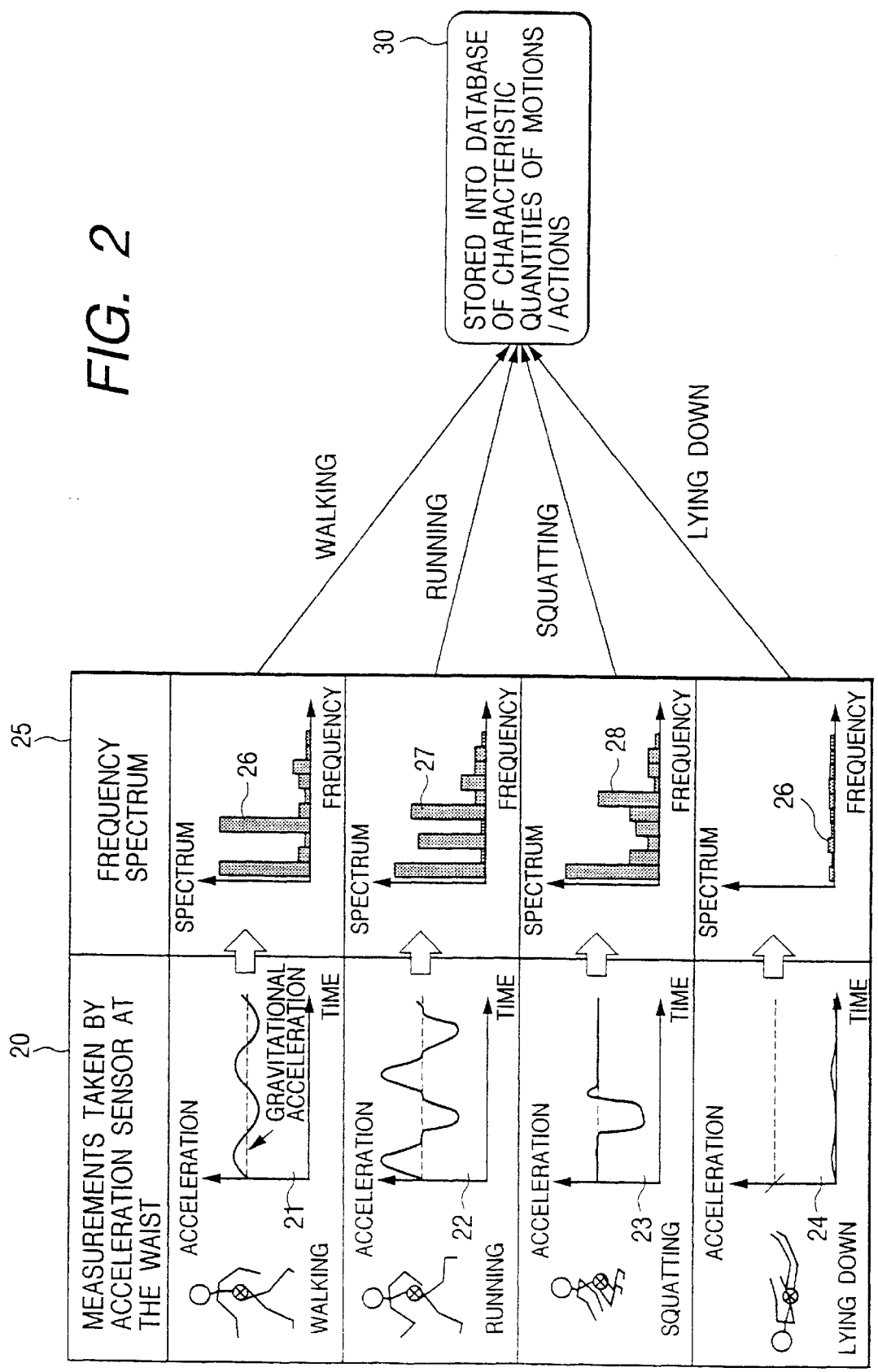
FIG. 2 is an explanatory view of typical outputs from an acceleration sensor attached to the waist of an object under observation.

A typical status change measuring instrument may be an acceleration sensor attached to the waist of the human body, as shown in FIG. 2. The acceleration sensor installed as depicted in FIG. 2 takes measurements of acceleration applied to the human body in the direction of its height. Output results 20 from the acceleration sensor indicate specific time series data items 21 through 24 derived from human motions of "walking," "running," "squatting" and "lying down." In the example of FIG. 2, data items 21 and 22 denote cyclic acceleration changes during walking or running, data item 23 represents a single acceleration change, and data item 24 stands for a state of no acceleration in which gravitational acceleration is not detected because the object is lying down.

After the above data items are digitized by the A/D converter 4, the digitized data are subjected to time-frequency analysis (e.g., Fourier transformation), which is a typical technique of signal analysis. The result is a frequency spectrum body 25. More specifically, the data items 21 through 24 are matched with frequency spectra 26, 27, 28 and 29 respectively. Bar graphs of the analyzed result represent spectrum intensities of the frequency components acquired through Fourier transformation. The frequency characteristic differs from one motion to another. The differences constitute the characteristic quantities of the motions involved.

With this embodiment, the characteristic quantities that serve as reference data used by the signal processing unit 7 for motion/action recognition are extracted and saved in advance from the motions and actions whose characteristic quantities are known. The reference data thus saved are stored into the characteristic quantity database 6 via a path 9 in FIG. 1 (process 30 in FIG. 2).

The signal processing unit 7 for motion/action recognition continuously receives characteristic quantity data 10 from the characteristic quantity extraction unit 5, the data 10 being derived from the ongoing motions/actions of the object 1 under observation. The data 10 are compared with the reference data 11 made up of the stored characteristic quantities of various motions/actions in the database 6. That is, the currently incoming characteristic quantity is correlated with the stored characteristic quantities in the database 6. At any point in time, the motion/action corresponding to the characteristic quantity having the highest level of correlation is judged to be the motion/action currently performed by the object 1 under observation. The judged result is output by the output unit 8.

Figure 29:
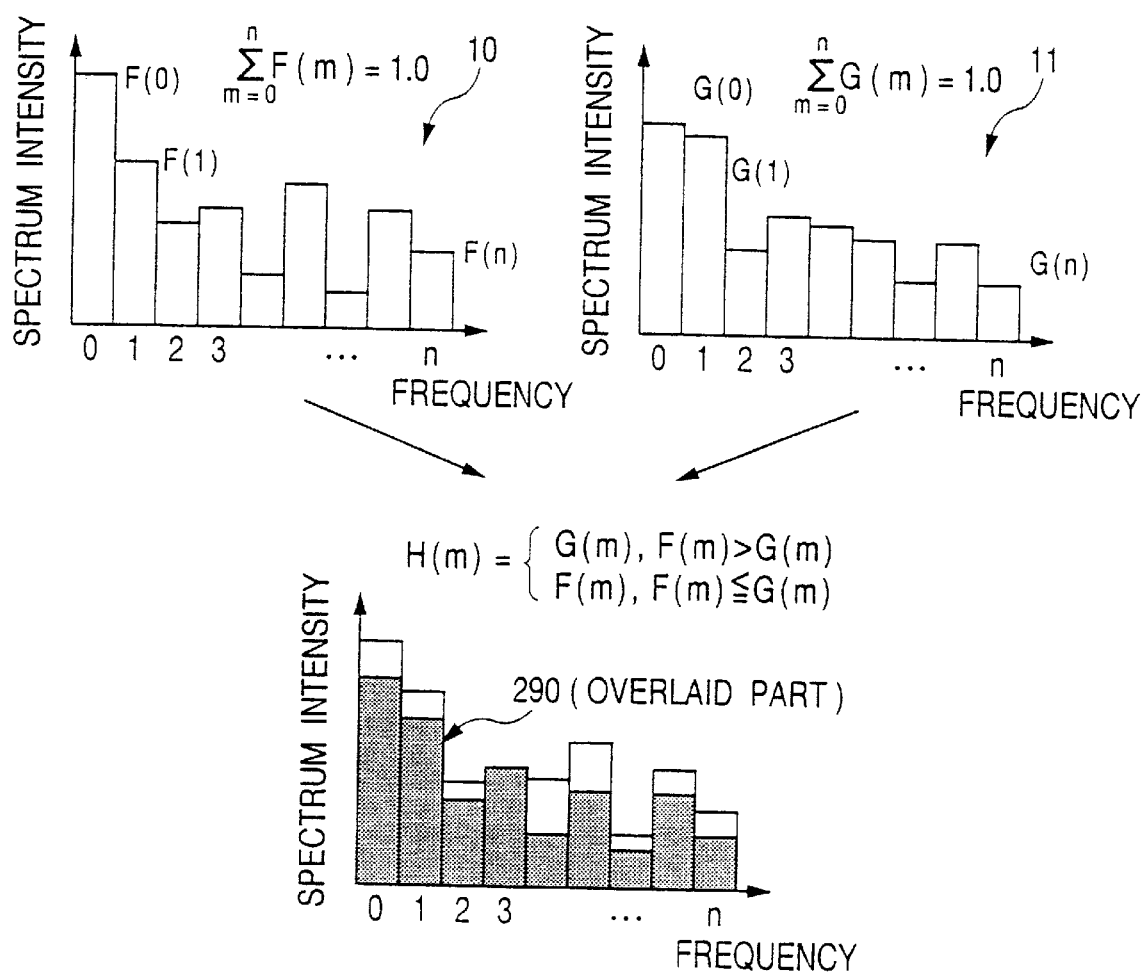
FIG. 29 is an explanatory view outlining one way of obtaining degrees of correlation between reference and measurements based on characteristic quantities acquired.

One way of correlating measurements with reference data is shown illustratively in FIG. 29, but is not limited thereto.

The scheme of FIG. 29 involves initially acquiring a frequency component F(m) which corresponds to characteristic quantity data 10 in the form of measured waveform spectra representing the motions/actions of the object 1 under observation, the data 10 being normalized so as to satisfy the expression (1) given below. Likewise, the scheme involves obtaining each frequency component G(m) which corresponds to the reference data 11 to be correlated and which is normalized so as to satisfy the expression (2) given below.

$$\sum_{m=0}^{n} F(m) = 1.0 \quad \text{(Expression 1)}$$

$$\sum_{m=0}^{n} G(m) = 1.0 \quad \text{(Expression 2)}$$

Next, a function H(m) is defined by use of the expression (3) given below as a function representing the correlation between the data 10 and 11.

$$H(m)=G(m):(\text{when } F(m)>G(m), \text{ or})=F(m):(\text{when } G(m) \leq F(m)) \quad \text{(Expression 3)}$$

The function H(m) indicates parts 290 in FIG. 29 where the two kinds of data overlay. If the function H(m) satisfies the expression (4) below, a correlation is judged to exist.

$$\sum_{m=0}^{n} H(m) \geq \alpha \quad \text{(Expression 4)}$$

where, H(m) has a maximum value of 1.0. Thus if the data to be correlated must be identical, then α=1.0. If the data need not be exactly identical to be correlated, then α is set to a value a little smaller than 1.0. Where a plurality of reference data items are compared for correlation, the maximum integral value of the function H(m) is regarded as representing the motion/action of the object 1 under observation, or as a candidate whose potential varies with the integral value.

In the expression (4) above, all frequency components of the spectra involved are set to have the same weight each. Alternatively, each of the components may have a different weight. For example, if any motion exhibits a specific spectrum, the corresponding component of the spectrum may be given a greater weight. Where there is noise, the component associated with the noise may be given a smaller weight. If β(m) is assumed to be a weight function specific to each frequency component m, the function H(m) representing correlation is defined as follows:

$$H(m)=G(m)\beta(m):(\text{when } F(m)>G(m), \text{ or})=F(m)\beta(m):(\text{when } G(m) \leq F(m)) \quad \text{(Expression 5)}$$

In this manner, the embodiment does not merely take status change measurements for use as measured values but subjects the measurements to recognition processing, whereby the motions/actions of the object under observation are recognized automatically.

With this embodiment, a small number of status change measuring instruments (at least one for this embodiment) are attached to the subject's body. These instruments transmit measurements that are subject to the process for recognizing the overall motion of the subject under observation. That is, a minimum of measuring instruments included in the embodiment make it possible to estimate a macroscopic motion of the object's whole body.

Furthermore, the embodiment requires only a limited number of measuring instruments to be mounted on the object's body. This eases considerably the physical burdens on the object under observation.

Transmission of the motion/action status of the object under observation from one place to another by the embodiment is characterized by the fact the recognized result need only be transmitted in each motion/action cycle. Unlike the conventional setup where measurements of the status change (i.e., measured values of each measurement cycle) are transmitted unchanged, the amount of data can be condensed for transmission.

With the above embodiment, the characteristic quantity extraction unit 5 adopts Fourier transformation it its frequency analysis. However, this analysis method is not limitative of the invention; wavelet transformation, time frequency analysis or any other appropriate frequency analysis scheme may be implemented, and the characteristic quantity may be extracted from the result of such transformation.

Figure 3:
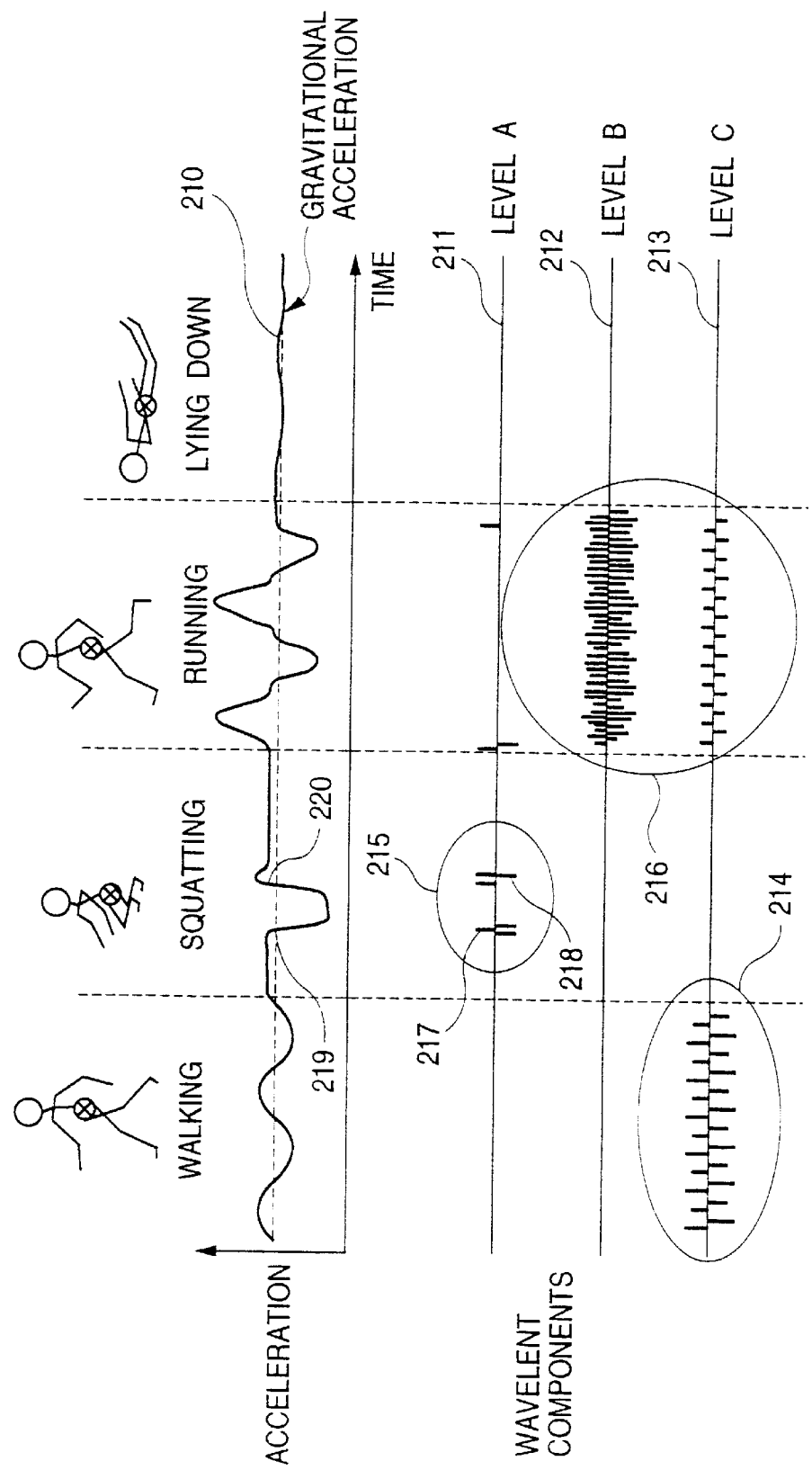
FIG. 3 is an explanatory view of typical results of time frequency analysis based on wavelet transformation.

How frequency analysis is carried out by use of wavelet transformation will now be described with reference to FIG. 3. In FIG. 3, reference numeral 210 represents acceleration changes measured from the object under observation shown moving in the upper part of the figure. The acquired waveform is subjected to wavelet transformation, from which characteristic values emerge in terms of levels (i.e., as wavelet components). For example, a motion of "walk" yields characteristic values 214 on level C (213). Likewise, a "squatting" motion produces characteristic values 215 on level A (211), and a "running" motion generates characteristic values 216 on levels B (212) and C (213). With this embodiment, these values represent quantities characteristic of the respective motions, and the characteristic quantities thus acquired allow motions/actions of the object to be recognized.

Where wavelet components are used as characteristic quantities, correlations between measurements and the reference data are acquired in the same manner as in the case where frequency components are used as characteristic quantities. In the latter case, the correlations of frequency components are obtained in terms of frequency component intensities, as opposed to the correlations of wavelet components that are acquired in terms of time-based intensities at each of various levels. In addition, correlations between levels are also obtained.

In connection with the embodiment, mention was made of the characteristic quantity obtained through the frequency analysis process based on digitized signals. However, that characteristic quantity is not limitative of the invention; any other forms of characteristic quantity may be used as long as the quantity can distinguish one motion or action from another. In an alternative setup, analog signals output by the measuring instruments 2 and 3 may be sent illustratively to a spectrum analyzer composed of a plurality of filter circuits. The spectrum analyzer extracts frequency characteristics from the received analog signals. The frequency components in the extracted analog values are regarded as the characteristic quantities to be compared by an along comparator with for frequency component. This setup also yields viable correlations. In another alternative, a function having a predetermined degree may be fitted to the output signal of a measuring instrument. In this case, combinations of coefficients included in the function may be used to represent characteristic quantities.

Whereas the embodiment utilizes correlations in its motion/action recognition process, motion/action recognition may be implemented alternatively by use of a neural network scheme replacing the correlation acquisition scheme. In such an alternative setup, the signal processing unit 7 for motion/action recognition is constituted by a neural network. When the database 6 storing characteristic quantities of motions/actions is to be built in the same setup, preextracted characteristic quantities denoting known motions/actions are stored as teacher signals into the neural network. Upon motion/action recognition, the characteristic quantity extraction unit 5 extracts a characteristic quantity from the acquired measurements and inputs the extracted quantity to the signal processing unit 7 composed of the neural network.

Whereas the above embodiment was shown using measurements taken on a single axis in the object's vertical direction for purpose of simplification and illustration, this is not limitative of the invention. Measurements taken in other directions, such as acceleration changes measured in the crosswise and lengthwise directions, may also be subjected to the process of characteristic quantity extraction. The extracted quantities may be judged and recognized individually or in combination.

In conjunction with the above embodiment, acceleration sensors were presented as a typical sensor for detecting changes in acceleration in the human body's height direction; the detected acceleration changes were subjected to characteristic quantity extraction. Alternatively, the same feature of acceleration detection may be implemented by use of a velocity or position sensor in place of the acceleration sensor. That is, acceleration changes are calculated (through linear or quadratic differential) on the basis of changes in velocity or position.

Whereas the above embodiment extracts characteristic quantities from acceleration changes, this is not limitative of the invention. Alternatively, a similar feature is implemented by extracting a characteristic quantity from velocity changes and by correlating the extracted quantity with the characteristic quantities which were preextracted from known velocity changes and stored in a database. If an acceleration sensor is used in the alternative case, quadratic differential is carried out to calculate the position; if a velocity sensor is used, linear differential is performed for position calculation.

With the above embodiment, the object under observation was assumed to be a human being. Alternatively, animals, articulated robots and other objects may also be subjected to the process of motion and action recognition.

Whereas the above embodiment was shown recognizing the entire movement of the object under observation such as walking and running, this is not limitative of the invention. Alternatively, a status change measuring instrument may be attached to a specific location of the object under observation. In this setup, which is basically the same as that of the embodiment above, measurements of the status change in that particular location are taken. A characteristic quantity is derived from the status change thus measured so that the movement or motions/actions of that specific location may be recognized.

For example, a status change measuring instrument mounted on a wrist watch may be used to extract a characteristic quantity from changes in the status of the wrist watch moving along with the object's arm. The extracted characteristic quantity is compared with reference characteristic quantities premeasured from known motions of the wrist watch moving with the arm. The comparison allows the wrist movement or motions/actions to be recognized. Similarly, a status change measuring instrument may be attached to the object's shoe or sock in order to recognize its movement or motions/actions. Alternatively, a measuring instrument mounted on a hat or eyeglasses permits recognition of the head's movement or motions/actions.

Whereas the above embodiment was shown addressing overall movements on the part of the human object in such activities as walking and running, this is not limitative of the invention. Alternatively, a status change measuring instrument may be attached not to the human object but to a device actuated by the human object, with the same setup of the embodiment still in use. In that case, changes in the status of the device actuated by the human object are measured. A characteristic quantity is extracted from the status changes thus measured, and is used to permit recognition of the motions or actions of the device in question.

For example, a pen, a pencil or an input device of a computer system (e.g., mouse) may be equipped with a status change measuring instrument. The instrument extracts a characteristic quantity from the measured changes in status of the implement in question. The extracted characteristic quantity may be compared illustratively with preestablished characteristic quantities derived from known letters or drawings as well as from known signatures. The comparison permits recognition of letters, drawings and/or signatures.

Described below with reference to FIGS. 4 and 5A, 5B and 5C is another embodiment of the invention whereby a varying velocity of the object in motion is recognized.

When humans or animals are in motion such as walking, the pace of the motion generally varies (slow walk, brisk walk, etc.) This means that the time required to accomplish each step in the case of walking varies. The time variation entails frequency change. It follows that measurements of a motion, when compared with preestablished characteristic quantities derived from known motions, may or may not be recognized correctly. The present embodiment is intended to solve this potential problem.

Figure 4:
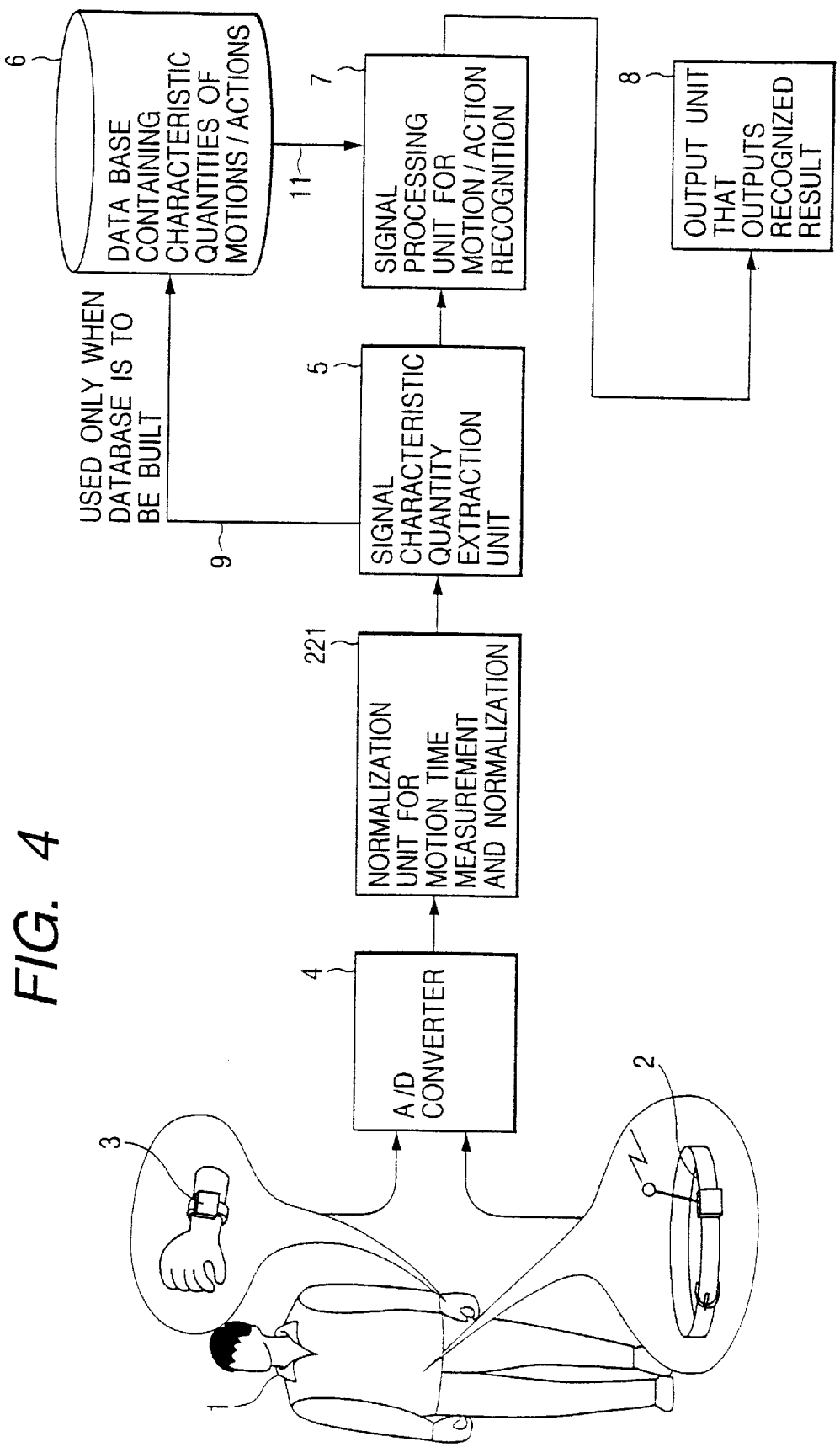
FIG. 4 is a block diagram of a recognition device practiced as another embodiment of the invention.

As shown in FIG. 4, a recognition apparatus embodying this invention has a normalization unit 221 additionally interposed between the A/D converter 4 and the characteristic quantity extraction unit 5 of the apparatus in FIG. 1. The normalization unit 221 takes measurements of the operation time to be measured, and performs normalization based on the measured operation time.

With the present embodiment, the required motion time denoting a cycle of the motion (e.g., walking) to be measured is defined as indicated by reference numeral 222 in FIG. 5A. An observed waveform is partitioned for frequency analysis by use of a window function having a time longer than that required for a single step. This provides a fundamental frequency spectrum 224 representing one step of walking, as depicted in FIG. 5B. In this context, a varying velocity of motion signifies that the spectrum 224 shifts crosswise.

With the present embodiment, the normalization unit 221 measures the time required of the motion in question after analog-to-digital signal conversion by the A/D converter 4. Specifically, if the motion is cyclic, the time required thereof is obtained from the above-mentioned fundamental frequency (i.e., required motion time 222). If the motion is not cyclic as in the case of squatting, the required operation time is obtained from the lengths of acceleration change edges 219 and 220 in FIG. 3 or from the distance between signals 217 and 218 (on level A in this example) in wavelet transformation.

Characteristic quantities are normalized by partitioning the observed waveform in units of the operation time required of the motion in question. The normalized result is subjected to frequency analysis, as shown FIG. 5C. This process is called time alignment which may also be implemented by use of a so-called time elastic function.

In the spectrum resulting from normalization, a fundamental frequency spectrum 225 of the motion appears in a first-order harmonic as shown in FIG. 5C. The spectrum 225 is obtained by parallelly translating harmonic components occurring subsequent to the spectrum 224 so that the spectrum 224 will turn into a first-order harmonic. The same effect may therefore be acquired if the spectrum of FIG. 5B is first obtained as a characteristic quantity and then corrected illustratively through parallel translation. As a result, the axis of abscissa in FIG. 5C represents frequencies with reference to a single step of walking.

The normalization process described above is carried out in two cases: when the database 6 storing characteristic quantities of known motions/actions is prepared, and when an observed waveform is recognized through the use of the reference data in the database 6.

With this embodiment, the signal processing unit 7 receives a characteristic quantity which is independent of operation time and which delimits each motion. This makes it possible to perform correct recognition of the movement free of the operation time involved. The measured operation time, when output, enables more detailed actions to be distinguished from one another, such as slow walk and brisk walk.

Figure 6:
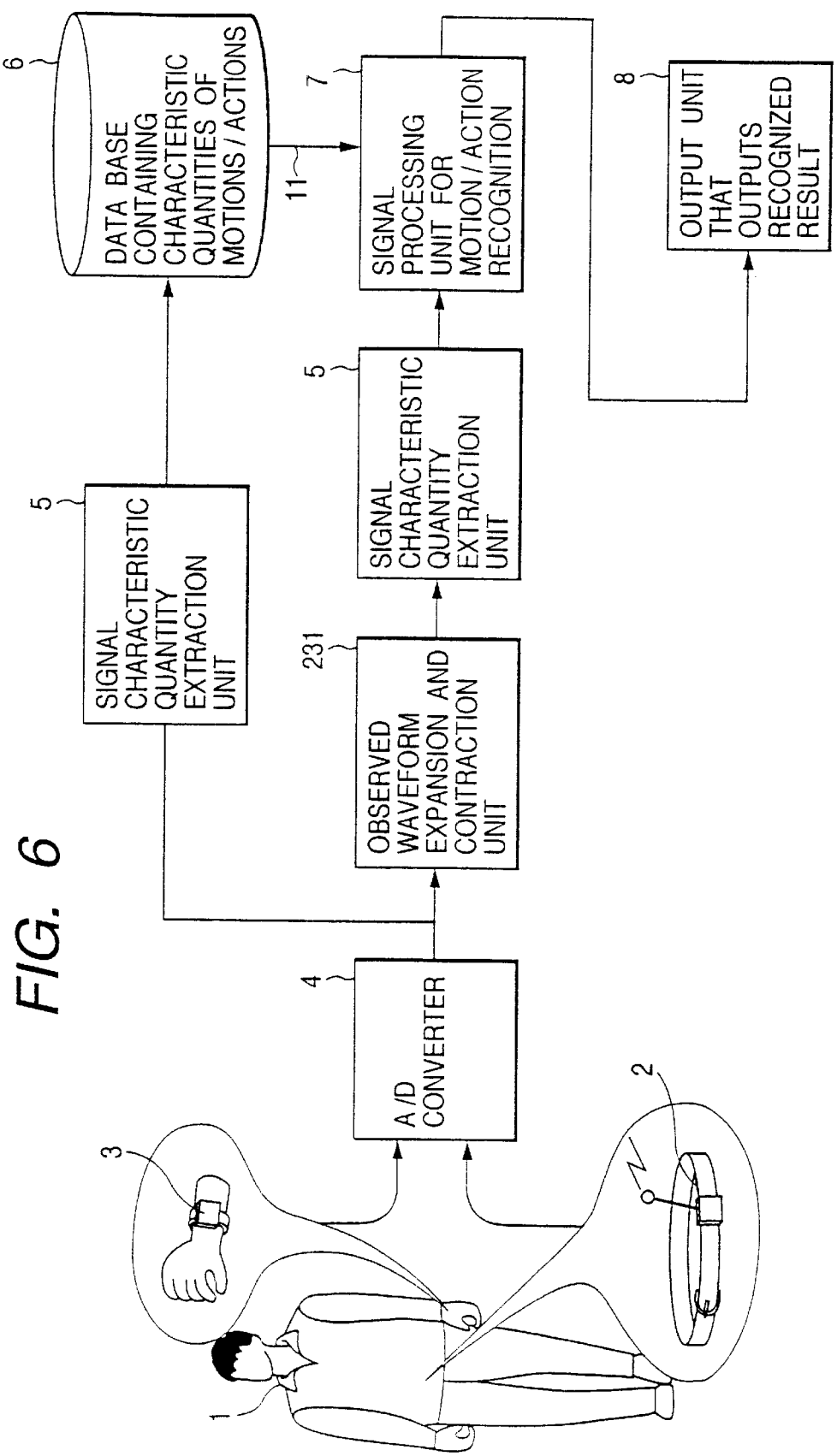
FIG. 6 is a block diagram of a recognition device practiced as another embodiment of the invention.

Described below with reference to FIG. 6 is another embodiment addressing applications where the velocity of motion is varied.

This embodiment is a recognition apparatus which, as shown in FIG. 6, has an expansion and contraction unit 231 interposed between the A/D converter 4 and the characteristic quantity extraction unit 5 as well as another characteristic quantity extraction unit 5 interposed between the A/D converter 4 and the characteristic quantity database 6 of the apparatus in FIG. 6. The expansion and contraction unit 231 extracts and contracts measured waveforms. The characteristic quantity database 6 is built in the same manner as with the embodiment of FIG. 1.

In the embodiment of FIG. 6, the expansion and contraction unit 231 is used to modify measured waveforms where it is feasible to recognize such waveforms. More specifically, the expansion and contraction unit 231 expands and contracts the time base of a measured waveform as needed. To expand the time base means prolonging the operation time of the motion in question; contracting the time base signifies shortening the operation time of the motion. The expansion and contraction process is performed by use of various predetermined expansion and contraction parameters. Thereafter, the characteristic quantity extraction unit 5 extracts a characteristic quantity from the result of the processing that used each of the parameters. The characteristic quantity thus extracted is sent to the signal processing unit 7 for recognition processing.

The signal processing unit 7 receives characteristic quantities representing a number of temporally expanded or contracted waveforms derived from the measured waveform. Of the received characteristic quantities, the quantity representing the motion with the highest degree of correlation is output as the recognized result. The expansion-contraction ratio that was in use is output at the same time. This makes it possible additionally to recognize a difference between the operation time of the motion in question and that of the corresponding motion held in the characteristic quantity database 6.

The embodiment of FIG. 6 offers the benefit of permitting correct recognition when the velocity of the target motion varies. Another benefit of this embodiment is its ability to recognize the operation time (i.e., velocity) of the motion in question.

Whereas the embodiment of FIG. 6 was shown expanding and contracting the time base of the observed waveform, this is not limitative of the invention. Alternatively, other characteristics of the observed waveform may be expanded and contracted for recognition purposes as long as the quantities characteristic of the motion to be recognized are not changed inordinately. Illustratively, the signal intensity of the observed waveform may be expanded and contracted for recognition processing. Upon successful recognition, the expansion-contraction ratio used in the process may be displayed at the same time.

Another embodiment of the invention is described below with reference to FIG. 7. This embodiment selects a plurality of characteristic quantities and composes them into a new characteristic quantity for recognition processing.

In the recognition process of the embodiments in FIGS. 1, 4 and 6, a correlation is recognized between one measured characteristic quantity and one preestablished characteristic quantity selected from those in the database. By contrast, the embodiment of FIG. 7 recognizes a plurality of characteristic quantities in combination.

When people walk, their behavior can be diverse; they may "wave their hand while walking," "walk in a moving train" or otherwise perform a combination of motions concurrently. With the preceding embodiments, each combination of concurrent motions (e.g., walking in a moving train) is collectively regarded as a single motion. In such cases, characteristic quantities of the motion as a whole need to be extracted and stored in the database 6 of motions/actions. However, in terms of motive frequency, the motion of "waving a hand while walking" may be regarded as a combination of "walking" and "waving" motions whose characteristic quantities are superposed on each other. Likewise, the motion of "walking in a moving train" may be considered a combination of "the movement of the train" and "walking" motions whose characteristic quantities are superposed on each other.

Figure 7:
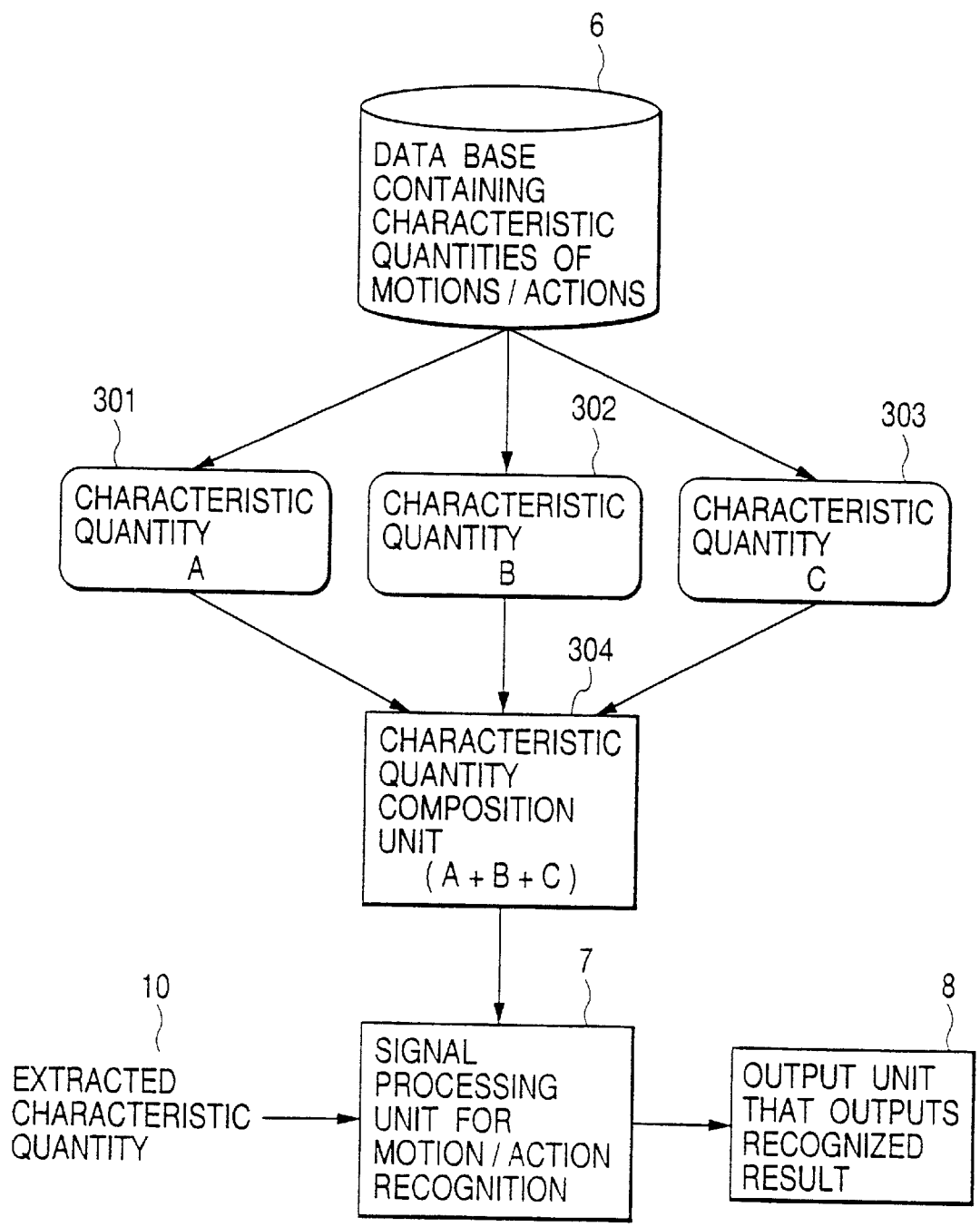
FIG. 7 is a block diagram of a recognition device practiced as another embodiment of the invention.

In the embodiment of FIG. 7. the motions with their characteristic quantities superposed on each other are processed for motion/action recognition as follows:

Initially, the embodiment selects characteristic quantities A (301 in FIG. 7), B (302) and C (303) to be superposed on each other in the recognition process. The three quantities A, B and C correspond to those of "walking," "waving" and "the movement of the train" in the preceding example.

The characteristic quantities A, B and C are then subjected to an overlaying process in a characteristic quantity composition unit 304. For example, where characteristic quantities are obtained through frequency analysis, the overlaying process involves overlaying one frequency spectrum upon another.

Finally, a new characteristic quantity (A+B+C) derived from the overlaying process is correlated with the characteristic quantity 10 corresponding to a measured signal extracted by the characteristic quantity extraction unit 5. The signal processing unit 7 performs a motion/action recognition process based on the result of the correlation. The recognized result is output by the output unit 8.

In the overlaying process above, the newly generated characteristic quantity Q is defined by the expression:

$$Q = A + B + C \qquad \text{(Expression 6)}$$

Alternatively, each the component characteristic quantities may be suitably weighted (i.e., given varying intensities), as follows:

$$Q = \alpha A + \beta B + \gamma C \gamma \qquad \text{(Expression 7)}$$

where, symbols $\alpha$, $\beta$ and $\gamma$ represent the weights of the respective characteristic quantities.

As described, the embodiment of FIG. 7 is capable of combining a plurality of characteristic quantities into a new characteristic quantity in the recognition process. This feature makes it possible to recognize complicated motions/actions having diverse characteristic quantities.

Figure 8:
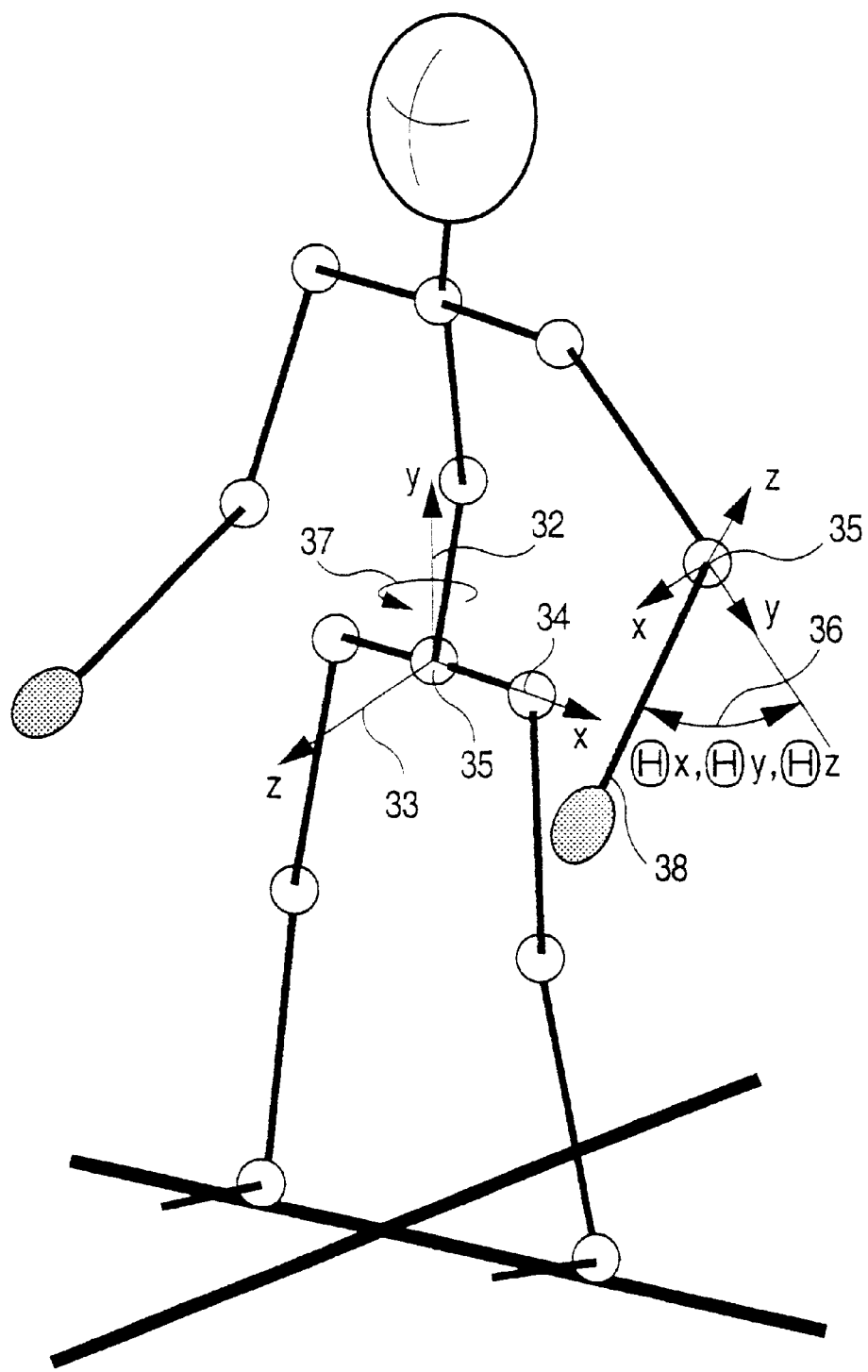
FIG. 8 is an explanatory view depicting points and axes for measuring status changes.

Described below with reference to FIG. 8 is another embodiment of the invention wherein a plurality of status change measuring instruments are utilized.

In the embodiment of FIG. 1, the status change measuring instrument was attached to the position of the object's waist 31 in FIG. 8, and measurements were taken along an axis 32 (i.e., in the body's height direction). In that setup, only the status change in the body's height direction could be measured. The human body's center of gravity is said to exist approximately in the position of the waist. Thus when a man in a standing position raises his hand(s), the position of the waist slightly moves in the direction opposite to that in which the hand was raised. To observe such a waist movement requires setting up another measuring instrument for measuring the status change in the direction of an axis 34. Likewise, when the object tilts his head forward or backward, yet another measuring instrument needs to be installed in the direction of an axis 33. Furthermore, to measure revolutions of the waist requires establishing another measuring instrument in the rotating direction 37 along the axis 32. For more detailed data gathering, it is necessary additionally to measure movements 36 of the left-hand elbow 35.

Illustratively, the object under observation is recognized for a principal motion such as "walking" or "running" along the axis 32, and also recognized for more detailed motions such as "raising the right hand," "tilting the head" and "twisting the waist" along the axes 33 and 34 as well as in the rotating direction 37 around the axis 32. The measurements thus taken permit recognition of such complicated motions/actions as "raising the right hand while walking," "tiling the head while running" and "twisting the waist when standing up."

As described, the embodiment of FIG. 8 has a plurality of status change measuring instruments attached to the object under observation, and combines results measured and recognized through the respective instruments. Acting as it does, the embodiment can recognize more detailed motions and actions of the object under observation.

Although the embodiment of FIG. 8 was described with emphasis on its ability to detect spatial movements of various parts of the human body, this is not limitative of the invention in terms of where measuring instruments may be installed or what kind of status change may be measured. For example, measuring instruments may be attached to various parts of the human object's face to monitor their movements as a status change representing changing facial expressions. Furthermore, instead of detecting spatial movements of diverse parts of the object's face or body, a variation of the invention may use measuring instruments in such a way that directly detects conditions of the muscles producing such status changes.

Another embodiment of the invention is described below with reference to FIG. 9. This embodiment is a recognition system that judges characteristic quantities of motions/actions of the object under observation in a generalized manner using physical quantities other than acceleration and biological data as needed, thereby recognizing the object's motions/actions.

Figure 9:
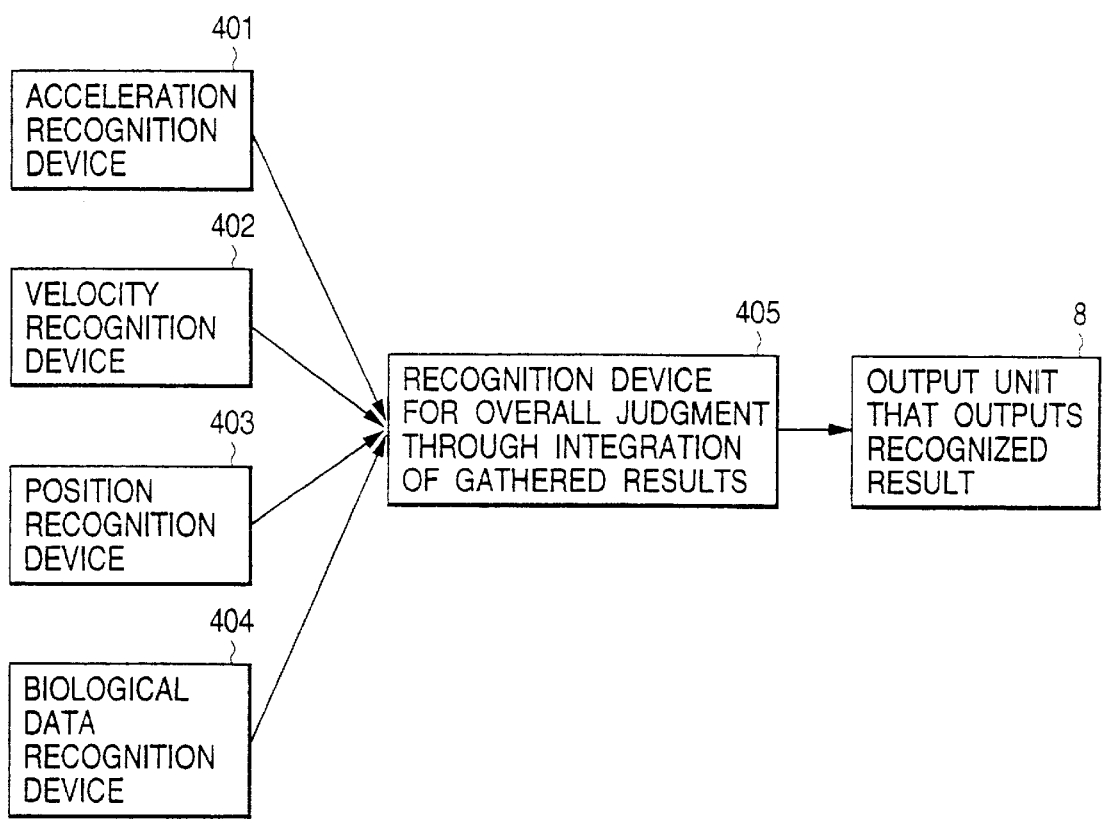
FIG. 9 is a block diagram of a recognition system practiced as another embodiment of the invention.

The recognition system embodying the invention as outlined in FIG. 9 illustratively comprises: recognition devices 401 through 404 for performing recognition processing based on various data measured by measuring instruments attached to the object under observation; a recognition device 405 for performing an overall recognition process integrating the recognized results from the upstream recognition devices; and an output unit 8 for outputting the eventual result of recognition.

The recognition device 401 is a device that performs recognition processing based on acceleration data supplied from an acceleration sensor such as that of the embodiment in FIG. 1. The acceleration sensor is attached to the object under observation.

The recognition device 402 performs its recognition process based on velocity data. For example, the recognition device 402 receives changes in the velocity of the object under observation (e.g., a human being) and judges whether the object is, say, walking or moving aboard a vehicle.

The recognition device 403 carries out its recognition process based on position data. In operation, the recognition device 403 recognizes the action of the object under observation upon receiving data on where the object under observation is positioned or what locus the object is plotting in motion.

The recognition device 404 executes recognition processing on the basis of biological data. Biological data include pluse count, blood pressure, body temperature, blood sugar count, respiration, electromyogram, electrocardiogram, blood flow and electroencephalogram. If the object under observation is a human being, the biological data vary depending on his or her activity. The recognition device 404 recognizes the condition in which the human being is placed by receiving varying biological data. For example, when the object performs a physical exercise, both the pulse count and the respiration rise. Differences in the body's posture may be judged by selecting an appropriate location where the blood pressure is measured. The amount of physical activity, mental condition and physical fitness may be judged by temperature changes. Electroencephalogram reveals whether or not the subject is awake. Physical fitness may also be judged by the blood sugar count. The body's status of physical activity may be judged by changes in electromyogram.

The recognition devices 402, 403 and 404 observe measured data in the form of waveforms. The waveforms are converted from analog to digital format. In the same manner in which the recognition device 401 acquires the characteristic quantity of acceleration, the devices 402, 403 and 404 extract characteristic quantities from their respective digitized signals. The extracted characteristic quantities are processed for motion recognition.

Acting individually, the recognition devices 401 through 404 may get ambiguous results from their recognition processes and may suffer incorrect recognition therefrom. This potential problem is circumvented by the embodiment of FIG. 9 using the recognition device 405 that integrates the recognized results from the devices 401 through 404 for overall judgment of the object's motions/actions. The eventually recognized result is output by the output unit 8.

As described, the embodiment of FIG. 9 implements overall judgment based on the recognized results from a plurality of sensing entities, whereby a more accurate result of recognition is obtained.

Figure 10:
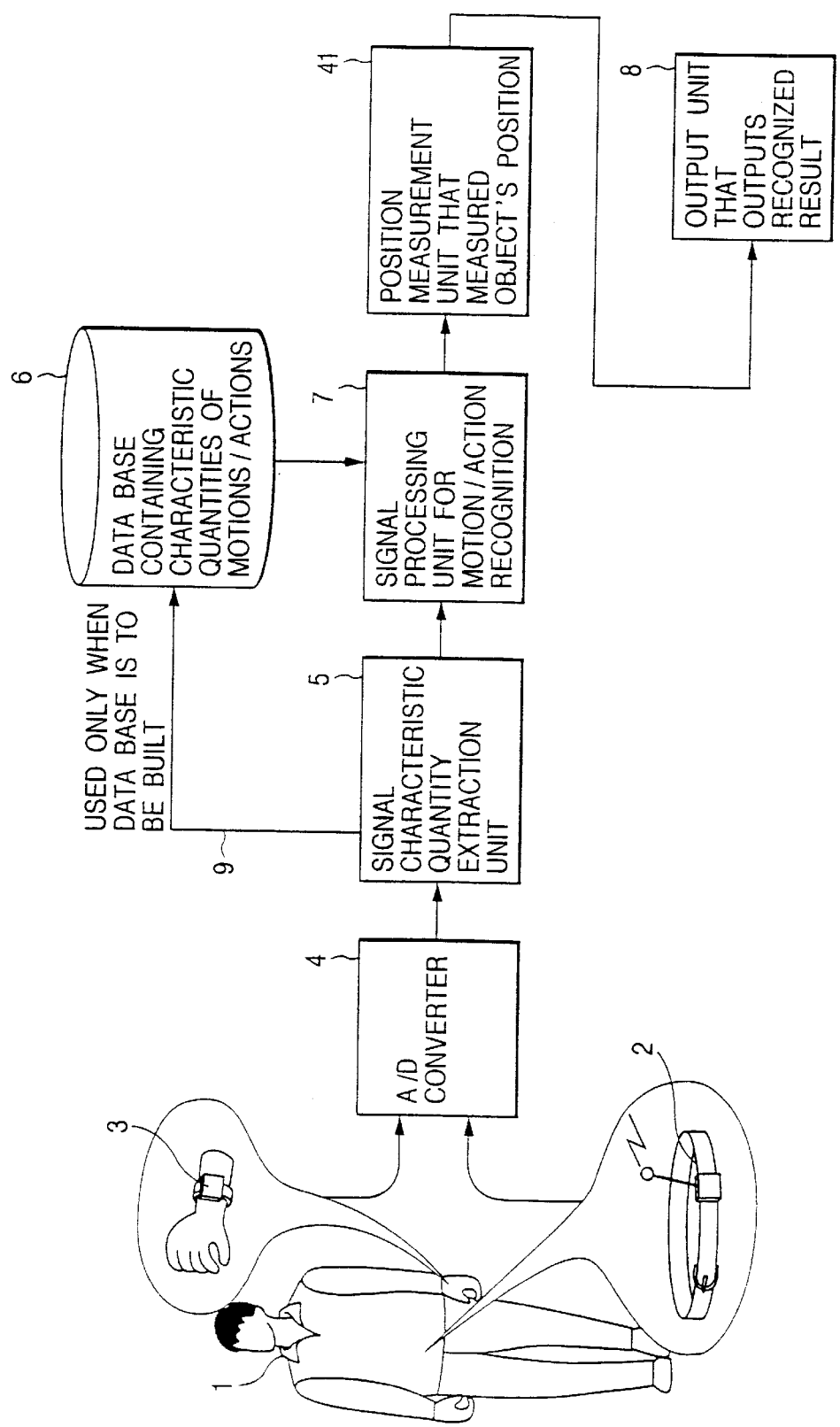
FIG. 10 is a block diagram of a motion and action recognition device combined with a position measurement unit to embody the invention.

Another embodiment of the invention is described below with reference to FIGS. 10 and 11. This embodiment is a recognition device that combines the recognition of the objects' motions and actions with the recognition of the moving object's position. FIG. 10 is a block diagram of this embodiment, and FIG. 11 is an explanatory view showing how positions are measured by this embodiment.

As shown in FIG. 10, the recognition device embodying the invention has a position measurement unit 41 added to the setup in FIG. 1, the unit 41 measuring positions of the object 1 under observation. In the setups of FIGS. 10 and 1, like reference numerals designate like or corresponding parts, and their descriptions are hereunder omitted where redundant.

The position measurement unit 41 is implemented illustratively by use of a cellular system that will be described shortly. Another positioning system that may be used with the invention is one in which the object 1 is equipped with a transmitter transmitting a radio signal. The signal is received by a plurality of receivers located at different points, and the received signals are processed to find the position of the signal source. In another alternative positioning system for use with the invention, radio signals are received from a plurality of reference signal sources, and the received signals are processed to find the observer's position (GPS, Omega, LORAN, Decca, etc.). In yet another alternative positioning system, laser, magnetic fields and/or ultrasonic waves may be used for positioning. Any of these positioning systems may be used in conjunction with the embodiment to achieve the intended purpose.

Figure 11:
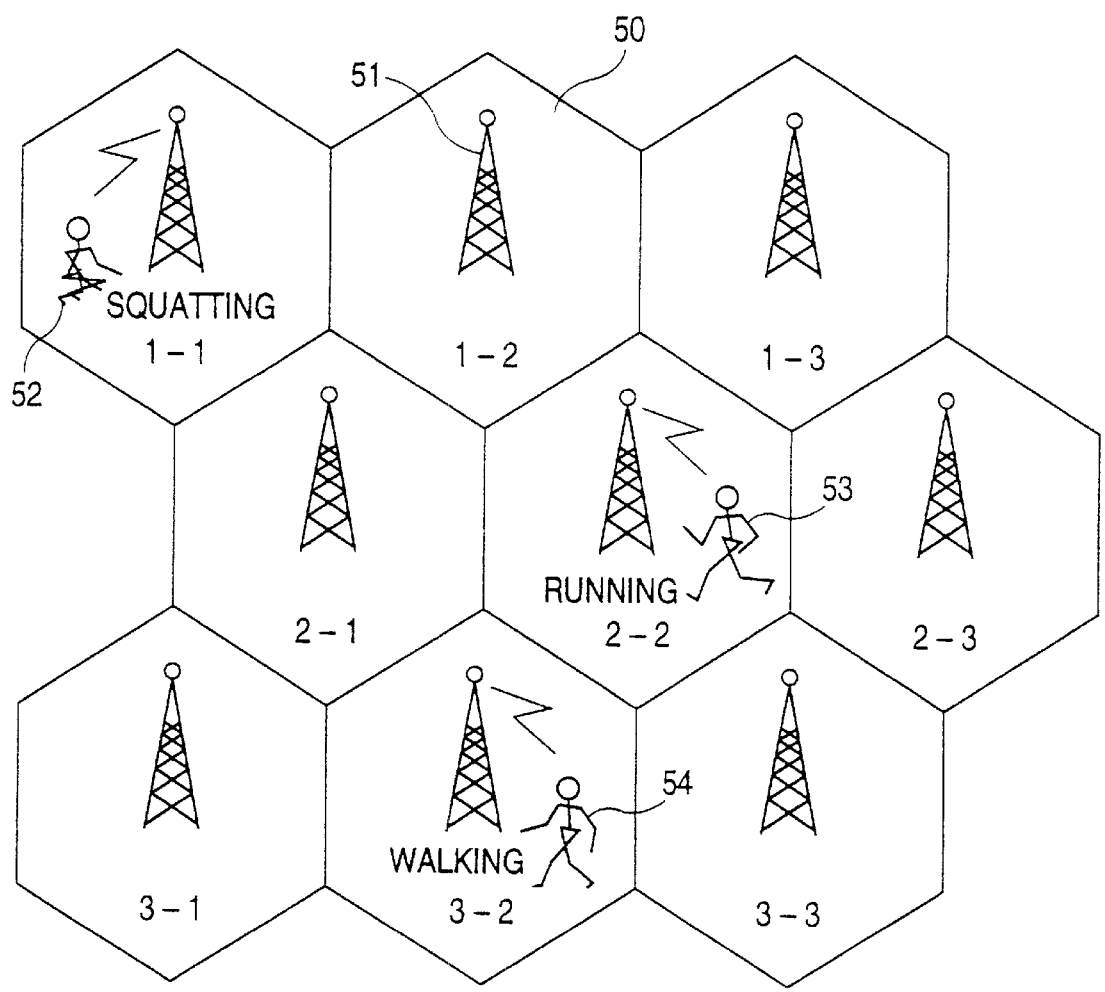
FIG. 11 is an explanatory view outlining a position measurement method used by the embodiment of FIG. 10.

The cellular system for use with the embodiment of FIG. 10, depicted in FIG. 11, is one in which a plurality of antennas 51 are located one each in a plurality of areas 50 called cells or zones. Communication via one antenna 51 is limited to one cell 50 corresponding to that antenna. To communicate from within an adjacent cell requires switching to the antenna of that cell. In this system, each cell in which to communicate is so small that the zone comprising a signal transmitter may be located by isolating the currently communicating antenna. In this example, cells are numbered 1-1 through 3-3, and objects under observation are given numerals 52, 53 and 54.

With this embodiment, it is assumed that each object is equipped with the measuring instruments 2 and 3 as well as processors 4 through 7 from among the components in FIG. 10, and that the recognized result from the signal processing unit 7 is transmitted via the cellular system. That is, the position measurement unit 41 of this embodiment is implemented by combining a transmitter and a receiver. The transmitter is used to transmit the recognized result to the antenna of the cell to which each object 1 under observation belongs, and the receiver is employed to receive the recognized result transmitted via that antenna.

The action of the object 52 (squatting, in this example) is recognized by the same technique described in connection with the embodiment of FIG. 1. The recognized result is sent via the antenna of the cell 1-1. This allows the object 52 to be recognized as "squatting" inside the cell 1-1. Similarly, the object 53 is recognized as "running" inside the cell 2-2, and the object 54 is recognized as "walking" in the cell 3-2.

As described, the embodiment of FIG. 10 permits recognition of where the objects under observation are currently positioned and what their current motions/actions are like.

Another embodiment of the invention is described below with reference to FIGS. 12 through 14. This embodiment is a recognition system capable of estimating the action and work status of the object under observation, as well as the environment and position in which the object is placed.

Figure 12:
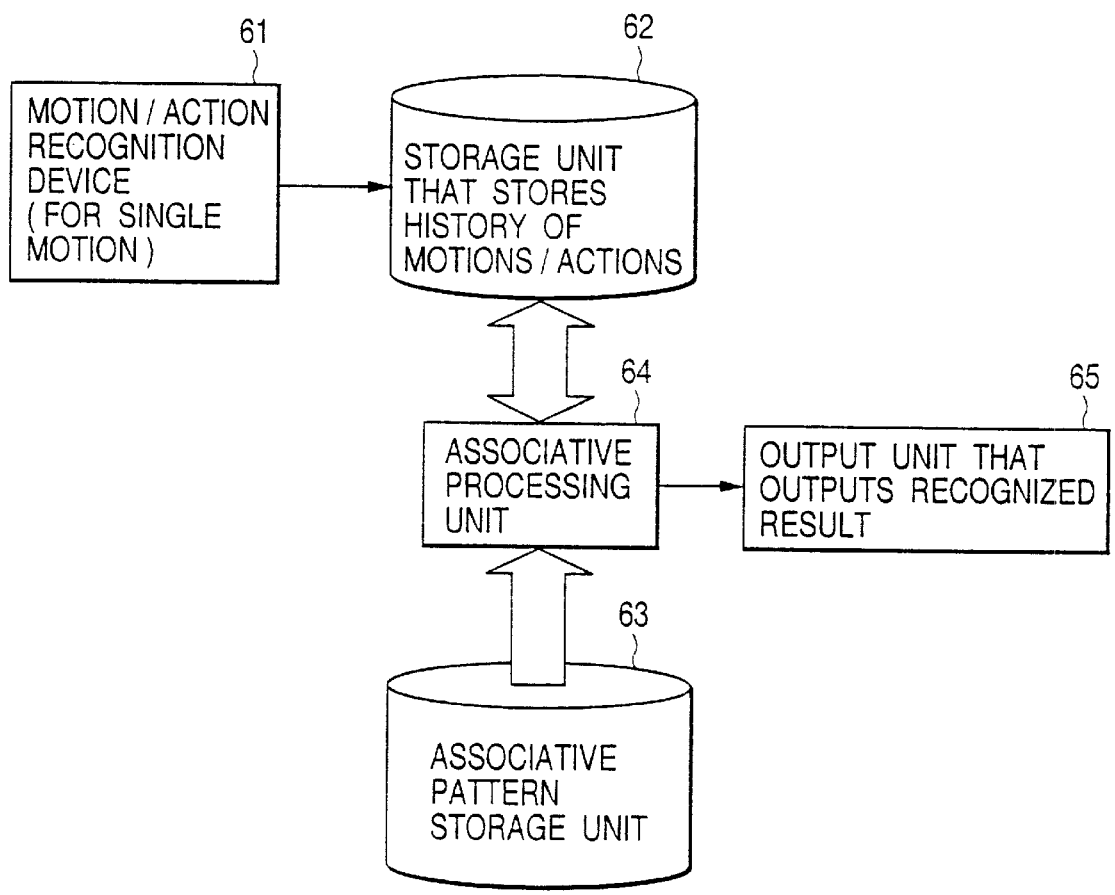
FIG. 12 is a block diagram of a recognition system for estimating the object's work status or the environment in which the object is placed on the basis of an accumulated work history.

As shown in FIG. 12, the recognition system embodying the invention illustratively comprises: a recognition device 61 for recognizing a single motion/action; a storage unit 62 for storing a history of recognized motions/actions; a storage unit 63 for accommodating a previously prepared database of associative patterns; an associative processing unit 64 for determining by association or for estimating the object's action or work status or the environment in which the object is placed, through the use of data in the storage units 62 and 63; and an output unit 65 for outputting the associated or estimated result.

The recognition device 61 for motion/action recognition is identical in structure to those of the embodiments in FIGS. 1 and 10. However, the present embodiment has no need for the output unit 8 of the preceding embodiments. As outlined above, the recognition device 61 recognizes only one motion/action that occurs within a certain period of time. As such, the embodiment is not suitable for recognizing work composed of a plurality of motions/actions accumulated.

The embodiment of FIG. 12 thus places each motion or action recognized by the recognition device 61 into the storage unit 62 which stores a history of motions/actions. In the storage unit 62, the motions/actions are arranged and recorded on a time series basis, as with data 71 in FIG. 13.

The stored history data 71 are monitored by the associative processing unit 64 in reference to the stored patterns in the associative pattern storage unit 63. An associative pattern is a pattern indicating the correspondence between a combination of a plurality of motions including unrecognizable ones on the one hand, and a task associated with that combination of motions, as shown in FIG. 14.

How the embodiment of FIG. 12 works will now be described by taking an example of inspection work done by a service engineer at a plant. This kind of inspection work required in any one zone (area) of the plant is considerably limited in scope. That is, a small number of motions/actions in combination are sufficient for the content of work to be estimated. A pattern 81 in FIG. 14 represents a typical assortment of motions such as "climbing a ladder," "walking" and an "unrecognizable motion." The unrecognizable motion in this case is a motion of which the presence is detected but which is too complicated to be recognized by the recognition device 61.

In the example of FIG. 14, if the only remaining task to be conceivably carried out after the service engineer has climbed the ladder is a console operation, then the "unrecognizable" motion is estimated as the console operation. In addition, the recognized motion of "climbing the ladder" allows the environment in which the subject (i.e., service engineer at the plant) is placed to be estimated as an elevated location. Thus the task recognized by association or by estimation based on the series of motions "climbing the ladder," "walking" and "unrecognizable motion" is defined as the console operation at the elevated location. Likewise, a motion pattern 83 comprising motions of "descending a staircase," "walking," "squatting" and "unrecognizable motion" may be recognized by association as "a valve operation on the floor."

By referring to such associative patterns, the associative processing unit 64 continuously monitors the storage unit 62 that stores the history of motions/actions. For example, if the same motion pattern as the pattern 81 occurs in the monitored data, as in a segment A (72) in FIG. 7, then the associative processing unit 64 outputs a recognized result indicating that the object 1 is performing "a console operation at an elevated location." Similarly, because the same motion pattern as the associative pattern 83 appears in a segment B (73), the object is recognized in that segment as performing "a valve operation on the floor."

Not only the content of work but also the position thereof may be identified by this embodiment. Illustratively, suppose that the recognition device in FIG. 10 is used as the recognition device 61 and that the cellular system in FIG. 11 is used as the position measurement unit 41. In such a case, the precision of position measurement is necessarily coarse; only the zone in which the object is located is identified. However, if that setup is combined with this embodiment and if the place where "a console operation at an elevated location" occurs is limited to a single spot inside the zone in question, then the recognition of the object performing "a console operation at an elevated location" leads to identification of the object's exact position where the console operation is carried out at the elevated location.

As described, the embodiment of FIG. 12 offers the benefit of recognizing the object's action and work status as well as the environment in which the object is placed, by use of a history of multiple motions and patterns of combined motions.

In addition, the embodiment makes it possible to estimate motions hitherto unrecognized by conventional methods of waveform-based recognition. A conventionally unrecognizable motion may be estimated by referring to a suitable history of motions and to the contents of the tasks due to take place in the appropriate context.

If sites are predetermined at which particular tasks are supposed to be performed, the embodiment may recognize the kind of work being done by the subject and utilize the recognized result in identifying the exact spot where the subject is currently engaged in the task.

Another embodiment of the invention is described below with reference to FIGS. 15, 16A and 16B. The embodiment is an apparatus that presents the subject with an indication of difference between the measured motion and the corresponding reference motion.

This embodiment applies specifically to a setup where a disabled subject (e.g., a patient with a leg injury from an accident) is rehabilitated. The reference motion signifies a pre-injury motion such as normal walking; the measured motion is illustratively the current style of walking managed by the subject being rehabilitated.

Figure 15:
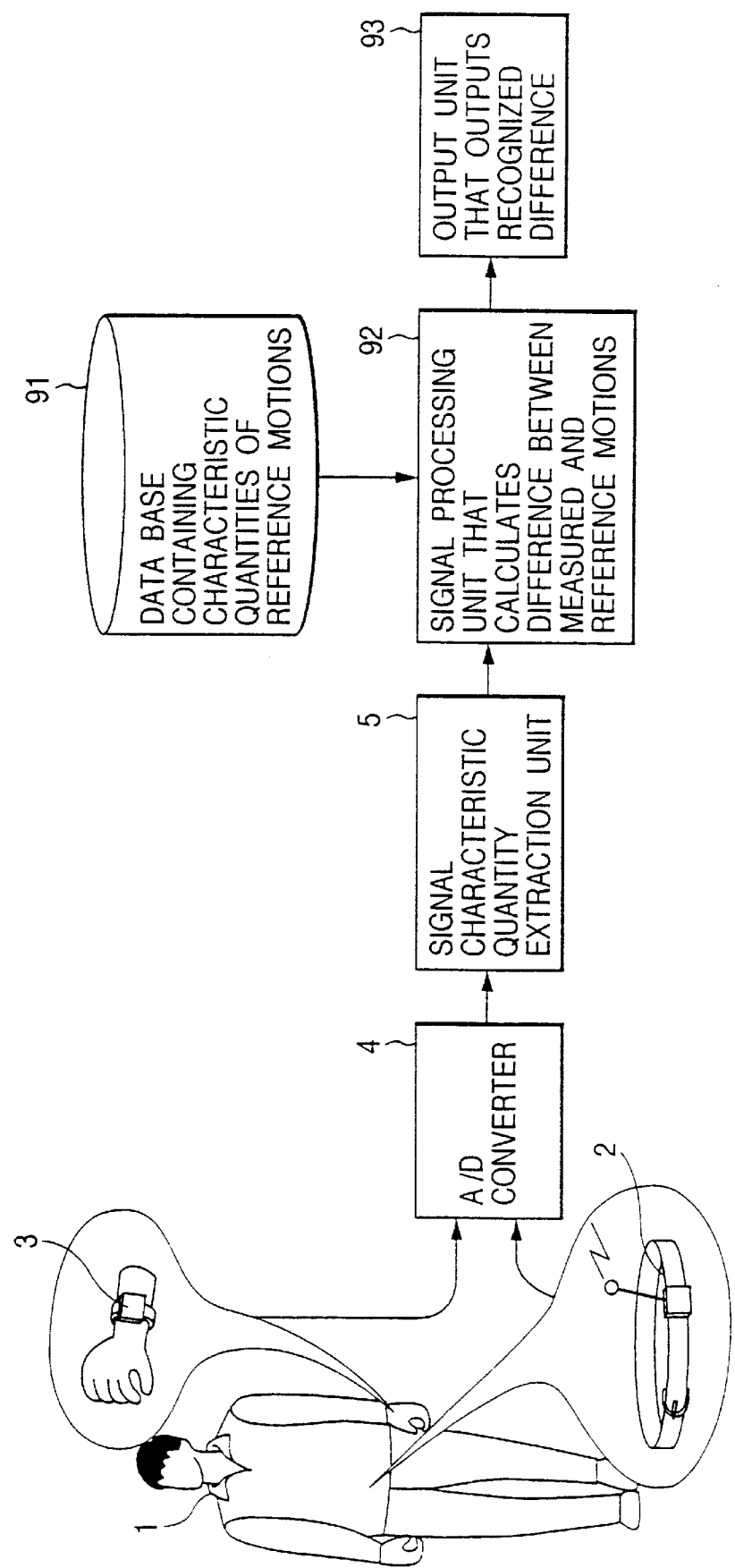
FIG. 15 is a block diagram of a recognition device practiced as another embodiment of the invention, the device displaying a difference between a reference motion and a measured motion.

As shown in FIG. 15, the embodiment illustratively comprises: measuring instruments 2 and 3 attached to the subject 1 under observation; an A/D converter 4 for converting measured results from the instruments 2 and 3 into digital format; a characteristic quantity extraction unit 5 for extracting a characteristic quantity from digitized measurements; a reference motion characteristic quantity database 91 containing characteristic quantities premeasured and pre-extracted from reference motions and actions; a signal processing unit 92 for detecting a difference between the motion whose characteristic quantity was extracted by the characteristic quantity extraction unit 5 on the one hand, and the corresponding reference motion held in the reference motion characteristic quantity database 91 on the other hand; and an output unit 93 for outputting the detected difference.

Ideally, the reference motion characteristic quantity database 91 should have characteristic quantities representing the object's own normal motion before his or her injury. Failing that, the database 91 may contain characteristic quantities obtained by averaging motions sampled from numerous people. The signal processing unit 92 calculates the difference between such a reference motion and the object's currently managed motion, as illustrated in FIGS. 16A and 16B. Here, the reference motion is assumed to be represented by a frequency spectrum 101 in subfigure (a).

Where rehabilitation is yet to make an appreciable progress, the subject has difficulty executing the motion smoothly. In that case, as shown by a frequency spectrum 102 in subfigure (b), the difference between the subject's motion and the corresponding reference motion appears pronounced, especially in spectrum components 106 and 107. The difference (in absolute value) between the frequency spectra 101 and 102 is represented by a frequency spectrum 104. The resulting difference includes spectrum components 108 and 109 shown pronounced because of the subject's inability to execute the motion smoothly. The subject being rehabilitated is presented with the spectrum difference output by the output unit 93. The output provides a visual indication of how the subject's motion currently differs from the reference motion.

The object being rehabilitated tries to minimize the pronounced spectrum components in the detected result. That is, the subject continues rehabilitation efforts so that the measured spectrum will become ever closer to the reference frequency spectrum 101, as evidenced by a frequency spectrum 102 in FIG. 16B. When the whole rehabilitation session is deemed completed, the subject's motion should become substantially identical to the reference motion, with no pronounced spectrum difference appearing, as evidenced by a frequency spectrum 105.

Although the above embodiment was shown to apply to disabled patients' rehabilitation, this is not limitative of the invention. The embodiment may also apply to the correction of athletes' skills with reference to desired performance levels.

As described, the embodiment provides the benefit of automatically presenting the subject being rehabilitated or practicing athletic skills with an explicit indication of how he or she has progressed with respect to the reference motion.

Another embodiment of the invention is described below with reference to FIG. 17. This embodiment is a recognition device capable of detecting a difference between a reference motion and a measured motion and presenting the object under observation with an indication of a probable cause of the detected difference.

Figure 17:
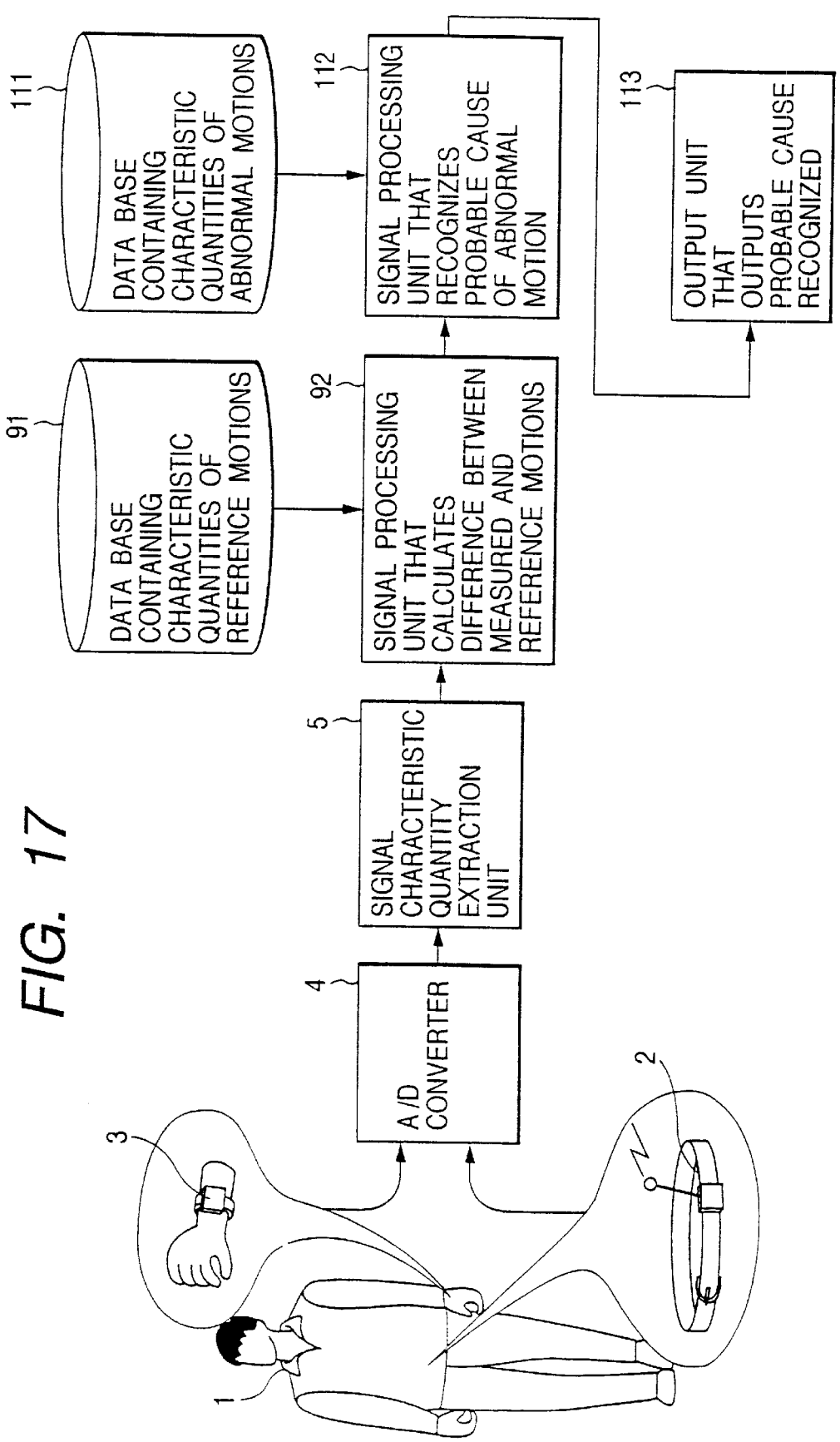
FIG. 17 is a block diagram of a recognition device practiced as another embodiment of the invention, the device detecting the difference between a measured and a reference motion and outputting a probable cause of the difference.

As illustrated in FIG. 17, this recognition device embodying the invention is the recognition device of FIG. 15 supplemented with a database 111 of characteristic quantities denoting abnormal motions and with a signal processing unit 112 (called the second signal processing unit hereunder) for recognizing the probable cause of an abnormal motion. The abnormal motion signifies an unnatural motion different from what is generally deemed a normal and typical (i.e., reference) motion. One such abnormal motion is a walk of a disabled person with a leg injury resulting from an accident. The abnormal motion characteristic quantity database 111 contains characteristic quantities denoting diverse kinds of abnormal motions. For example, if the spectrum frequency 104 in FIG. 16A is produced because the way the right leg's toes are raised differs from the reference motion, then the resulting spectrum components 108 and 109 are formed by characteristic quantities representing the probable cause of the motion perceived to be "abnormal." Characteristic quantities extracted from such abnormal motions are stored beforehand into the database 111 of abnormal motion characteristic quantities.

By referencing the abnormal quantity characteristic quantity database 111, the second signal processing unit 112 recognizes the probable cause of the abnormal motion exhibited by the object under observation. The recognition process is carried out in the same manner as the previously described motion/action recognition scheme. That is, the signal processing unit 92 first calculates the difference between the measured motion and the corresponding reference motion. The second signal processing unit 112 then correlates the difference with the characteristic quantities of abnormal motions stored in the abnormal motion characteristic quantity database 111. After the second signal processing unit 112 recognizes the probable cause represented by the characteristic quantity with the highest degree of correlation, the recognized result is output by the output unit 113 using letters or graphics.

Although the embodiment of FIG. 17 was shown applying to disabled patients' rehabilitation, this is not limitative of the invention. The embodiment may also apply to the correction of athletes' skills with reference to desired performance levels.

As described, the embodiment of FIG. 17 provides the benefit of automatically recognizing and indicating the probable cause of any motion deemed aberrant with respect to the reference motion.

Another embodiment of the invention is described below with reference to FIG. 18. This embodiment is a recognition system using inventive motion/action recognition devices to collect work data for use by a workability evaluation system or a work content evaluation system.

Workability evaluation or work content evaluation is an actively studied field in the discipline of production control engineering. To carry out workability evaluation or work content evaluation first of all requires collecting work data. Traditionally, such collection of work data has been dependent on a large amount of manual labor. The embodiment of FIG. 18 is intended to replace the manual gathering of work data with an automated data collection scheme.

Figure 18:
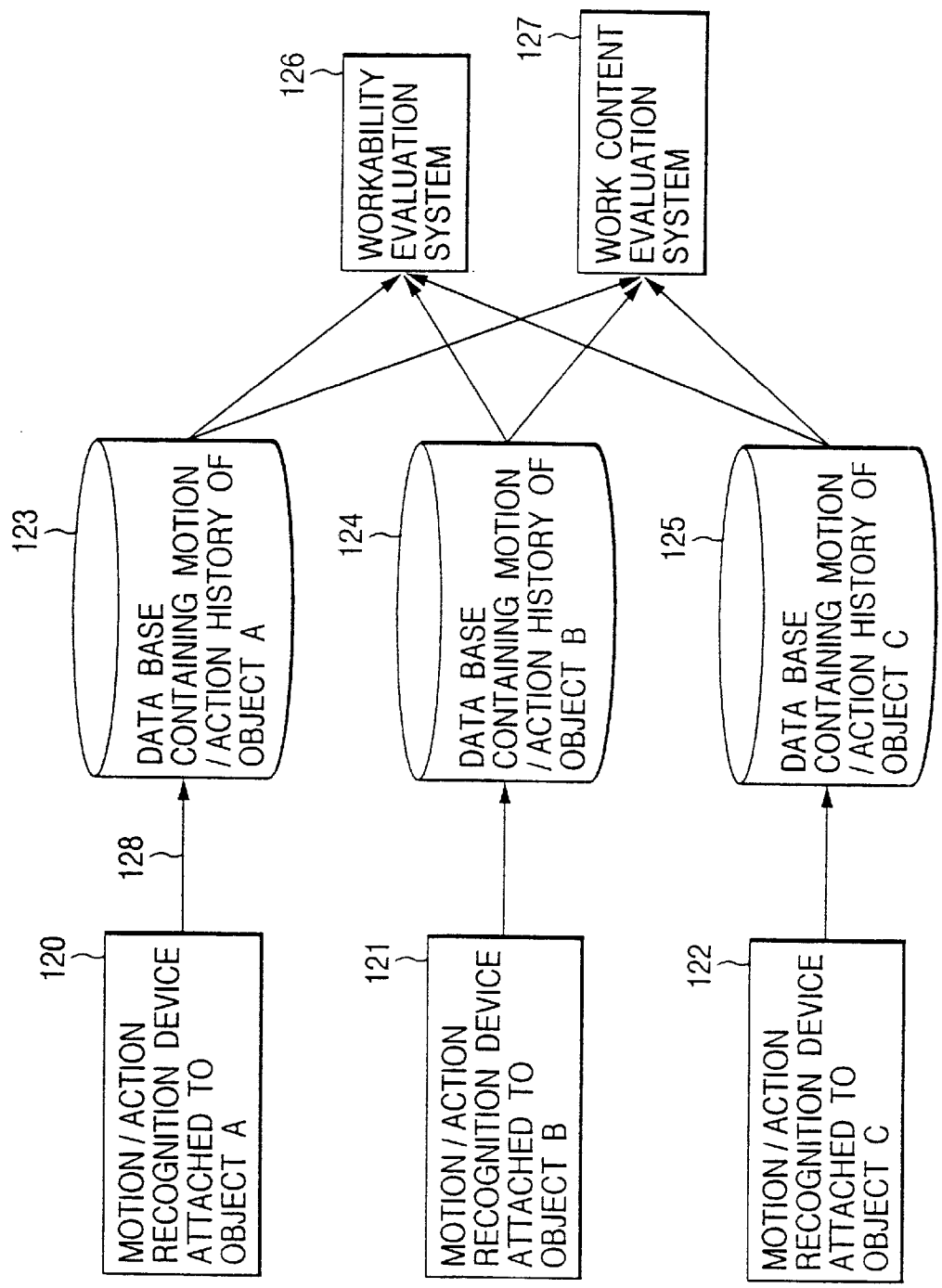
FIG. 18 is a block diagram of a recognition system comprising inventive recognition devices to gather work data for use by a workability evaluation system or a work content evaluation system.

As shown in FIG. 18, the system embodying the invention illustratively comprises: recognition devices 120, 121 and 122 attached to objects A, B and C respectively; databases 123, 124 and 125 for storing recognized results from the recognition devices; and a workability evaluation system 126 as well as a work content evaluation system 127 for receiving histories of the objects' motions and actions held in the respective databases.

The inventive recognition devices 120, 121 and 122 attached to the objects A, B and C recognize their motions/actions automatically and continuously as they occur. Specifically, the recognition devices may be of the same type as those used in the embodiments of FIGS. 1 and 10. Recognized results are transmitted over transmission paths 128 to the databases 123, 124 and 125 which accumulate histories of the objects' motions and actions recognized. The transmission paths 128 may be either wired or wireless. Wireless transmission paths have the benefit of allowing the objects under observation to move freely.

The values retained in the databases containing motion/action histories are referenced by the workability evaluation system 126 or work content evaluation system 127. Each of the systems performs its own evaluation process based on the referenced result.

The present embodiment is characterized by its ability to collect work data automatically. This feature leads to drastic reductions in the amount of manual labor traditionally required for such data gathering.

The embodiment of FIG. 18 is a typical application of the invention to the activity of work data collection, and is in no way limitative of the workability evaluation system 126 and work content evaluation system 127 in terms of their specific capabilities.

Another embodiment of the invention is described below with reference to FIG. 19. This embodiment is a recognition system using inventive motion/action recognition devices to collect work data for use by an optimum personnel allocation system or an optimum work time allocation system.

The optimum personnel allocation system is a system that controls the number of personnel to be allocated to each of a plurality of work segments in consideration of the work loads on the allocated personnel. The optimum work time allocation system is a system that controls work time periods for personnel depending on their work loads. Each of the systems requires that the content of work performed by a large number of personnel be grasped in real time. This embodiment is intended to fulfill the requirement by implementing a scheme whereby the content of work done by numerous workers is easily recognized in real time.

Figure 19:
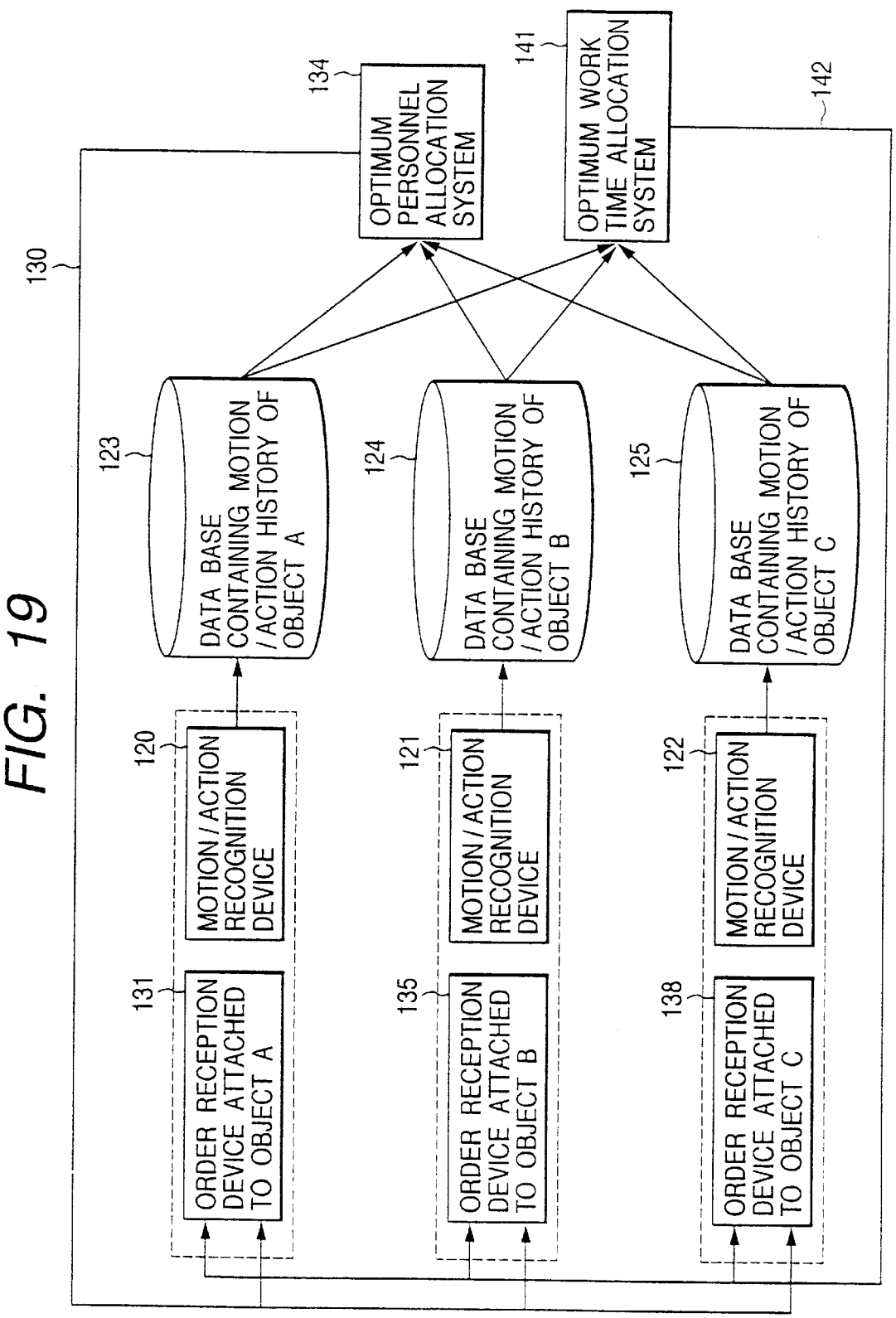
FIG. 19 is a block diagram of a recognition system comprising inventive recognition devices to gather work data for use by an optimum personnel allocation system or an optimum work time allocation system.

As shown illustratively in FIG. 19, the recognition system embodying the invention is in part composed of the recognition devices 120, 121 and 122 as well as the databases 123, 124 and 125 in FIG. 18. These components are supplemented with an optimum personnel allocation system 134 and an optimum work time allocation system 141 utilizing data held in the above databases. The embodiment is additionally furnished with order reception devices 131, 135 and 138 which are attached to objects A, B and C respectively and which receive orders from the allocation systems.

The motion/action recognition devices 120, 121 and 122 attached to the objects A, B and C recognize the latter's motions/actions automatically and continuously as they occur. Histories of the objects' motions and actions thus recognized are accumulated in the databases 123, 124 and 125. Data transmission paths to the databases may be of wireless type. Wireless transmission paths have the advantage of allowing the objects under observation to move freely.

The values retained in the databases containing motion/action histories are referenced by the optimum personnel allocation system 134 or optimum work time allocation system 141. Given the reference data, each of the systems judges how much work load each worker is subjected to by use of predetermined methods. For example, if the optimum personnel allocation system 134 judges on the basis of the received data that a certain worker is excessively loaded with work, then another worker with less or no work load is called up via a data transmission path 130 and is ordered to assist the overloaded worker.

If the optimum work time allocation system 141 senses that the cumulative load on a certain worker has exceeded a predetermined level, the system urges the overloaded worker to take a rest and allocates another worker to the task in question. The orders necessary for the allocation process are sent over a path 142 to the order reception devices attached to the applicable workers.

As described, the embodiment of FIG. 19 offers the benefit of allowing the content of work performed by numerous personnel to be easily recognized in real time so that the personnel may be allocated optimally depending on their current work status.

Another embodiment of the invention is described below with reference to FIG. 20. This embodiment is a recognition system using an inventive motion/action recognition device to announce that a specific motion or action has been carried out by an object under observation.

This recognition system embodying the invention is applied to a setup where supervisors or custodians in charge of people who are socially vulnerable and need protection or of workers working in isolation are automatically notified of a dangerous situation into which their charge may fall for whatever reason. This embodiment includes components identical to some of those constituting the embodiment of FIG. 12. The parts having their structurally identical counterparts in the setup of FIG. 12 are designated by like reference numerals, and their detailed descriptions are hereunder omitted where redundant.

Figure 20:
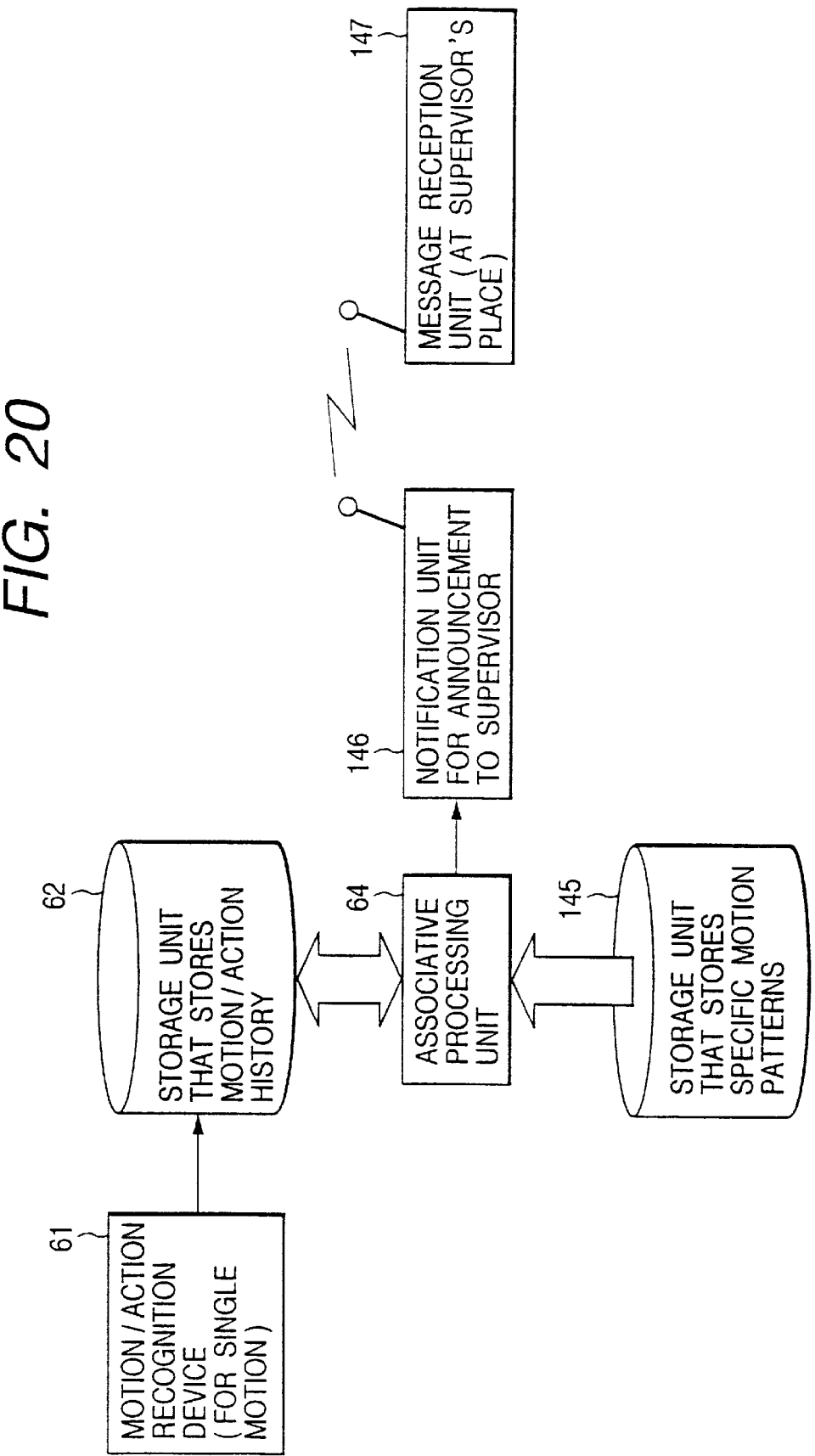
FIG. 20 is a block diagram of a recognition system comprising an inventive recognition device to announce that a specific motion or action has been carried out by an object under observation.

As shown in FIG. 20, the recognition system embodying the invention illustratively comprises: a motion/action recognition device 61; a storage unit 62 for storing a history of recognized motions/actions; a storage unit 145 for storing specific motion patterns; an associative processing unit 64 for recognizing by association or for estimating a specific motion or action of the object under observation; a notification unit 146 for transmitting a specific message to the supervisor or custodian depending on the result of the association or estimation process; and a message reception unit 147 for receiving the transmitted message.

The motion/action recognition device 61 is equivalent to the recognition device used in the embodiment of FIG. 1. As described earlier, this recognition device is capable of recognizing a single motion or action that takes place within a limited period of time; it is not suitable for recognizing any action or work composed of a plurality of motions or actions performed cumulatively. All motions/actions are recognized continuously as they occur and stored into the storage unit 62 that accommodates a history of motions/actions.

The history data thus stored are continuously monitored by the associative processing unit 64 in reference to the motion patterns held in the specific motion pattern storage unit 145. A specific motion pattern is a combination of multiple motions necessary for recognizing a specific action such as "a sudden collapse onto the ground" or "a fall from an elevated location."

For example, the action of "a sudden collapse onto the ground" is recognized as a motion pattern made up of a motion of "a walking or standing-still posture" followed by a motion of "reaching the ground in a short time" which in turn is followed by a motion "lying still on the ground." Similarly, the action of "a fall from an elevated location" is recognized as a motion pattern constituted by motions of "climbing," "falling," "hitting obstacles," "reaching the ground" and "lying still," occurring in that order.

The motion of "climbing" is recognized by detecting an upward acceleration greater than gravitational acceleration. The motions of "falling," "hitting obstacles" and "reaching the ground" are recognized respectively by detection of "zero acceleration in all directions (because of free fall)," "intense acceleration occurring in different directions in a short time" and "suffering a considerably strong acceleration."

By resorting to such motion patterns to recognize the motion of the object under observation, the embodiment of FIG. 20 eliminates possible erroneous recognition of motions or actions. For example, suppose that a sensor is detached from the object's body and placed violently on a table. In that case, the sensor detects a considerably strong acceleration which, by use of a single motion recognition device, may likely be interpreted as indicative of the subject falling from an elevated location or collapsing onto the ground. This is because the single motion recognition device has no recourse to a history of the object's multiple motions. By contrast, the associative processing unit is capable of checking motions before and after, say, the strong acceleration detected in the above example, whereby the object's condition is better grasped and the result of recognition is made more accurate. Illustratively, if the sensor has detected a kind of acceleration inconceivable when mounted on the human body, that acceleration may be recognized correctly as a motion of the sensor being detached from the body, as long as the acceleration has been classified in advance as pertaining to that particular motion. In this manner, the incidence of a single motion being erroneously recognized can be minimized.

When the associative processing unit 64 detects any such specific motion pattern from among the history data in the storage unit 62, the unit 64 causes the notification unit 146 to notify the supervisor or custodian of a message indicating what the recognized specific motion pattern signifies. The supervisor or custodian receives the message via the message reception unit 147 and thereby recognizes the situation in which the object under observation is currently placed.

As described, the embodiment of FIG. 20 offers the benefit of allowing supervisors or custodians in charge of people who are socially vulnerable and need protection or of workers working in isolation to be automatically notified of a dangerous situation in which their charge may be placed for whatever reason.

As a variation of the embodiment in FIG. 20, the system may be supplemented with the position measurement unit 41 described with reference to FIG. 10 as a means for measuring the object's position. Alternatively, the embodiment may be supplemented with the associative processing unit 64 of FIG. 12 for identifying the object's position based on a history of the latter's motions. With any of these variations, the position data about the object who may be in a dangerous or otherwise aberrant situation are sent to the supervisor or custodian, so that the latter will recognize where the object is currently located and what has happened to him or her.

In the setup where the position measurement unit 41 is additionally furnished to measure specific motion patterns, arrangements may be made to permit a choice of reporting or not reporting the recognized motion pattern depending on where the incident is observed. This feature is useful in averting a false alarm provoked by an apparent collapsing motion of the object under observation when in fact the object is lying on a couch for examination at a hospital or climbing onto the bed at home.

Another embodiment of the invention is described below with reference to FIG. 21. This embodiment is a recognition system applying inventive motion/action recognition devices to behavioral analysis, behavior tracking and behavior monitoring.

This recognition system embodying the invention will be described in connection with a typical setup for behavioral analysis of animals. In this field, there exist numerous studies on the loci traced by animal movements. So far, there has been only one way of observing the motions/actions of animals: through the eyes of humans. There are many aspects yet to be clarified of the behavior and motions of animals that inhabit locations unobservable by humans. This embodiment is intended to track automatically the yet-to-be-revealed motions/actions of such animals in their unexplored territories.

Figure 21:
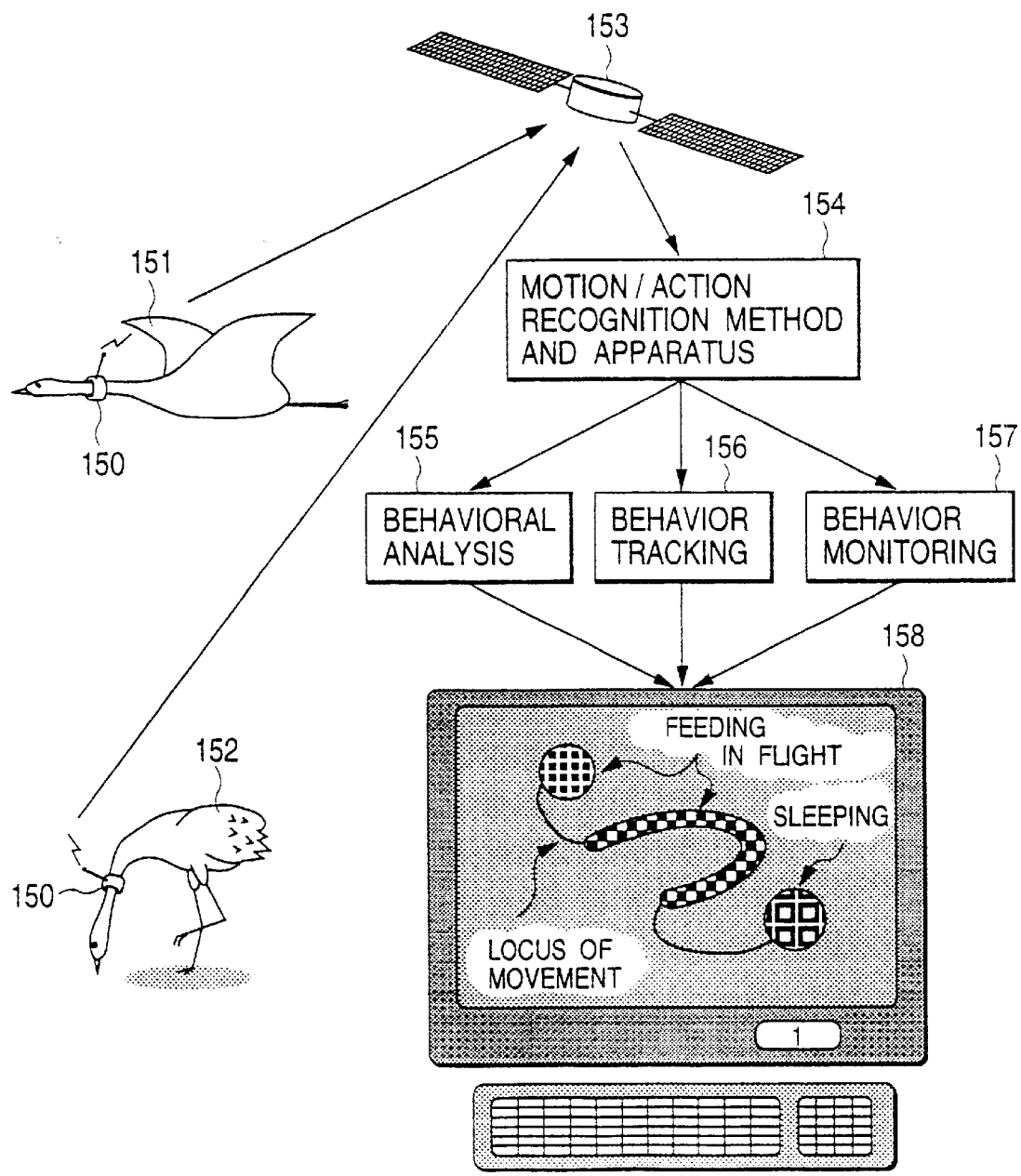
FIG. 21 is an explanatory view of a recognition system applying inventive recognition devices to behavioral analysis, behavior tracking and behavior monitoring.

This recognition system embodying the invention is constituted as shown in FIG. 21. In FIG. 21, reference numerals 151 and 152 stand for birds that are targets to be observed for behavioral analysis, behavior tracking and/or behavior monitoring. Each bird is equipped with a measurement and communication device 150 that measures the bird's status change and transmits the measurements by radio. A satellite 153 receives and forwards measurement data on each bird's status change so as to permit determination of the position from which the bird transmitted the data.

One way of determining a bird's position involves incorporating a GPS receiver in the measurement and communication device 150 of the bird. In operation, behavioral data transmitted from the device 150 to the satellite 153 are accompanied by position data measured by the GPS receiver indicating the current position of the bird. Alternatively, a plurality of satellites 153 may be used to receive radio signals sent from the same bird. The received radio signals are processed through triangulation to determine the bird's position.

The data measured and gathered via satellite 153 are sent illustratively to the motion/action recognition device 154 in FIG. 1. The data are processed to recognize each bird's motion/action in a short period of time. For example, if the bird hardly changes its posture and shows no sign of movement, the bird may be recognized to be asleep; if the bird remains stable in posture but is moving extensively, the bird may be recognized to be in flight; if the bird changes its posture considerably but hardly alters its location, the bird may be recognized to be feeding.

The recognition system constituting this embodiment sends data representing birds' recognized motions and actions to a behavioral analysis unit 155, a behavior tracking unit 156 and a behavior monitoring unit 157. The behavioral analysis unit 155 analyzes each bird's behavior pattern by illustratively ascertaining when the object under observation wakes up, moves, feeds and sleeps. The behavior tracking unit 156 analyzes the loci of movements traced by each bird for its various activities such as feeding. The behavior monitoring unit 157 monitors birds' behavior by grasping where each bird is currently located and what activity each bird is currently engaged in.

Eventually, a display unit 158 such as a CRT gives an overall indication of the analyzed results from the above-mentioned units. A display example in FIG. 21 shows a display of a typical locus of a bird's movement traced by the satellite 153 and superposed with the bird's activities recognized along the way. As illustrated, the display automatically shows when and where each bird exhibited particular aspects of its behavior.

The embodiment of FIG. 21 offers the benefit of permitting automatic observation of the loci of movements traced by objects under observation as well as their behavior, especially in territories inaccessible by humans.

Because there is no need for human observers to make direct visual observation of the object in question, the embodiment of FIG. 21 eliminates possible behavioral aberrations provoked by the presence of the humans in the field. Thus it is possible to observe animals as they act and behave naturally without human intrusion.

Another embodiment of the invention is described below with reference to FIG. 22. This embodiment is a gesture recognition apparatus utilizing an inventive motion/action recognition scheme.

Gestures are defined as predetermined motions with specific meanings. A person transmits a desired meaning by performing the appropriate gesture. In such a case, the performed gesture may or may not represent the conventionally defined meaning associated with the gesture in question. For example, if the motion of "pointing to the right" is predetermined as a gesture which in fact means an "order to go to the left," then an observer interpreting the gesture in this context proceeds to the left accordingly.

Figure 22:
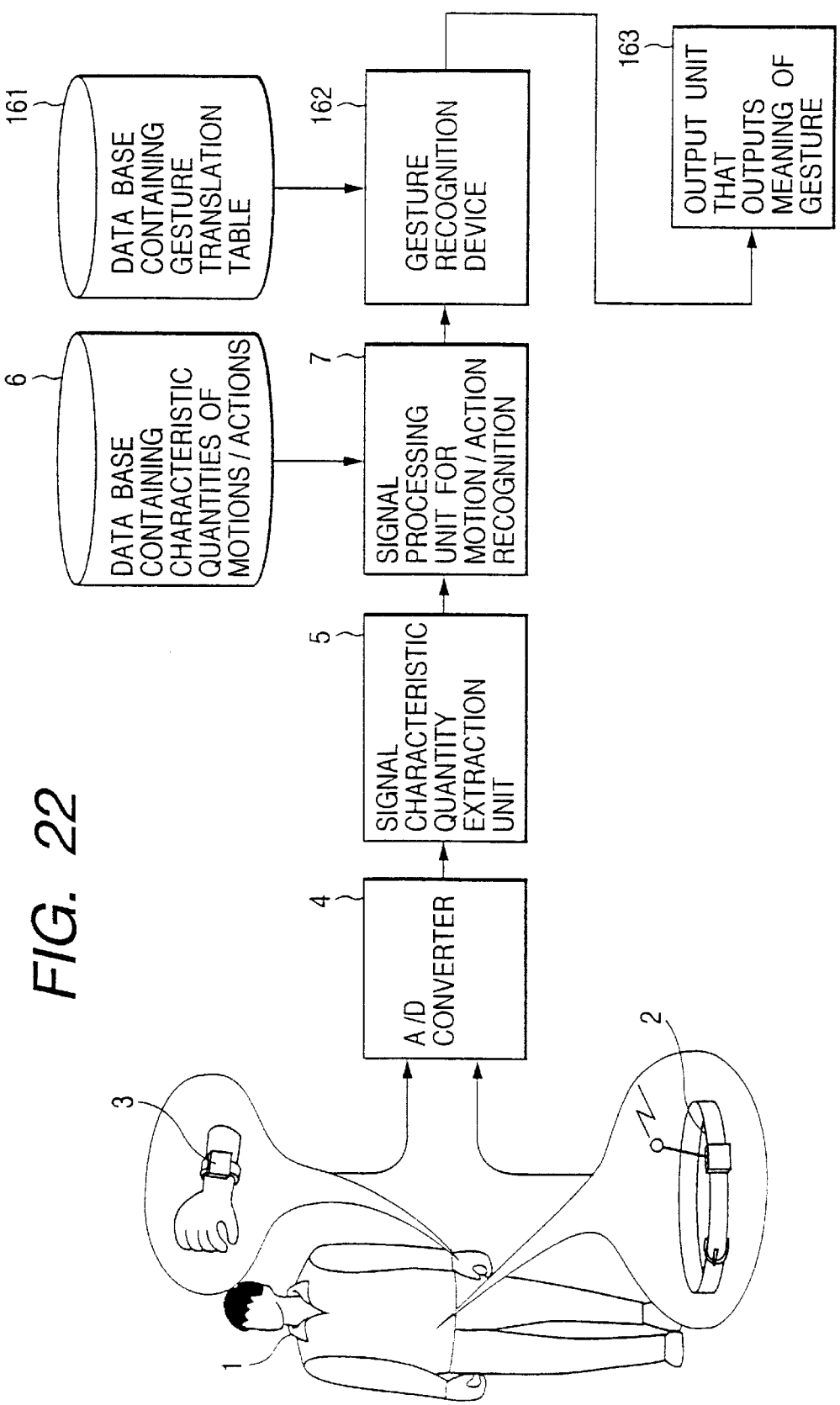
FIG. 22 is a block diagram of a gesture recognition apparatus practiced as another embodiment of the invention.

The embodiment of FIG. 22 is implemented by supplementing the embodiment of FIG. 1 with a database 161 having a translation table defining the correspondence in significance between gestures on one side and motions/actions on the other side, and with a gesture recognition device 162. The gesture recognition device 162 recognizes the meaning of any gesture performed by the object 1 under observation on the basis of the motion/action recognized by the signal processing unit 7 and of the above translation table. The recognized meaning of the gesture is output by an output unit 163.

With this embodiment, the gesture performed by the object 1 is measured by the measuring instruments 2 and 3. The measurement signals are converted by the A/D converter 4 to digital format. The characteristic quantity extraction unit 5 extracts a characteristic quantity from the digitized signals. The characteristic quantity thus extracted from the gesture is sent to the signal processing unit 7 for motion/action recognition. The signal processing unit 7 recognizes the characteristic quantity to be indicative of a conventionally defined motion/action. The recognized result is forwarded to the gesture recognition device 162.

The gesture recognition device 162 recognizes the meaning of the input gesture by referencing the translation table database 161 containing the predetermined meanings of diverse motions/actions. In the example cited above, the motion of "pointing to the right" is defined as the "order to go to the left" according to the translation table. In this manner, the meaning of the recognized gesture is determined and output by the output unit 163.

With the embodiment of FIG. 22 in use, performing a predetermined gesture makes it possible to transmit a specific meaning associated with the gesture in question.

Because the stored gestures are assigned a predetermined meaning each, recognition of a specific gesture eliminates semantic ambiguity conventionally associated with gestures in general.

Another embodiment of the invention is described below with reference to FIG. 23. This embodiment is a motion/action recognition device equipped with radio communication means.

The embodiment of FIG. 23 offers the same effect in terms of recognition capability as the embodiment of FIG. 1. What makes the embodiment different from that in FIG. 1 is that the added radio communication feature transmits by radio the data about the detected status change of the object 1 under observation.

As shown in FIG. 23, the embodiment of FIG. 23 illustratively comprises two major components: a monitored-side device 173 attached to the object 1 under observation, and a monitoring-side device 177. The monitored-side device 173 has a status change measurement unit 171 (equivalent to the measuring instruments 2 and 2 in FIG. 2) attached to the object 1 and a radio transmission unit 172 for transmitting signals measured by the measurement unit 171. The object 1 under observation need only carry two units, i.e., the measurement unit 171 and transmission unit 172. The reduced scale of the equipment to be carried around provides the object with greater freedom of movement than ever before.

A signal 178 to be transmitted by radio may be either a signal (of analog type) directly measured by the status change measurement unit 171 or a digitized signal having undergone analog-to-digital conversion after the measurement. The kind of signals for use with this embodiment may be of electromagnetic radiation or of infrared ray radiation, but is not limited thereto.

The measured result sent to the monitoring-side device 177 is received by a reception unit 174 and recognized by a motion/action recognition device 175. The recognition device 175 illustratively comprises the A/D converter 4, characteristic quantity extraction unit 5, motion/action characteristic quantity database 6, and signal processing unit 7 for motion/action recognition, all included in the setup of FIG. 1. The recognized result from the recognition device 175 is sent to the output unit 176 for output thereby.

The embodiment of FIG. 23 allows measurements taken by the status change measurement unit 171 to be transmitted by radio. This feature enables the object 1 under observation to move more freely and feel less constrained than before.

Another benefit of this embodiment is that the equipment attached to the object under observation is small and lightweight; the attached embodiment consists of only the status change measurement unit and the transmission unit that transmits signals fed from the measurement unit.

Another embodiment of the invention is described below with reference to FIG. 24. This embodiment is a motion/action recognition device according to the invention, supplemented with radio communication means.

The embodiment of FIG. 24 includes a monitored-side device that recognizes the object's motions or actions and radio communication means for sending the recognized result to a monitoring-side device. Those parts of the embodiment which have structurally identical counterparts in the embodiment of FIG. 23 are designated by like reference numerals, and their descriptions are hereunder omitted where redundant.

A signal measured by the status change measurement unit 171 in the monitored-side device 184 is recognized by the motion/action recognition device 175. The recognized result is transmitted by the radio transmission unit 181 to the monitoring-side device 185. The recognized result received by the monitoring-side device 185 is output directly by the output unit 176.

The data 183 transmitted by radio represent the recognized result. As an advantage of this embodiment, the data, compressed considerably from the raw data measured, occupy only a limited radio transmission band or take an appreciably short time when transmitted. In addition, the object 1 may carry around the attached wireless equipment anywhere as desired.

As described and according to the embodiment of FIG. 24, the measurements taken by the status change measurement unit are transmitted by radio. This feature affords the object under observation extended freedom of movement and reduces burdens on the object.

As a further advantage of the embodiment, the amount of data transmitted by radio is compressed so that the data transmission involves a limited radio transmission band, a reduced radio channel occupancy ratio and/or an enhanced transmission speed.

Whereas the embodiments of FIGS. 23 and 24 have adopted the radio transmission means in order to reduce the scale of the equipment to be carried by the object under observation, this is not limitative of the invention. Instead of using the transmission and reception units to implement the radio transmission feature, a variation of the invention may have a portable data storage unit furnished on the monitored side and a data retrieval unit provided on the monitoring side. In such a setup, the portable data storage unit temporarily stores the object's motion data or recognized data about the object's motion. When the object drops in at the observer's place, the observer uses the data retrieval unit to read the data directly from the data storage unit brought in by the object.

Another embodiment of the invention is described below with reference to FIG. 25. This embodiment is a recognition system having an inventive motion/action recognition device supplemented with a prepaid fee handling feature.

Figure 25:
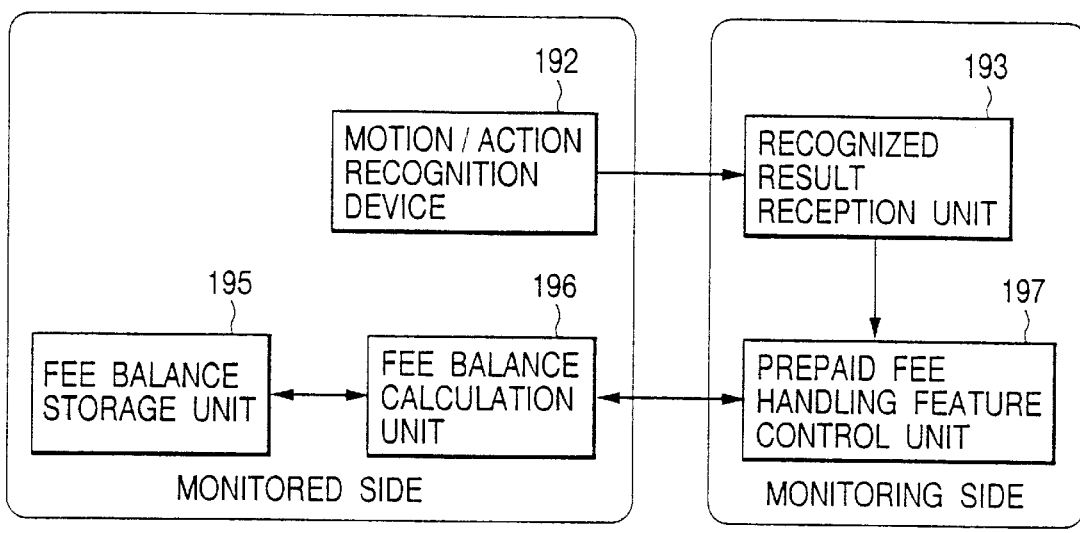
FIG. 25 is a block diagram of a recognition system having an inventive recognition device supplemented with a prepaid fee handling feature to embody the invention.

As shown in FIG. 25, this recognition system embodying the invention comprises, on the monitored side, a recognition device 192 for recognizing the motion/action of the object under observation, a fee balance storage unit 195 for implementing the prepaid fee handling feature, and a fee balance calculation unit 196. On the monitoring side, the recognition system includes a reception unit 193 for receiving the recognized result and a prepaid fee handling feature control unit 197 for outputting a fee balance reduction order, a fee balance verification order and other instructions.

Described below is a typical application of the embodiment in FIG. 25 in an arcade establishment offering games. The motion/action recognition device 192 used in the arcade for inputting a player's gestures may be implemented illustratively by the above-described recognition device of FIG. 1 or 22.

In a game offered by a game machine, a player (object under observation) performs gestures that are recognized by the recognition device 192. The recognized result representing the gestures constitutes orders that are input to the game machine (monitoring-side device) allowing the player to enjoy the game. Illustratively, when the player carries out a given gesture representing a certain trick in "a virtual" fight, a character displayed on the game machine executes the designated trick against his opponent.

A fee settlement scheme is implemented by the embodiment as follows. The equipment on the player's side incorporates the fee balance storage unit 195 and fee balance calculation unit 196. When the player starts playing the game, the recognition device 192 detects the player's starting move and transfers the detected result to the reception unit 193 in the game machine. In the game machine, the prepaid fee handling feature control unit 197 supplies the player's equipment with a fee balance reduction order, a fee balance verification order or other appropriate instructions depending on the game type represented by the data received by the reception unit 193. In the player's equipment, the fee balance calculation unit 196 reduces the fee balance in the fee balance storage unit 195 or performs other suitable operations in accordance with the received orders.

Although not shown, the equipment on the player's side includes warning means that gives a warning to the player when the stored balance in the storage unit 195 drops below a predetermined level. Before playing the game, each player is asked to pay a predetermined fee to the game machine. Paying the fee sets the balance to an initial value in the storage unit 195 before the game is started.

The embodiment of FIG. 25 effectively integrates a gesture input function for playing games and the prepaid fee handling feature associated with the game playing. Thus each player is not required to carry many cumbersome devices in the arcade and can enjoy games there in an unconstrained manner.

Another embodiment of the invention is described below with reference to FIG. 26. This embodiment is a recognition system having an inventive motion/action recognition device supplemented with a credit processing feature. Because the recognition system of FIG. 26 is a variation of the embodiment in FIG. 25, like parts in both embodiments are designated by like reference numerals and their detailed descriptions are hereunder omitted where redundant.

Figure 26:
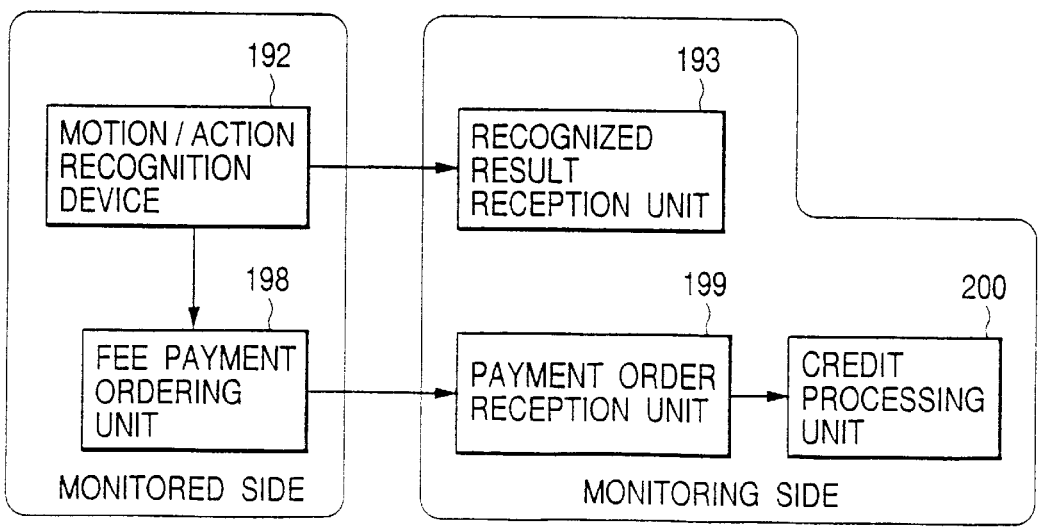
FIG. 26 is a block diagram of a recognition system having an inventive recognition device supplemented with a credit processing feature to embody the invention.

The recognition system of FIG. 26 comprises a motion/action recognition device 192 and a fee payment ordering unit 198 as monitored-side equipment, and includes a recognized result reception unit 193 and a payment order reception unit 199 as monitoring-side equipment. For purpose of illustration, the arcade establishment depicted in connection with the embodiment of FIG. 25 will again be referenced as an application of the embodiment in FIG. 26.

With this embodiment, the equipment attached to the player incorporates a credit card processing feature. When the player plays a game, the recognition device 192 recognizes the type of the game and causes the fee payment ordering unit 198 to issue a fee payment order reflecting the recognized result. The payment order is received by the reception unit 199 on the monitoring side. Given the order, the reception unit 199 causes a credit processing unit 200 to present the applicable credit company with the fee to be credited together with the player's credit card number.

The embodiment of FIG. 26 thus effectively integrates the gesture input function for playing games and the credit processing feature. Thus each player is not required to carry many cumbersome devices in the arcade and can enjoy games there in an unconstrained manner.

Another embodiment of the invention is described below with reference to FIG. 27. This embodiment is a recognition system having an inventive motion/action recognition device supplemented with a deposit handling feature. Those parts of the embodiment having their structurally identical counterparts in the embodiment of FIG. 25 are designated by like reference numerals, and their detailed descriptions are hereunder omitted where redundant.

Figure 27:
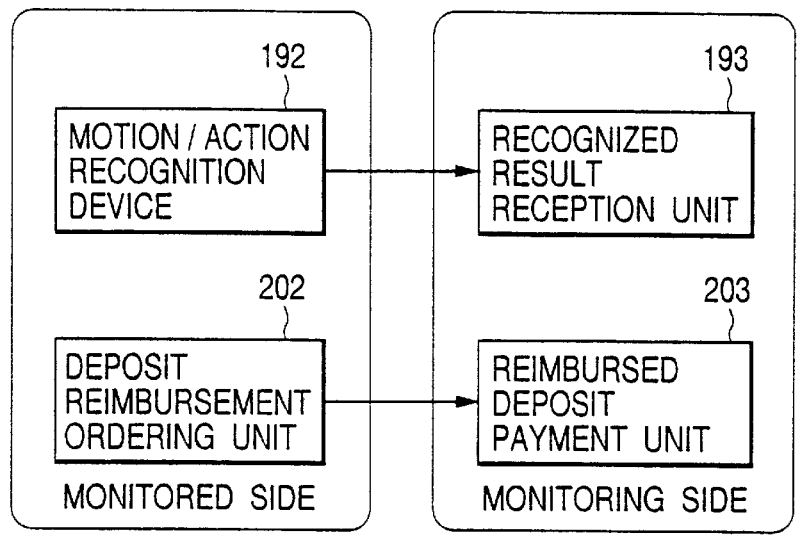
FIG. 27 is a block diagram of a recognition system having an inventive recognition device supplemented with a deposit handling feature to embody the invention.

The recognition system of FIG. 27 comprises a motion/action recognition device 192 and a deposit reimbursement ordering unit 202 as monitored-side equipment, and includes a recognized result reception unit 193 and a reimbursed deposit payment unit 203 as monitoring-side equipment. Again for purpose of illustration, the arcade establishment depicted in connection with the embodiment of FIG. 25 will be referenced here as an application of the embodiment in FIG. 27.

As an example, suppose that players rent out gesture input devices (i.e., recognition devices 192), play games and return the devices after enjoying the games. In such cases where part of the playing equipment is rented out to customers, the rate of equipment recovery is raised if penalties are imposed on missing rented devices. One typical strategy for ensuring the return of the rented equipment is a deposit scheme. The system embodying the invention in FIG. 27 supports a deposit scheme wherein each player, when renting out the gesture input device 192, deposits a predetermined sum of money with the establishment and gets the deposit reimbursed upon returning the rented gesture input device 192.

With this system, the player rents out the gesture input device 192 and leaves the predetermined deposit with the monitoring side. When the gesture input device 192 is returned, the deposit reimbursement ordering unit 202 carried by the player together with the gesture input device 192 sends a deposit reimbursement order to the reimbursed deposit payment unit 203 on the monitoring side. Given the order, the reimbursed deposit payment unit 203 returns the deposit to the player.

As described, the embodiment of FIG. 27 offers the benefit of raising the return rate of rented motion/action recognition devices.

The recognition system embodying the invention in FIG. 27 may be applied, but not limited, to two kinds of equipment: an automatic renting apparatus which accommodates a plurality of gesture input devices and which rents out one of them every time it receives a predetermined sum of money as a deposit; and an automatic device recovery apparatus which, upon receiving a rented gesture input device, pays out the same sum of money as the predetermined deposit.

Another embodiment of the invention is described below with reference to FIG. 28. This embodiment is a recognition system having an inventive motion/action recognition device supplemented with an entry/exit verification feature for checking any entry into or exit from a designated area by an object. Those parts of the embodiment having their structurally identical counterparts in the embodiment of FIG. 25 are designated by like reference numerals, and their detailed descriptions are hereunder omitted where redundant.

Figure 28:
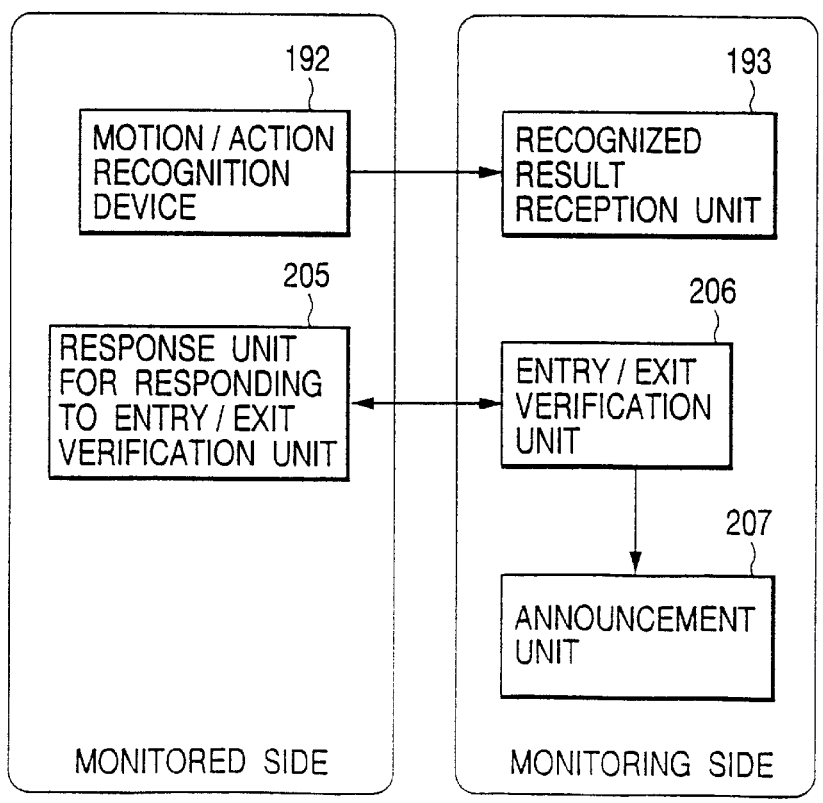
FIG. 28 is a block diagram of a recognition system having an inventive recognition device supplemented with an entry/exit verification feature to embody the invention.

The recognition system embodying the invention in FIG. 28 comprises a motion/action recognition device 192 and a response unit 205 for responding to an entry/exit verification unit as monitored-side equipment, and includes a recognized result reception unit 193, an entry/exit verification unit 206 and an announcement unit 207 as monitoring-side equipment. Again for purpose of illustration, the arcade establishment depicted in connection with the embodiment of FIG. 25 will be referenced here as an application of the embodiment in FIG. 28.

Suppose that players rent out gesture input devices (part of the monitored-side equipment), play games and return the devices after enjoying the games. In such cases where the recognition devices 192 are rented out and then returned, the recovery rate of rented equipment is raised if the players are presented on suitable occasions with an announcement urging them to return the equipment. For example, a player exiting from the designated game area to go somewhere else is given a warning if he or she still carries the rented gesture input device that has been detected. Such a scheme is implemented automatically by the embodiment of FIG. 28.

The gesture input device incorporates the gesture recognition device 192 and the response unit 205 for responding to an entry/exit verification unit. Incidentally, the entry/exit verification unit 206 furnished on the monitoring side emits radio signals that cover a very limited area.

When a player tries to leave the game area while still carrying the gesture input device, the response unit 205 receives a signal from the entry/exit verification unit 206 located on the boundary of the area. The response unit 205 returns a response signal to the verification unit 206. Given the response signal, the verification unit 206 senses that the player is on the point of leaving the game area while still carrying the rented gesture input device. The sensed result is forwarded to the announcement unit 207 that gives a warning to the player in question.

As described, the embodiment of FIG. 28 offers the benefit of raising the recovery rate of rented motion/action recognition devices in a delimited area.

The following is description of an example of recognition of actions taken by an object under observation by taking a cyclical motion as an example.

Figure 47A:
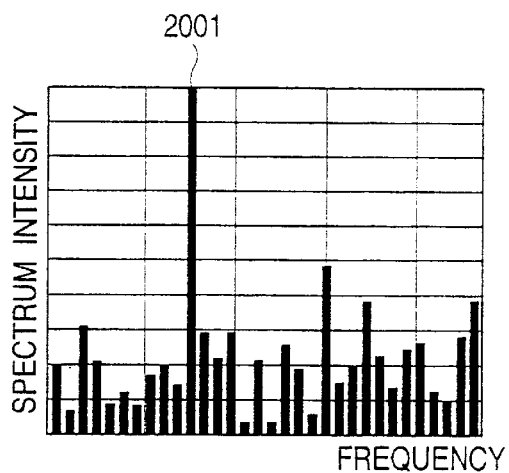
FIG. 47 are explanatory diagrams showing a method of extracting a gait cycle which serves as a fundamental of the recognition of a cyclical motion.
Figure 47B:
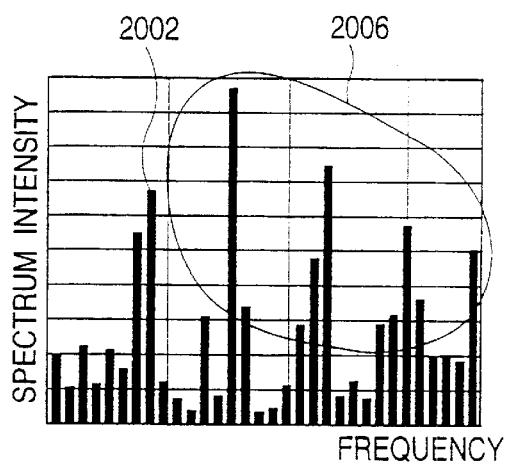
Figure 47C:
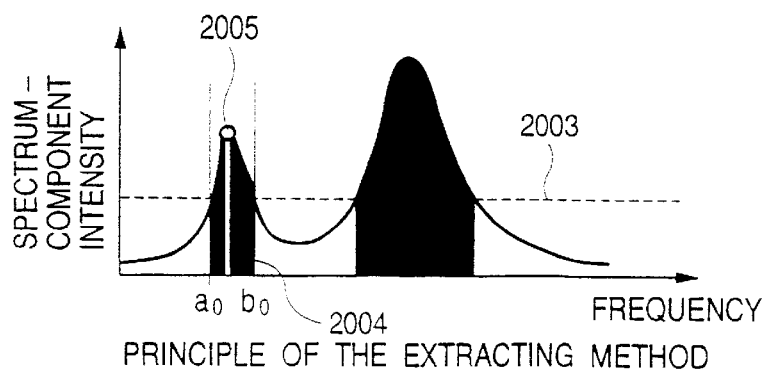

FIG. 47 are explanatory diagrams showing a method of extracting a gait cycle which serves as a fundamental of the recognition of a cyclical motion. A gait cycle is a period of time between two consecutive heel contacts of the same leg with the surface of the earth. A heel contact is defined as a moment at which the heel of a foot is stepped on the earth. If the right and left legs are moved at the same speed, a gait cycle is a time it takes to move forward by two steps. FIG. 47 are diagrams each showing a spectrum of an acceleration signal in the vertical direction of the motion of a human body obtained as a result of observation carried out for a variety of walking speeds and walking conditions, from a slowly walking state to a running state. To be more specific, FIG. 47A and FIG. 47B are diagrams showing frequency spectra for a normally walking state and a slowly walking state respectively. In the case of normal walking and running states, a spectrum exhibiting a very strong component 2001 at a frequency corresponding to the gait cycle like the one shown in FIG. 47A is obtained. Results of the observation also indicate that, in the case of an extremely slow walking state with a gait cycle equal to or greater than about 1.5 seconds, that is, in the case of a walk with dragging feet, the spectrum may exhibit a strong component other than the predominant component at a frequency corresponding to the gait cycle which is also referred to hereafter as a gait-cycle frequency. It should be noted that the average gait cycle of healthy people is 1.03 seconds whereas the average gait cycle of elderly people is 1.43 second. In addition, in an extreme case, the spectrum exhibits other predominant components 2006 which are even stronger than the predominant component 2002 at a frequency corresponding to the gait cycle like the one shown in FIG. 47B. It is worth noting that the spectra shown in FIGS. 47A and 41B have each been obtained by normalizing the intensities (or the powers) of all the components except the direct-current component by the maximum spectrum intensity (power). Fortunately, results of the observation also indicate that, in the observed walking and running motions with a gait cycle in the range 0.35 to 2.0 seconds which correspond to the running and slowly walking states respectively, there is no spectrum exhibiting a strong component at a frequency lower than the gate-cycle frequency, making the following processing procedure conceivable. The following is description of the processing procedure for finding the gait-cycle frequency and the intensity (or the power) of a spectrum component at the gait-cycle frequency from a spectrum representing a motion with reference to FIG. 47C.

(1) The average value T (denoted by reference numeral 2003) of the powers of all spectrum components excluding the direct-current component (that is, the 0th-order harmonic) is found by using the following equation:

$$T = \frac{\sum_{n=1}^{m} P(n)}{m}$$

where notation m denotes the highest order of the harmonics and notation P(n) is the power of the nth-order harmonic of the spectrum.

(2) In order to extract only components each with a power greater than the average value T, frequency ranges $(a_i, b_i)$ that satisfy a condition represented by the following relations are identified:

$n \neq 0$ and $P(n) > T$

The above relation indicates that the powers P(n) of all spectrum components except the direct-current component in each of the frequency ranges $(a_i, b_i)$ are greater than the average value T 2003.

The average value T of the spectrum power is taken as a threshold value as described above, because, the power at the gate cycle and other powers both vary in dependence on the type of the motion so that there may be a case in which the power at the gate-cycle frequency can not be extracted if the threshold is set at a fixed value.

It should be noted that, while the average value T is taken as a threshold value in the present embodiment, the description is not to be construed in a limiting sense. For example, instead of using the average value T as a threshold value, processing making use of a product of the average value T and a predetermined coefficient as a threshold value is also conceivable.

(3) A lowest-frequency range $(a_0, b_0)$, a frequency range (where i=0) at lowest frequencies among the frequency ranges $(a_i, b_i)$ found in the above step (2), is identified and a maximum power P(j) and the frequency j of a spectrum component having the maximum power P(j) in the lowest-frequency range $(a_0, b_0)$ are found. It should be noted that the maximum power P(j) and the frequency j are denoted by reference numerals 2005 and 2004 respectively in FIG. 47C. The maximum power P(j) is expressed by the following equation:

$S = P(j) = \max[P(a_0), P(b_0)]$ where notation S is the power of a spectrum component at a gait-cycle frequency j. That is to say, the frequency j and the power P(j) found by using the procedure described above are the gait-cycle frequency and the power of a spectrum component at the gait-cycle frequency respectively. The frequency j is defined as the number of steps per second. As described above, the gait cycle Gc is composed of two steps. Thus, the length of the gate cycle Gc can be found by using the following equation:

$G_c = 2/j$

As described above, FIGS. 47A and 47B are spectra from which gait-cycle frequencies 2001 and 2002 respectively are extracted. Comparison of results of measurements using a stop-watch with results obtained from the processing procedure described above for gait cycles in the range 0.35 to 2.0 seconds indicates that the former approximately matches the latter.

Figure 48A:
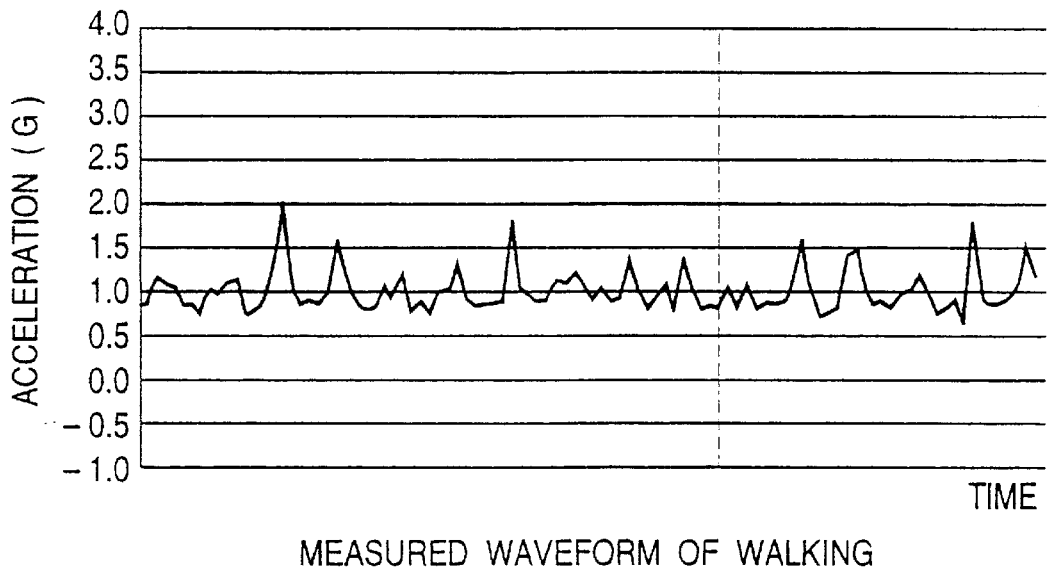
FIGS. 48A and 48B are diagrams showing waveforms obtained as results of observation of normal-walking and normal-running states respectively.
Figure 48B:
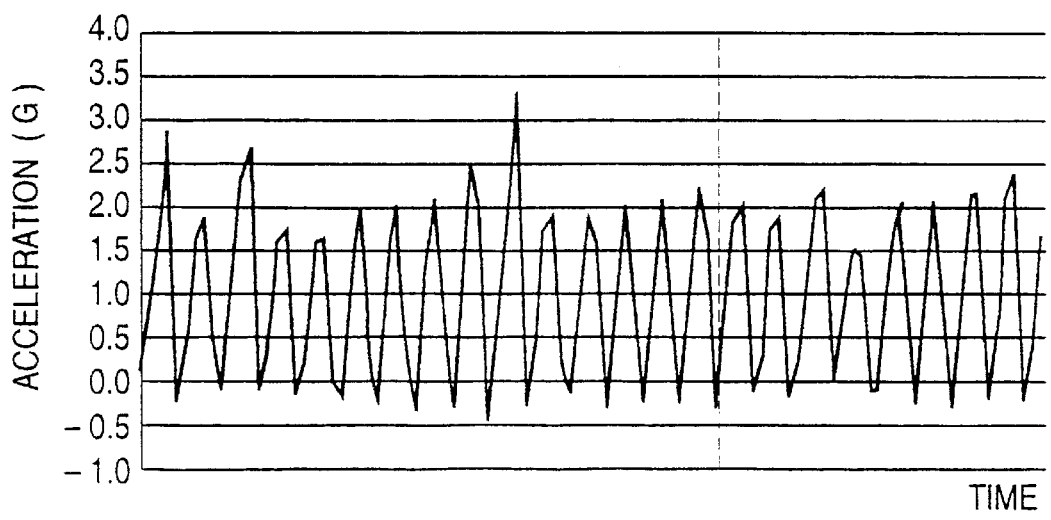

The difference between the walking and running states is that, in the case of the latter, there are periods of time in which both feet are separated from the surface of the earth simultaneously. At the beginning of a period of free-fall drops of both the feet from a state of being separated from the surface of the earth toward the earth, an acceleration sensor attached to the human body indicates a measured acceleration value of 0 G. That is to say, the measurement result indicates probably a state of almost no gravitational force. Thus, by forming a judgment as to whether or not a state of no gravitational force exists, the recognition of the difference between the walking and running states is considered to be possible. Waveforms obtained as results of observation of normal walking and normal running states are in FIGS. 48A and 48B respectively. In the case of walking shown in FIG. 48A, a graph shows variations in acceleration with an amplitude of about 0.3 G centering on a gravitational-force acceleration of 1.0 G. It is obvious from the figure that the minimum value of the acceleration experienced by the human body is about 0.7 G, indicating that the state of no gravitational force does not exist. In the case of running shown in FIG. 48B, on the other hand, a graph shows variations in acceleration with an amplitude increased to about 1.0 G and the existence of states of no gravitational force, that is, states of a 0.0 G gravitational force. In order to form a judgment as to whether or not a state of no gravitational force exists, the power of a spectrum component at the gait-cycle frequency found by using the processing procedure described above can be used to represent the amplitude of the variations in acceleration to be compared with a criterion which is 1.0 G as shown in FIG. 48B. This is because, in a running state, the variations in acceleration-signal amplitude can be represented by a sinusoidal curve having a frequency equal to the gait-cycle frequency. Thus, the power of the sinusoidal spectrum component at the gait-cycle frequency just corresponds to the value of the amplitude of the acceleration signal having a frequency matching the gait-cycle frequency. In actuality, however, the power of the spectrum component at the gait-cycle frequency does not perfectly correspond to the value of the amplitude of the acceleration signal due to a sampling relation between the width of a window function for carrying out the FFT processing and the gait cycle, effects of discrepancies between the variations in acceleration and the sinusoidal curve and effects of the inertia force of an infinitesimal weight in the acceleration sensor. For this reason, instead of the amplitude 1.0 G shown in FIG. 48B, a gait-cycle amplitude of 0.8 G is used as a criterion as to whether the motion is walking or running. Paying attention to the fact that the power of a spectrum component at the gait-cycle frequency can be used as a value to be compared with a criterion in a judgment on transitions from the a rest, to walking and then to running, the state of a motion is recognized by using such a spectrum-component power. Of course, a judgment as to whether or not a state of no gravitational force exists can be formed by finding a minimum acceleration value of a measured acceleration waveform as is obvious from FIG. 48B. In this case, however, it is necessary to consider a problem of incorrect recognition due to noise.

Figure 49:
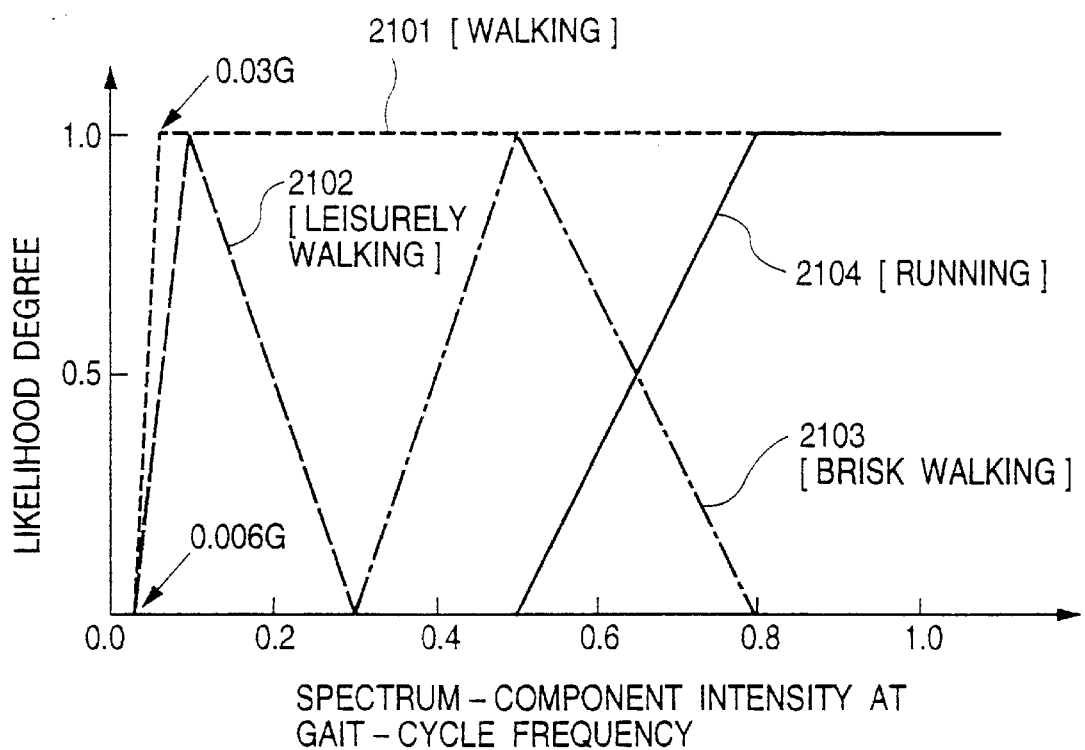
FIG. 49 is a diagram showing relations between the power of a spectrum component at the gait-cycle frequency and the degree of recognition likelihood of each recognition item.

A result of an observation of transitions to brisker motions, that is, from a rest state, to a walking state and then to a running state, indicates that the recognized power of a spectrum component at the gait-cycle frequency increases, accompanying such transitions of motion. For this reason, instead of recognizing the state of either walking or running as a binary value, an attempt has been made to recognize the state of either walking or running by dividing it into fine states with the power of a spectrum component at the gait-cycle frequency taken as an indicator. FIG. 49 is a diagram showing relations between the power of a spectrum component at the gait-cycle frequency and the degree of recognition likelihood of each recognition item, an indicator as to how likely the recognition of the recognition item is. The vertical and horizontal axes of the figure respectively represent the degree of recognition likelihood and the power of a spectrum component at the gait-cycle frequency which is expressed in terms of gravitational-force units (G) because the power of a spectrum component at the gait-cycle frequency corresponds to the amplitude of an acceleration signal representing by the spectrum. By a recognition item, the state of a motion such as the rest, slowly-walking, walking, briskly-walking or running state is meant. As shown in the figure, the likelihood degree $W_n$ of each recognition item is a function of S, the power of a spectrum component at the gait-cycle frequency. The value of the degree of recognition likelihood can be any arbitrary value in the range 0 to 1 for a possible value $S_u$ of the power of a spectrum component at the gait-cycle frequency as expressed by the following with the limit values 0 and 1 respectively indicating the minimum likelihood representing a least likely possibility and the maximum likelihood representing a most likely possibility:

$$W_n : S_u \rightarrow <0, 1>$$

Thereafter, the function is used as a performance function. There are two types of performance function in use. A performance function of the first type is a walking performance function or a running performance function used for evaluating the state of a motion as walking or running respectively. The walking performance function and the running performance function are shown by a dotted-line curve 2101 and a solid-line curve 2104 respectively in FIG. 49. As shown in the figure, according to the first type of performance function, if the power of a spectrum component at the gait-cycle frequency is greater than a criterion, then the state of a motion is judged to be walking in the case of a walking performance function or running in the case of a running performance function at a degree of recognition likelihood of 1. The performance function Wstep of the first type is expressed as follows:

$$\begin{aligned} W_1(S{:}a, b) &= 0 && \text{for } S < a \\ &= (S/(b-a) - a/(b-a)) && \text{for } a \leq S \leq b \\ &= 1 && \text{for } S > b \end{aligned}$$

A performance function of the second type is a leisurely-walking performance function or a brisk-walking performance function used for evaluating the state of a motion as leisurely walking or brisk walking respectively. The leisurely-walking performance function and the brisk-walking performance function are shown by a dashed-line curve 2102 and a dotted-dashed-line curve 2103 respectively in FIG. 49. As shown in the figure, according to the second type of performance function, at a certain value of the power of a spectrum component at the gait-cycle frequency, the degree of recognition likelihood reaches a peak value of 1, that is, the state of a motion is judged to be leisurely walking in the case of a leisurely-walking performance function or brisk walking in the case of a brisk-walking performance function at a degree of recognition likelihood of 1. The performance function Wpeak of the second type is expressed as follows:

$$\begin{aligned} W_b(S{:}a, b, c) &= 0 && \text{for } S < a \\ &= (S/(b-a) - a/(b-a)) && \text{for } a \leq S \leq b \\ &= (S/(b-c) - c/(b-c)) && \text{for } b \leq S \leq c \\ &= 1 && \text{for } S > c \end{aligned}$$

The values of the values of the parameters a, b and c used as criteria are determined by observing conditions of some normally healthy people under observation. The horizontal and vertical axes of the curves shown in FIG. 48 represent the power of a spectrum component at the gait-cycle frequency and the degree of recognition likelihood respectively. States of motion to be recognized are a rest, walking and running. In addition, the state of a motion referred to as leisurely walking represents the degree of a process of a transition from a rest to normal walking whereas the state of a motion referred to as brisk walking represents the degree of a process of a transition from a normal walking to running to give a total of five states of motion.

The state of a rest is recognized when the power of a spectrum component at the gait-cycle frequency is found to have a value equal to or smaller than 0.006 G. This is because, the maximum power of acceleration spectrum components measured in a rest state is about 0.004 G. If the value 0.004 G were used as a threshold, a rest would probably be recognized incorrectly as walking due to the power of noise added to the power of a spectrum component at the gait-cycle frequency in the rest state to result in a value greater than 0.004 G. Thus, the threshold value 0.006 G guarantees that there is no way that a rest state is recognized incorrectly as walking by the processing.

The state of walking is recognized as the power of a spectrum component at the gait-cycle frequency exceeds the threshold value 0.006 G of the rest state described above with the degree of recognition likelihood linearly increasing with the power of a spectrum component at the gait-cycle frequency. The degree of recognition likelihood reaches a maximum value of 1 as the power of a spectrum component at the gait-cycle frequency increases to 0.03 G, staying flat thereafter as shown by the graph 2101. Here, as indicated by the graph 2101, walking is defined as a state of all motions including even running. Accordingly, when the state of a cyclical motion other than a rest (that is, walking) is recognized, the degree of recognition likelihood of walking is greater than 0. It should be noted that a value slightly greater than 0 corresponds to very slowly walking with a gait cycle of 2.0 seconds. As the walking motion further enters a state in which the human body moves up and down to the utmost, the power of a spectrum component at the gait-cycle frequency increases to 0.03 G. Fuzzy-state processing is therefore carried out for an ambiguous state between a rest with the power of a spectrum component at the gait-cycle frequency having a value equal to 0.006 G and a walking state with the degree of recognition likelihood having a value equal to 1.0 and the power of a spectrum component at the gait-cycle frequency having a value increased to 0.03 G. This state of walking in the range 0.006 G to 0.03 G is a fuzzy or ambiguous state. As a matter of fact, all slanting line segments shown in FIG. 49 represent a fuzzy state. The walking performance function Wwalk for such fuzzy-state processing is denoted by the following symbol:

$W_{walk}(S:0.006, 0.03)$

As indicated by the graph 2102, the degree of recognition likelihood of leisurely walking linearly increases from 0 at the threshold value of the rest state and reaches a peak value of 1.0 as the power of a spectrum component at the gait-cycle frequency becomes equal to 0.1 G. Thereafter, the degree of recognition likelihood linearly decreases from the peak value 1.0 and reaches the bottom value 0 as the power of a spectrum component at the gait-cycle frequency increases to 0.3 G. This graph 2102 is drawn to show criteria of 0.1 G and 0.3 G because, when the object under observation walks slowly, the power of a spectrum component at the gait-cycle frequency is found to be 0.1 G and, when the object walks normally, the power of a spectrum component at the gait-cycle frequency is found to be 0.3 G. The leisurely-walking performance function Wleisurely for such fuzzy-state processing is denoted by the following symbol:

$W_{leisurely}(S:0.006, 0.1, 0.3)$

As indicated by the graph 2103, the degree of recognition likelihood of brisk walking linearly increases from 0 at the normal walking with the power of a spectrum component at the gait-cycle frequency having a value equal to 0.3 G and reaches a peak value of 1.0 as the power of a spectrum component at the gait-cycle frequency becomes equal to 0.5 G. Thereafter, the degree of recognition likelihood linearly decreases from the peak value 1.0 and reaches the bottom value 0 as the power of a spectrum component at the gait-cycle frequency increases to 0.8 G. This graph 2103 is drawn to show criteria of 0.5 G and 0.8 G much like the graph 2102 representing the leisurely walking because, when the object under observation walks fast, the power of a spectrum component at the gait-cycle frequency is found to be 0.5 G and, when the object enters a running state, the power of a spectrum component at the gait-cycle frequency is found to be 0.8 G. The brisk-walking performance function Wbrisk for such fuzzy-state processing is denoted by the following symbol:

$W_{brisk}(S:0.3, 0.5, 0.8)$

As indicated by the graph 2104, the state of running is recognized as the power of a spectrum component at the gait-cycle frequency exceeds the value 0.5 G with the degree of recognition likelihood linearly increasing with the power of a spectrum component at the gait-cycle frequency. The degree of recognition likelihood reaches a maximum value of 1 as the power of a spectrum component at the gait-cycle frequency increases to 0.8 G, staying flat thereafter. The graph 2104 is drawn to show a criterion of 0.8 G because a very-slow-running state in which there are times both feet are separated from the surface of the earth has been observed when the power of a spectrum component at the gait-cycle frequency reaches the value 0.8 G. As described earlier, the value 0.8 G is a criterion used in forming a judgment as to whether or not a state of no gravitational force exists. The running performance function Wrun for such fuzzy-state processing is denoted by the following symbol:

$W_{run}(S:0.5, 0.8)$

The state of a motion is recognized by evaluation of the degree of recognition likelihood of the motion by substituting the value of the power of a spectrum component at the gait-cycle frequency to the expression of the performance function for the motion. When the value of the power of a spectrum component at the gait-cycle frequency is observed to be 0.6 G, for example, the degree of recognition likelihood for walking is found from the graph 2101 shown in FIG. 49 to be 1.0, a value indicates a walking state including running. To be more specific, the object under observation is in a state of motion with a degree of brisk-walking likelihood of 0.67 and a degree of running likelihood of 0.33 according to the graphs 2103 and the graph 2104 respectively and is no way in a state of leisurely walking.

In addition, the gradient of a human body, that is, the state of the upright/leaning posture of the human body, can be recognized from an average value of variations in acceleration observed by an acceleration sensor. The acceleration sensor is used for measuring variations in acceleration in one axis direction on the structure thereof. Specifically, with an angle of gradient formed by the sensitivity direction of the acceleration sensor and the gravitational-force direction set at 0 degree, that is, at an angle of gradient wherein the sensitivity direction of the acceleration sensor coincides with the gravitational-force direction, an acceleration of 1.0 G, an average value equal to the gravitational-force acceleration, is observed. As the angle of gradient is increased, however, the observed average acceleration gradually decreases in all but inverse proportion to the angle of gradient. When the sensitivity direction of the acceleration sensor is finally oriented perpendicularly to the gravitational-force direction, that is, when the angle of gradient formed by the sensitivity direction of the acceleration sensor and the gravitational-force direction is set at 90 degrees, the gravitational-force acceleration is no longer observed. Thus, in a rest state, the gradient of the acceleration sensor (that is, the gradient of the human body) can be measured from the observed average value of the acceleration. Even with the human body put in motion, if the human body is assumed to experience no acceleration due to an external force other than the gravitational force, the time-axis average of observed values of the acceleration can be regarded as the gravitational-force acceleration. Thus by calculating the ratio of a calculated average value of observed variations in acceleration to the gravitational-force acceleration 1.0 G, the gradient of the human body can be found. The average value of observed variations in acceleration is output as the magnitude of a direct-current component (the 0th-order harmonic) of a spectrum resulting from a frequency analysis. The magnitude of the direct-current component is used to find the gradient of the human body which is, in turn, utilized for forming a judgment on the state of the upright/leaning posture of the human body.

In the case of the example described above, the method of recognition provided by the present invention results in a degree of brisk-walking likelihood of 0.67 and a degree of running likelihood of 0.33. By merely looking at such numbers, none the less, it is still difficult for the observer to know what motion the body of the object under observation is put in. In order to solve this problem, there is provided an embodiment implementing a method of expressing results of recognition of a motion not in terms of numbers or words but by animation using CG (computer graphics) which can be understood by the observer intuitively with ease.

Figure 30:
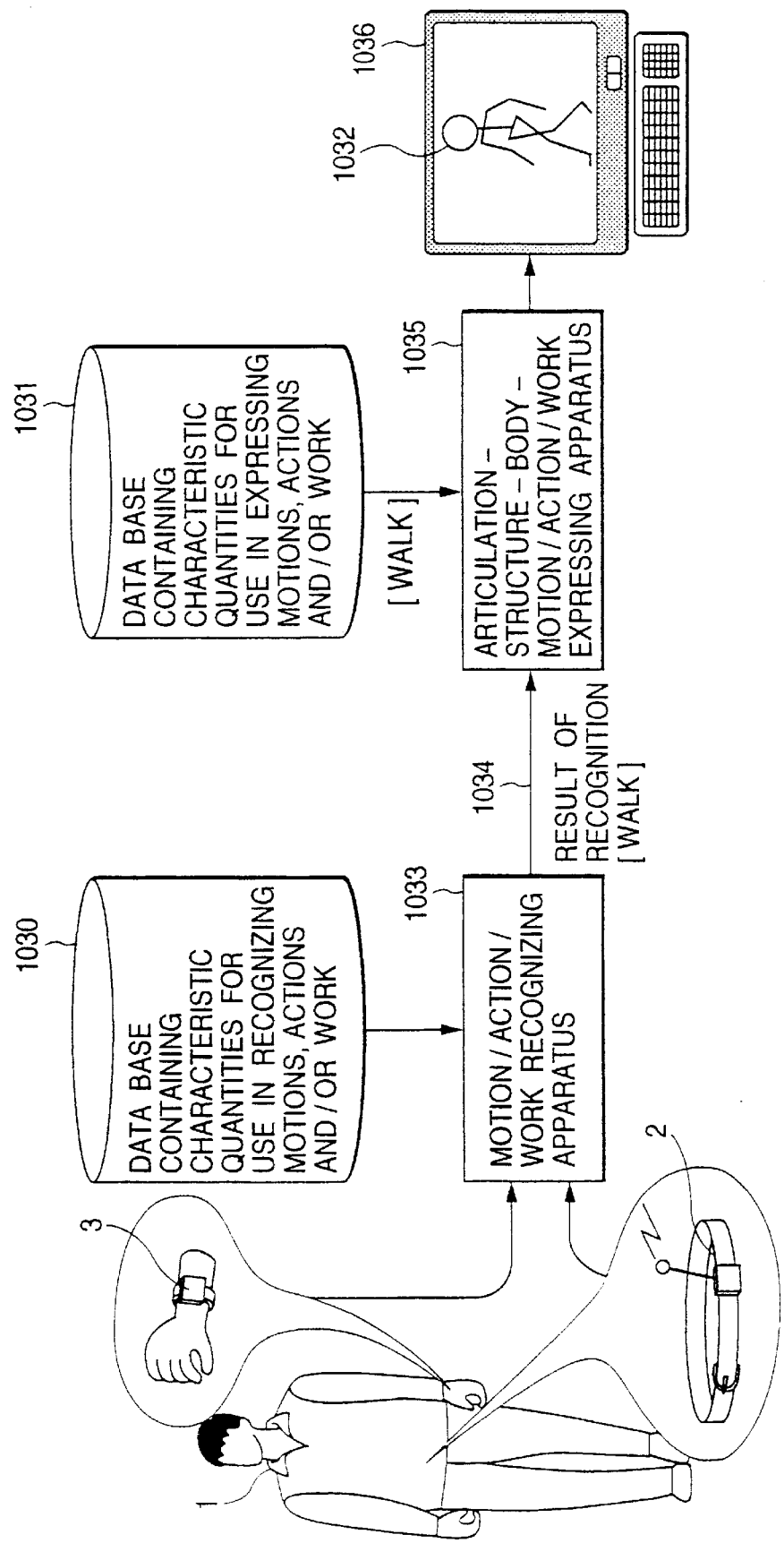
FIG. 30 is a diagram showing the configuration of a system for displaying results, which are obtained from observation of a motion, an action and/or work of an object under observation by using a motion/action/work recognizing apparatus, by animation using computer graphics as a method of expressing motions, actions and/or work of an articulation-structure body.

FIG. 30 is a diagram showing the configuration of a system for displaying results, which are obtained from observation of a motion, an action and/or work of an object under observation by using a motion/action/work recognizing apparatus, by animation using computer graphics as a method of expressing motions, actions and/or work of an articulation-structure body.

As shown in the configuration diagram, the system comprises: measurement instruments 2 and 3 attached to an object under observation 1; a motion/action/work recognizing apparatus 1033 for recognizing the motion, the action and/or the work of the object under observation on the basis of results measured by the measurement instruments 2 and 3; a first data base 1030 containing characteristic-quantity data for use in recognizing the motion, the action and/or the work; an articulation-structure-body-motion/action/work expressing apparatus 1035 for expressing motions, actions and/or work of an articulation-structure body derived from a result of recognition 1034 as a two-dimensional or three-dimensional image; a second data base 1031 containing characteristic-quantity data for use in expressing the motion, the action and/or the work; and an output unit 1032 for displaying the two-dimensional or three-dimensional image.

First of all, results of measurements are transmitted by the measurement instruments 2 and/or 3 attached to the object under observation 1 to the motion/action/work recognizing apparatus 1033. The results are then compared with characteristic quantities stored in the first data base 1030 to output the result of recognition 1034. It should be noted that, in general, a characteristic quantity of a motion corresponds to the power (intensity) of a spectrum component at the gait-cycle frequency for the motion, that is, corresponds to the amplitude of the acceleration signal representing the motion. In this example, the result of recognition indicates that the object under observation 1 is in a state of walking. The result of recognition 1034 is then supplied to the articulation-structure-body-motion/action/work expressing apparatus 1035 for expressing motions, actions and/or work of an articulation-structure body. In this example, the articulation-structure body is the object under observation.

The articulation-structure-body-motion/action/work expressing apparatus 1035 retrieves characteristic quantities for the result of recognition 1034 output by the motion/action/work recognizing apparatus 1033 from the second data base 1031. The characteristics quantities are used for generating information on the motion of the articulation-structure body which is finally supplied to the output unit 1032 as animation.

A method of expressing the motion of a human being in accordance with characteristics of the motion by using computer graphics is disclosed in a thesis magazine with a title "Generation of Human Walking Motion with Emotion for Computer Animation" published by the Academic Society of Electronic, Information and Communication Engineers, D—II, Vol. J76-D-II, No. 8, pp. 1822 to 1831, August 1993, and in U.S. Pat. No. 5,483,630. These references describe a method for expressing a variety of motions by animation using computer graphics whereby, from various kinds of walking behavior of human beings, characteristic quantities expressing characteristics of all kinds of walking behavior are extracted and then, by synthesizing a variety of extracted characteristic quantities and controlling the strength (the weight) of each characteristic quantity, a variety of motions can be expressed by animation using computer graphics. It should be noted that the strength (weight) of a characteristic quantity in general corresponds to the degree of recognition likelihood of the motion represented by a spectrum whose component power at the gait-cycle frequency corresponds to the characteristic quantity.

The present invention provides a novel method based on the method disclosed in the above references. The method provided by the present invention is used for expressing a variety of motions by animation using computer graphics in accordance with characteristics of the recognized motions.

To be more specific, the inventors of the present invention use the method disclosed in the above references, allowing a variety of cyclical motions to be generated by controlling the characteristic quantities of the motions. An outline of processing to generate such cyclical motions is described in brief as follows.

Figure 31:
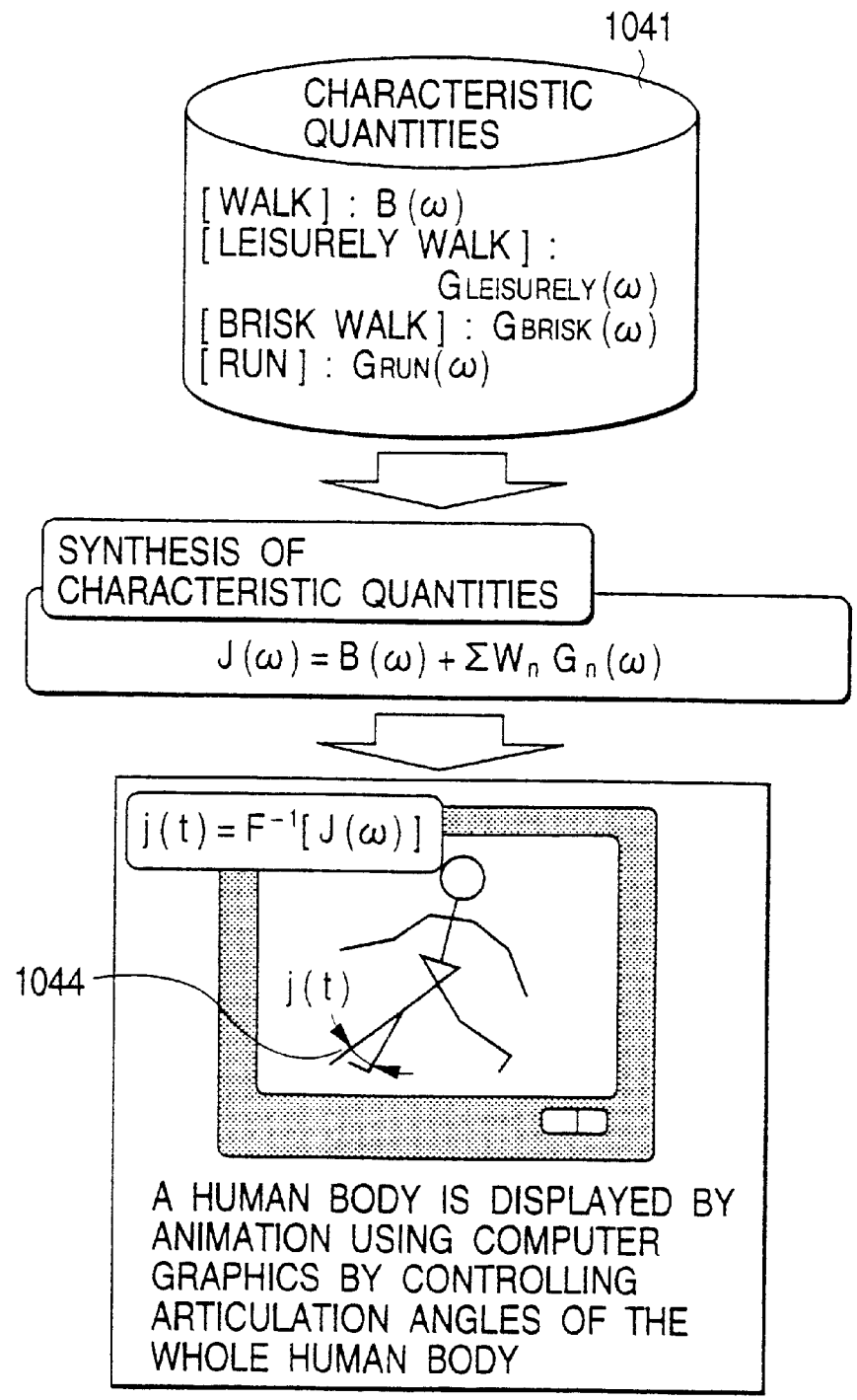
FIG. 31 is a skeleton explanatory diagram showing a method of expressing a motion, an action and/or work of an articulation-structure body by using the characteristic quantities of the motion, the action and/or work.

FIG. 31 is a skeleton diagram showing a method of expressing a motion of a human being by using the characteristic quantities of the motion. In particular, the figure is used for explaining an example of generating the motion of the joint of a right knee 1044 as a function j(t). It should be noted, however, that motions of other articulations can also be generated by using the same method. As a result, motions of articulations of the whole body can be generated as well.

First of all, the bending angle of the articulation of the right knee formed during a variety of walking motions is measured. Then, a difference $G(\omega)$ between the frequency characteristic $B(\omega)$ of normal walking and the frequency characteristic $J(\omega)$ of an actually measured walking motion is found as follows:

$$G(\omega)=B(\omega)-J(\omega)$$

$G(\omega)$ in the above equation is a characteristic quantity which used for expressing the actually measured motion. This characteristic quantity $G(\omega)$ is stored in a characteristic-quantity data base 1041 shown in FIG. 31 which corresponds to the second data base 1031 shown in FIG. 30. As described above, in general, a characteristic quantity of a motion corresponds to the power (intensity) of a spectrum component at the gait-cycle frequency for the motion, that is, corresponds to the amplitude of the acceleration signal representing the motion. As shown in FIG. 31, there are a plurality of characteristic quantities G(w) stored in the characteristic-quantity data base 1041. Each of the characteristic quantities has an adverbial subscript for expressing the characteristic of walking such as "leisurely" for a characteristic quantity Gleisurely(w), "brisk" for a characteristic quantity Gbrisk(w) and "running" for a characteristic quantity Grun(w). In addition, it is possible to append adverbial subscripts such as "walking" and "depressed" to the symbol G to form new characteristic quantities Gwalk(w) and Gdepressed(w) respectively which are not shown in FIG. 31. It should be noted that all these new characteristics quantities can be found by using the method explained below.

A motion can be generated by synthesizing characteristic quantities for the motion to be generated to give a new characteristic quantity. The motion j(t) of the articulation is then generated by carrying out inverse-transformation processing on the newly created characteristic quantity. It is obvious from the following equation that by superposing a plurality of characteristic quantities and by adjusting the weights (the strengths) of the characteristic quantities, a motion other than those actually measured can also be generated as well.

$$j(t)=F^{-1}[J(\omega)]=F^{-1}[B(\omega)+\Sigma W_n \cdot G_n(\omega)]$$

where notation F-1 indicates the Fourier inverse transformation, notation j(t) denotes the bending angle of the articulation expressed as a function of time, notation $J(\omega)$ denotes the bending angle of the articulation expressed as a function of frequency, notation $B(\omega)$ is the characteristic quantity of the normal walking, notation $G_n(\omega)$ represents a selected characteristic quantity and notation $W_n$ is the weight of the selected characteristic quantity $G_n(\omega)$. As described above, the strength (weight) of a characteristic quantity in general corresponds to the degree of recognition likelihood of the motion represented by a spectrum whose component power at the gait-cycle frequency corresponds to the characteristic quantity.

For example, let the characteristic quantity Gwalk(j) with the subscript "walking" representing a normal-walking state be superposed on the characteristic quantity Gbrisk(w) with the subscript "brisk" representing a brisk-walking state to generate a new characteristic quantity Gbrisk(w) with a new subscript "brisk-walking" to represent an actually measured motion. Assume that only the weight of the characteristic quantity Gwalk(j) with the subscript "walking" be controlled. If the weight is set at a value equal to or smaller than 1, for example, an intermediate motion termed 'rather brisk walking' between the normal-walking and brisk-walking states is generated. If the weight is set at a value greater than 1 to emphasize the adverbial expression "brisk", on the other hand, a motion termed 'very brisk walking' is generated. As described above, new adverbial expressions such as "rather-brisk-walking" and "very-brisk-walking" can be newly created by adjusting the weight of an existing characteristic quantity in processes known as interpolation and extrapolation respectively of the existing adverbial expressions "walking" and "brisk". In addition, a new motion not actually measured can also be generated. For example, a new motion termed 'jogging' can be generated by interpolation of the characteristic quantity Gwalk(w) representing a normal-walking state and the characteristic quantity Grun (w) representing a running state. Another new motion termed 'briskly running' can be further generated by extrapolation of the characteristic quantity Gbrisk(w) representing a brisk-walking state and the characteristic quantity of the new motion term 'jogging'. This method is characterized in that motions of a variety of objects under observation can be generated with ease by synthesizing selected characteristic quantities and adjusting the weights of the selected characteristic quantities used in the synthesis. The operation to synthesize characteristic quantities to generate motion information for display is carried out by the articulation-structure-body-motion/action/work expressing apparatus 1035 shown in FIG. 30.

Figure 32:
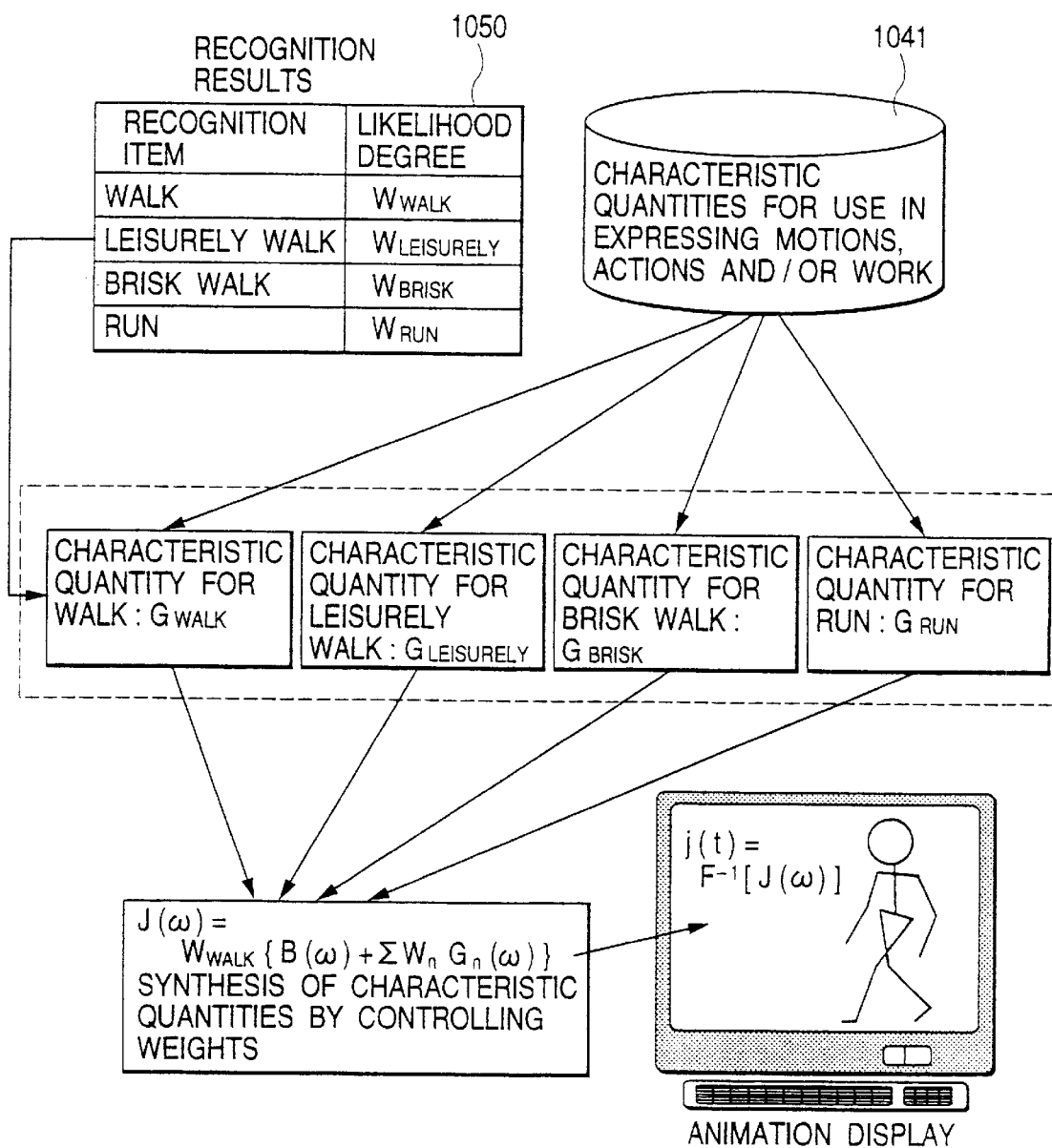
FIG. 32 is a skeleton diagram used for explaining a method based on animation using computer graphics for displaying a motion, an action and/or work resulting from superposition of a plurality of characteristic quantities.

The weights of characteristic quantities to be used in a synthesis of the characteristic quantities are each adjusted in accordance with the degree of recognition likelihood of a motion represented by the characteristic quantity which is obtained by using a technique of recognizing a motion by means of an acceleration sensor. Specifically, the motion is represented by a spectrum, the power of a component thereof at the gait-cycle frequency corresponds to the characteristic quantity. The adjustment of the weights of the characteristic quantities allow results of motion recognition to be displayed by animation using CG (computer graphics). The characteristic quantities are selected and synthesized in a method of generating motions of a human being from characteristic quantities of motions. FIG. 32 is a skeleton diagram used for explaining a method to display results of motion recognition 1050 by animation using computer graphics. As shown in the figure, the results of motion recognition 1050 include the degree of recognition likelihood $W_n$ for each recognition item $R_n$. For example, the degree of recognition likelihood for the recognition item walking is $W_{walk}$. First of all, characteristic quantities $G_n(\omega)$ for the recognition items $R_n$ are read out from the characteristic-quantity data base 1041. By using the equation given earlier, the characteristic quantities $G_n(\omega)$ are superposed on each other with the degrees of recognition likelihood $W_n$ of the recognition items used as weights of the characteristic quantities $G_n(\omega)$ of the respective recognition items as follows:

$$j(t)=F^{-1}[J(\omega)]=F^{-1}[W_{walk} \cdot \{B(\omega)+\Sigma W_n \cdot G_n(\omega)\}]$$

It is obvious from the above equation that the degree of recognition likelihood Wwalk is used as a weight of the total of all the characteristic quantities to create an expression to recognize the state of walking. According to the superposition control expressed by the above equation, the magnitude of the motion of the whole human body gradually decreases as the degree of recognition likelihood Wwalk for walking becomes smaller than 1. When the degree of recognition likelihood Wwalk for walking becomes equal to 0, all articulation angles also become 0, expressing an upright posture.

Furthermore, by selecting such a frequency ω that a computer-graphic animation character moves at the same gait cycle as the recognized gait cycle, animation using computer graphics can be generated wherein the computer-graphic animation character moves its legs at the same gait cycle as the object under observation. In this way, the speed of the motion of the recognition result can also be expressed.

FIGS. 33 to 36 are diagrams each showing an example wherein a motion is recognized by using the method of recognition provided by the present invention and a result of the recognition is displayed by animation using computer graphics. A diagram (a) of each of the figures shows an observed waveform of acceleration values measured by an acceleration sensor and a diagram (b) shows an average of the measured acceleration values. A diagram (c) shows results of recognition and a diagram (e) shows a spectrum of the motion of the human body under observation. A diagram (f) shows a characteristic quantity of the spectrum component at the gait-cycle frequency and a diagram (g) shows the results of the recognition by animation using computer graphics.

Figure 33:
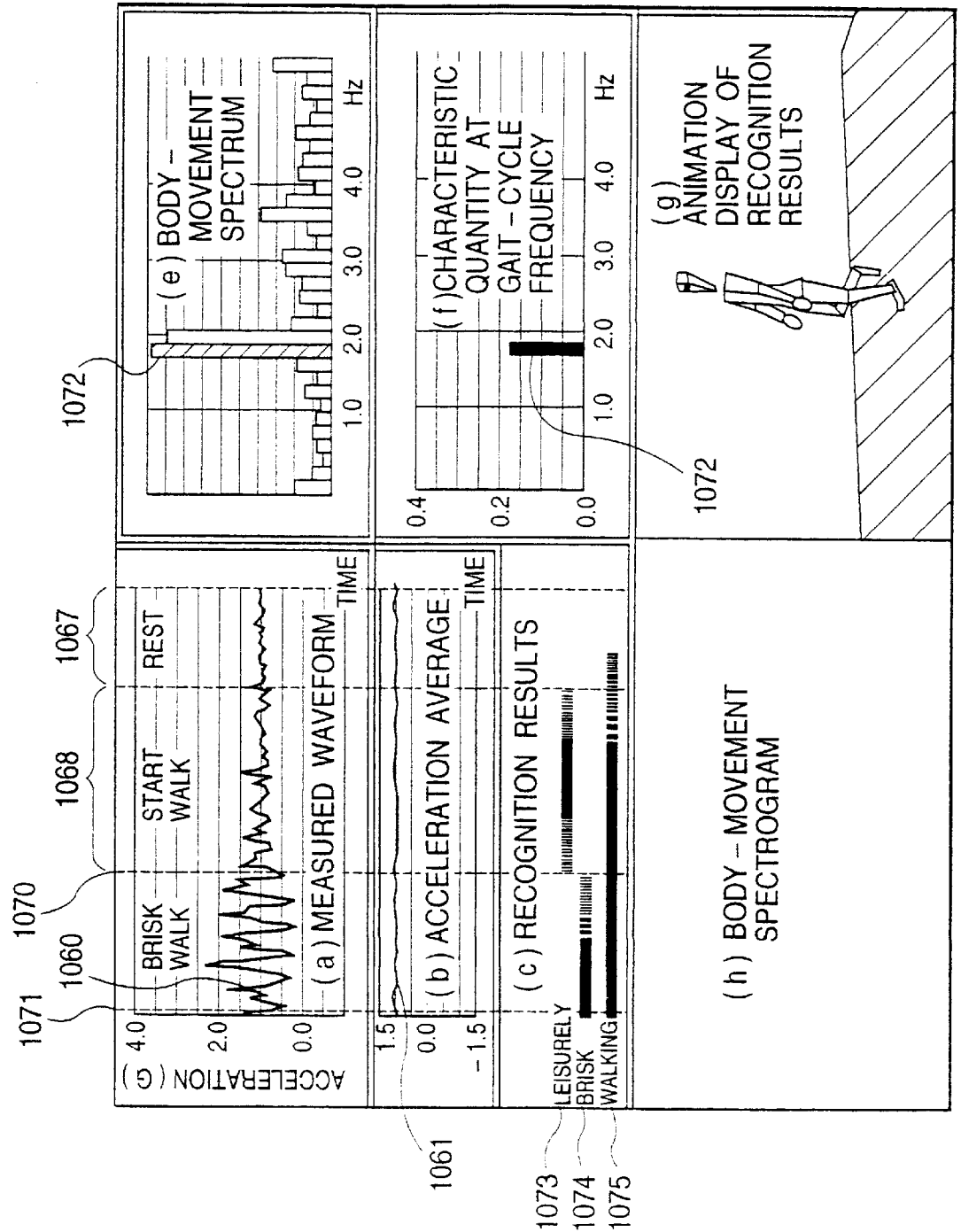
FIG. 33 is a diagram showing an example wherein a motion is recognized by using a method of recognition provided by the present invention and a result of the recognition is displayed by animation using computer graphics.

First of all, the example shown in FIG. 33 is explained. A measured waveform 1060 is shown in a diagram (a) of the figure with the horizontal and vertical axes used for representing the time and the acceleration respectively. In this example, an object under observation which is initially in a rest state starts walking gradually and finally walks briskly. It is obvious from the diagram (a) that the measured waveform has the amplitude thereof increasing as the object transits from the rest state to the brisk walking. A diagram (b) shows an average value of the measured waveform shown in the diagram (a) or the direct-current component of the waveform. In this example, the object under observation always exhibits an upright posture as evidenced by the fact that the gravitational-force acceleration 1061 is maintained at a value of about 1.0 G all the time. A diagram (e) is a spectrum of the motion of the human body obtained as a result of carrying out a frequency analysis of the measured waveform shown in the diagram (a). The horizontal and vertical axes of the diagram (e) are used for representing the frequency and the intensity (the power) of the spectrum components respectively. A diagram (f) shows only a spectrum component 1072 at a gait-cycle frequency which has a strongest intensity among all spectrum components. The diagram (f) of FIG. 33 shows only one component of the same spectrum as that shown in the diagram (e) except that the vertical axis of the former has a different scale from that of the latter. Specifically, the intensity of the diagram (e) is normalized so that the maximum intensity of the spectrum is shown as a full scale of the vertical axis. A diagram (c) shows results of observation as a motion-state spectrum with the present point of time coinciding with the left end 1071 of the waveform graph shown in the diagram (a). Graphs are shown in the diagram (c) with the horizontal and vertical axes thereof used for representing the time and an item of recognition (that is, the state of the motion) respectively. The items of recognition are, starting from the bottom, walking 1075, brisk walking 1074 and leisurely walking 1073. Each of the graphs is drawn in a synthesis of the black and white colors at a variable concentration which represents the degree of recognition likelihood (or the weight to be used in a process of synthesizing characteristic quantities). The white and black colors represent degrees of recognition likelihood of 0.0 and 1.0 respectively. At the early part of a period 1067 of the rest state, there is no item of recognition. For this reason, no graph is displayed at this part. At the end of this period 1067, however, the object under observation starts moving as evidenced by a walking graph shown in an all but white color. As the object under observation starts walking at the beginning of a period 1068 of a leisurely-walking state (a rest-to-walking transition), a leisurely-walking graph is also shown along with the walking graph. It is obvious that, during this period 1068, the colors of both the walking and leisurely-walking graphs turn from white to black little by little, indicating gradually increasing degrees of recognition likelihood of the items of recognition 'walking' and 'leisurely walking' denoted by reference numerals 1075 and 1073 respectively. Furthermore, as the object under observation approaches the boundary 1070 between the leisurely-walking transition 1068 and a subsequent brisk-walking state, the color of the leisurely-walking graph turns from black to white little by little, indicating a gradually decreasing degree of recognition likelihood of the item of recognition 'leisurely walking' denoted by reference numeral 1073. This is because the object under observation approaches a normally-walking motion. As the object under observation passes through the boundary 1070, a brisk-walking graph is displayed, showing a gradually increasing degree of recognition likelihood of the item of recognition 'brisk walking' denoted by reference numeral 1074 in place of the leisurely-walking graph. The brisk-walking graph indicates that a brisk-walking state has been recognized. It is a diagram (g) that shows the result of the recognition by animation using computer graphics. To be more specific, the animation shows a briskly walking motion at the present point of time at the left end 1071 of the waveform graph shown in the diagram (a). A diagram (h) shows a spectrogram of the motion of the human body with the horizontal and vertical axes used for representing the time and the frequency respectively. Even though not shown in detail, the spectrogram represents the intensities of the spectrum by the concentration of picture elements.

Figure 34:
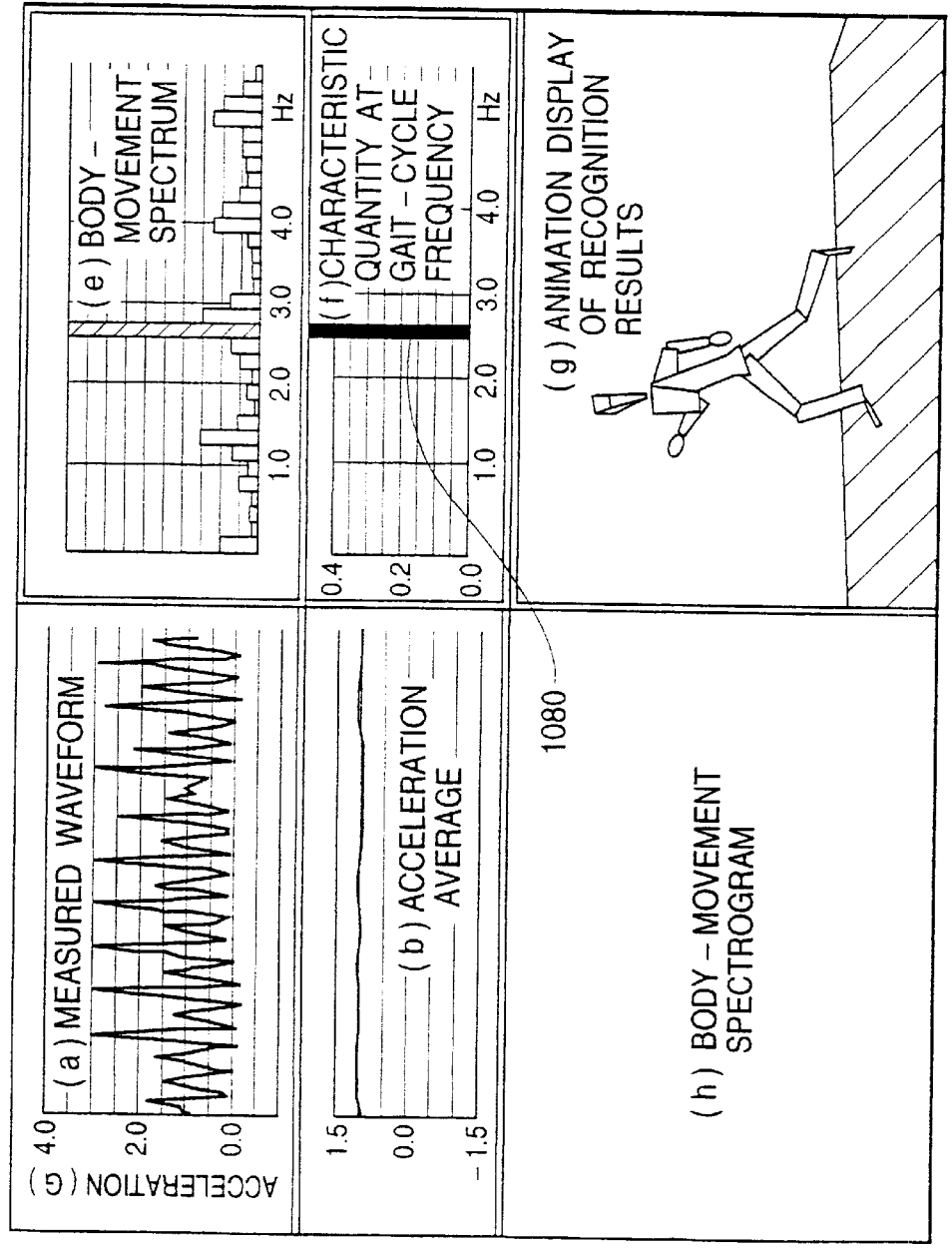
FIG. 34 is a diagram showing another example wherein a motion is recognized by using the method of recognition provided by the present invention and a result of the recognition is displayed by animation using computer graphics.
Figure 35:
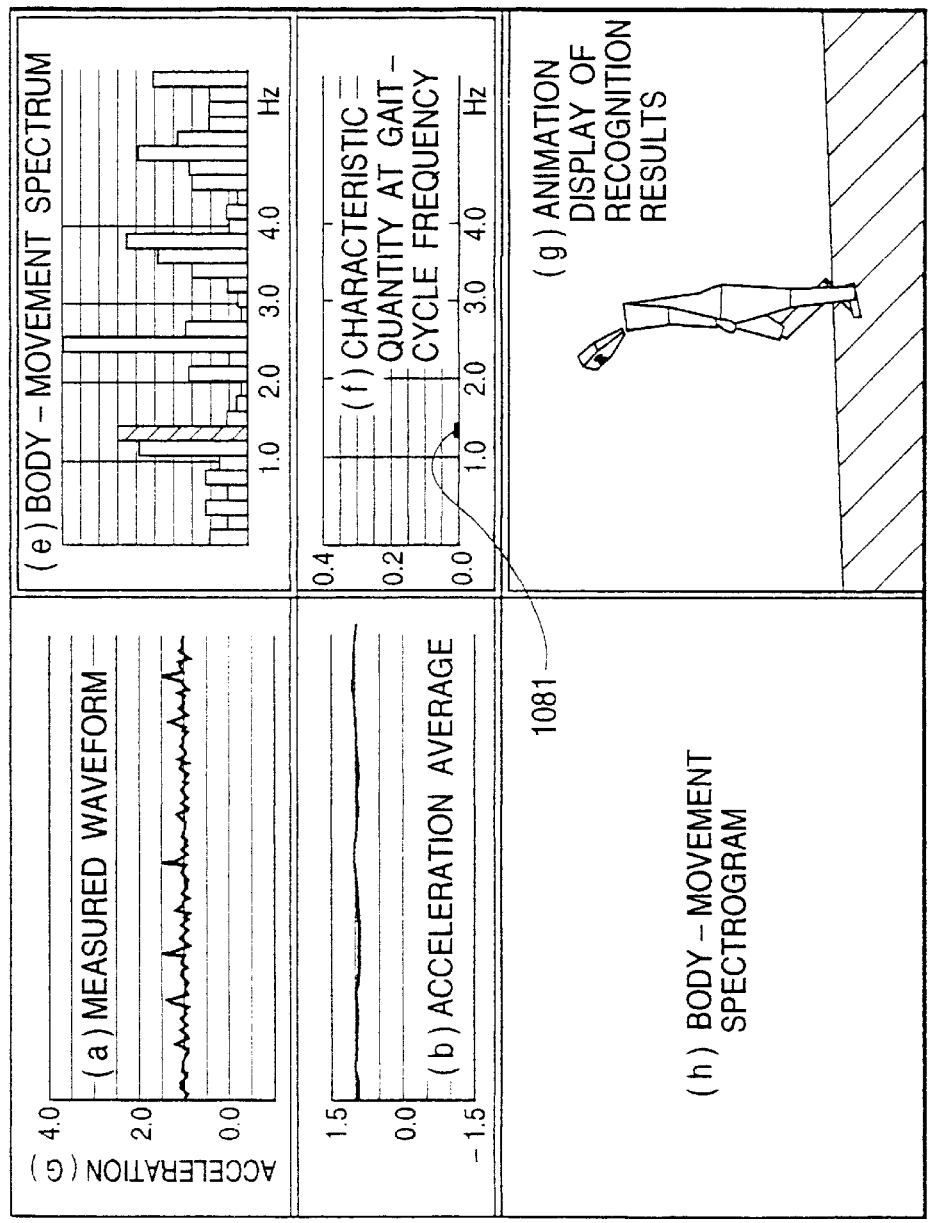
FIG. 35 is a diagram showing still another example wherein a motion is recognized by using the method of recognition provided by the present invention and a result of the recognition is displayed by animation using computer graphics.
Figure 36:
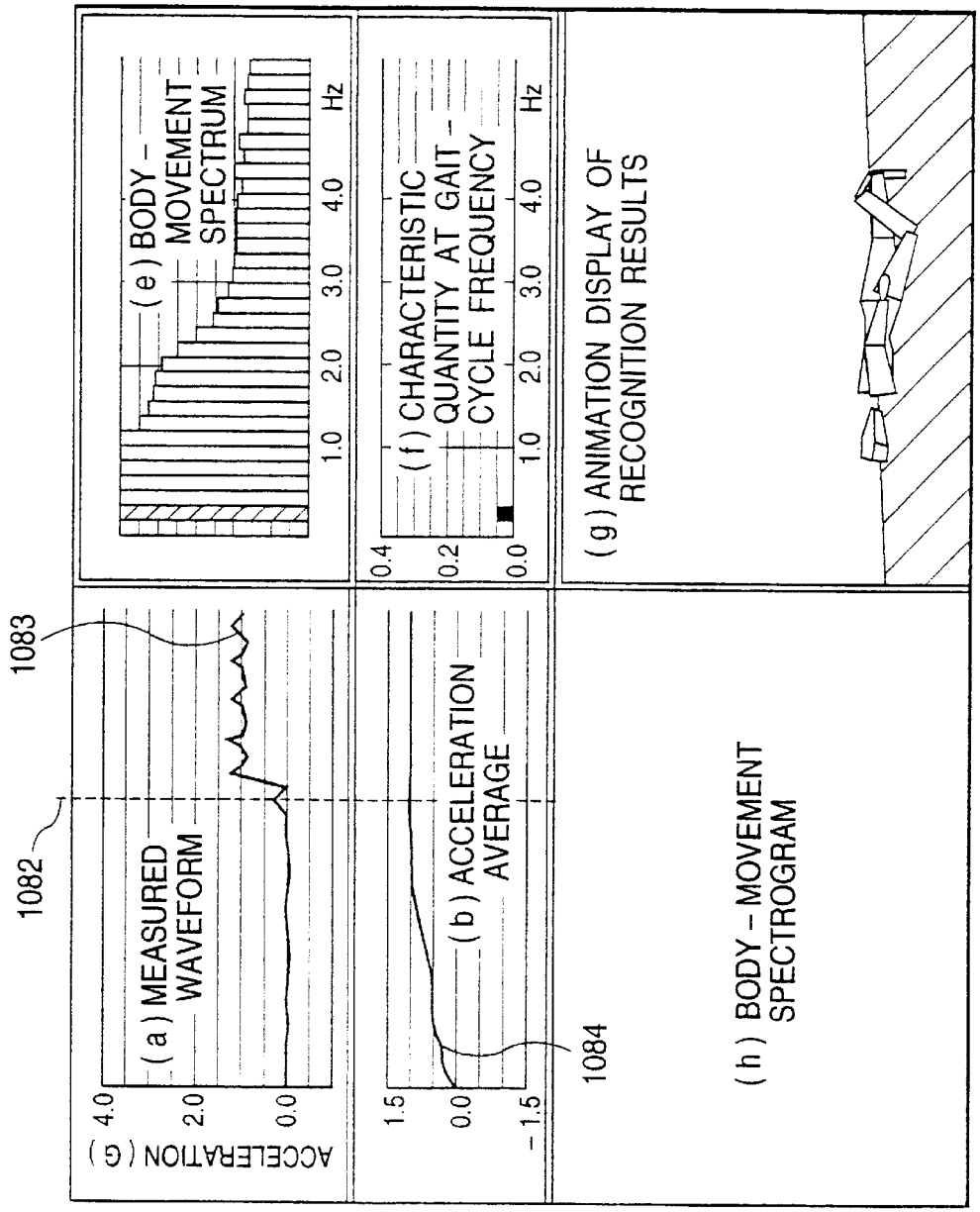
FIG. 36 is a diagram showing a still further example wherein a motion is recognized by using the method of recognition provided by the present invention and a result of the recognition is displayed by animation using computer graphics.

FIG. 34 is diagrams showing an example of recognition of a running state. It is obvious from a diagram (a) of the figure that the amplitude of the measured waveform is substantially large in comparison with that shown in FIG. 33. A diagram (f) shows the characteristic quantity of only a spectrum component 1080 at a gait-cycle frequency which has a strongest intensity among all spectrum components. The strongest intensity shown in FIG. 34 is much stronger than the corresponding one shown in FIG. 33. A diagram (g) shows a result of the recognition by animation using computer graphics. FIG. 35 is diagrams showing an example of recognition of a leisurely-walking state, that is, a state of walking calmly and slowly. It is obvious from a diagram (a) of the figure that the amplitude of the measured waveform is small in comparison with that shown in FIG. 33 due to the fact that the motion is in a leisurely-walking state. A diagram (f) shows the characteristic quantity of only a spectrum component 1081 at a gait-cycle frequency which has a strongest intensity among all spectrum components. The strongest intensity shown in FIG. 35 is much weaker than the corresponding one shown in FIG. 33. A diagram (g) shows a result of the recognition by animation using computer graphics illustrating a motion in a leisurely-walking state or a state of walking totteringly. The animation is generated by superposition of the characteristic quantities obtained in the recognition of the walking and the totteringly-walking states by applying their respective degrees of recognition likelihood as weights. FIG. 36 is diagrams showing an example of recognition of a collapsing state. The object under observation collapses at a point of time denoted by a vertical dashed line 1082 in the figure. At the point of time, the amplitude of the waveform abruptly drops to 0.0 G as shown in a diagram (a) while the average value of the acceleration also gradually decreases to 0.0 G, indicating a transition from the upright posture to a lying-down posture. With the human body put in this lying-down posture, the measurement axis (or the sensitivity direction) of the acceleration sensor is oriented perpendicularly to the gravitational-force direction, making it impossible to observe the gravitational-force acceleration. A diagram (g) shows a result of the recognition by animation using computer graphics illustrating a state of the lying-down posture.

It should be noted that the apparatus and the system provided by the present embodiment can also be used as a tool for diagnosing and displaying the state of rehabilitation training. In this case, instead of displaying a result of recognition by animation using computer graphics as it is, a problem encountered in the state can be emphasized. For example, when a state in which the object under observation is dragging the feet thereof is recognized, the state is displayed by animation by emphasizing the degree of recognition likelihood for the recognized state which is used as the weight for the feet-dragging state. In this way, the spot in question can be emphasized and displayed in the form of a figure which can be understood by the observer with ease. Of course, such emphasis processing is applicable to all fields of motion, action and/or work recognition other than the rehabilitation training in order to display a result of recognition in the form of a figure that can be understood by the observer with ease.

As described above, the present embodiment allows a result of recognition of a motion, an action and/or work to be expressed by animation that can be intuitively understood by the observer with.ease, exhibiting an effect of presenting an easily understandable result of recognition to the observer.

It should be noted that, while the present invention has been described with reference to an illustrative preferred embodiment wherein an articulation-structure body is displayed on a display unit by animation using computer graphics, the description is not intended to be construed in a limiting sense. That is to say, the present invention can also be applied to a pose of a static picture expressing a characteristic of a motion. In the case of a walking motion, for example, a picture of a side view of a walking object is taken and the resulting static picture is used as a characteristic quantity (a characteristic picture) of the walking motion. Then, when a result of recognition indicates a walking motion, the static picture is read out and displayed. In this case, the amount of processing is small in comparison with the display by animation using computer graphics described above, giving rise to an effect that it is possible to display a result of recognition by using a computer with a low processing speed.

Figure 37:
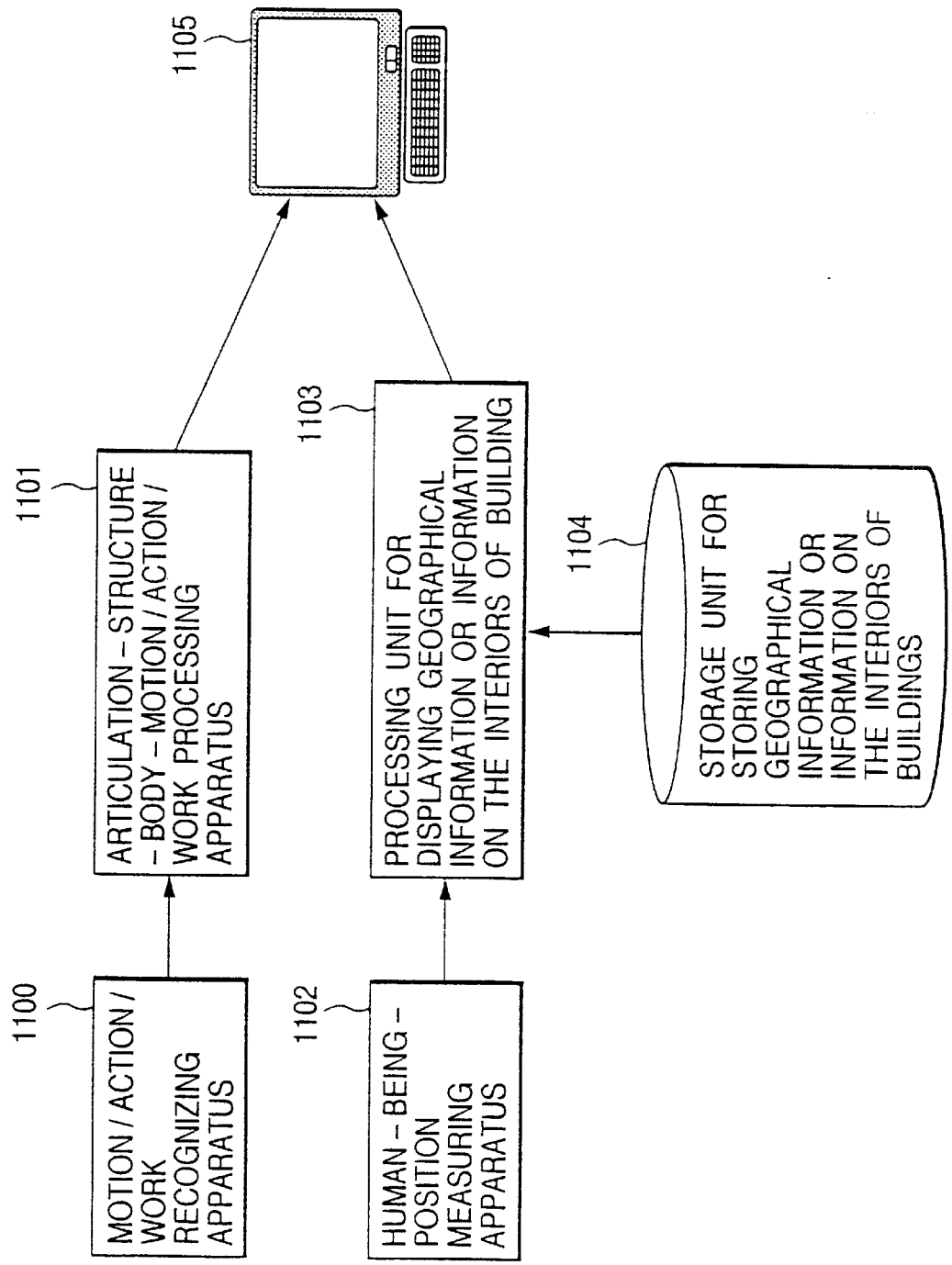
FIG. 37 is a diagram showing the configuration of a system for displaying a result of recognizing the position as well as the motion, the action and/or the work of an object under observation.

The following is description of an embodiment for displaying a result of recognizing the position as well as the motion, the action and/or the work of an object under observation. Unlike the embodiments described so far, in the case of the present embodiment, the position of an object under observation is also recognized and displayed. FIG. 37 is a diagram showing the configuration of a system for displaying a result of recognizing the position as well as the motion, the action and/or the work of an object under observation. Reference numeral 1100 shown in the figure is a motion/action/work recognizing apparatus for recognizing a motion, an action and/or work of a human being by using typically the method of recognition explained earlier with reference to FIG. 1. Reference numeral 1101 denotes an articulation-structure-body-motion/action/work processing apparatus provided with a function for displaying a motion, an action and/or work of an articulation-structure body by animation using computer graphics on the basis of a result of recognition of a motion, an action and/or work of an articulation-structure body carried out by the motion/action/work recognizing apparatus 1100 by using typically the displaying method explained earlier with reference to FIG. 31. Reference numeral 1102 is a human-being-position measuring apparatus for identifying the position of an object under observation using typically the method explained earlier with reference to FIG. 11. Reference numeral 1103 is a processing unit for displaying geographical information or information on the interiors of buildings. The geographical information includes altitudes of fields and mountains above the sea level, road and right-of-way data, and data of locations and shapes of buildings and structures. On the other hand, the information on the interiors of buildings includes data of room arrangement planning in the buildings and layout of equipment. These pieces of information are stored in a data base 1104. Reference numeral 1105 is a display unit. The processing unit 1103 for displaying geographical information or information on the interiors of buildings is used for expressing the geographical information or the information on the interior of a building related to the circumference of a position of the object under observation identified by the human-being-position measuring apparatus 1102 into a two-dimensional or three-dimensional figure by using a method for displaying geographical information and information on the interiors of buildings. In the mean time, at the position of the object under observation, the motion of the object is displayed by computer-graphic animation using the articulation-structure-body-motion/action/work processing apparatus 1101.

Figure 38:
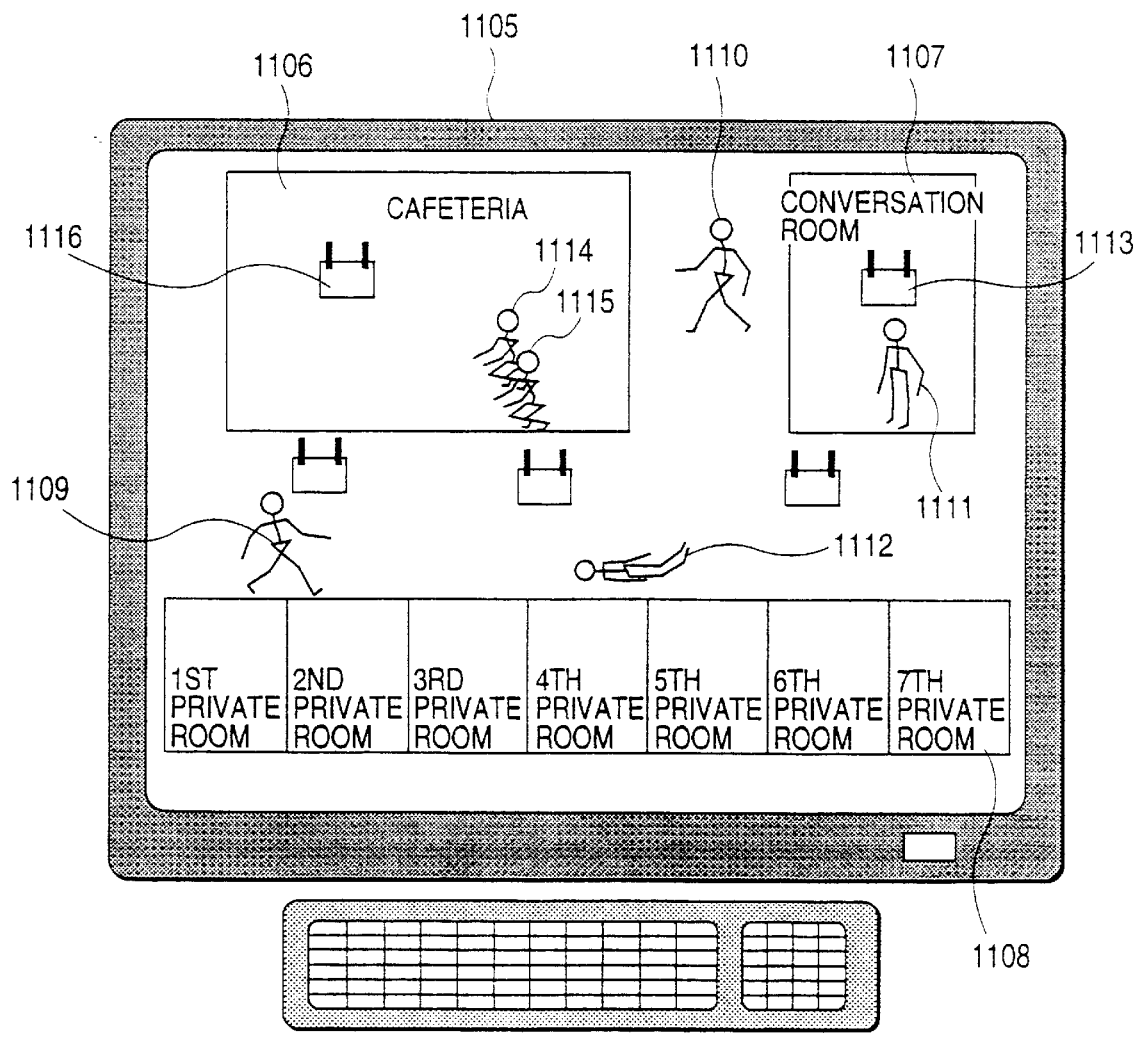
FIG. 38 is a diagram showing a typical screen displayed with results of recognizing the positions as well as the motions, actions and/or work of objects under observation used as a base.

FIG. 38 is a diagram showing an example of operations carried out by the system shown in FIG. 37. The example shows motions of objects under observation such as patients in a hospital. In this example, a layout of the interior of the hospital is illustrated. If the object under observation gets out from a building, however, outdoor scenery including roads and parks can also be expressed in the same way. Reference numerals 1105 and 1106 shown in the figure are a display screen and a cafeteria respectively. Reference numeral 1107 denotes a conversation room and reference numeral 1108 denotes private rooms. The layout of the cafeteria 1106, the conversation room 1107 and the private rooms 1108 is created on the basis of the geographical information and the information on the interiors of buildings stored in the data base 1104 shown in FIG. 37. Reference numerals 1110, 1111, 1112, 1114, 1115 and 1109 each denote a human being present in the hospital. Attached to each of the objects under observation are the human-being-position measuring apparatus 1102 and the motion/action/work recognizing apparatus 1100 shown in FIG. 37. The human-being-position measuring apparatus 1102 is used for identifying the position of the object under observation, to which this human-being-position measuring apparatus 1102 is attached, by using the strengths of electric waves transmitted by PHS base stations 1116 or 1113. On the other hand, the motion/action/work recognizing apparatus 1100 is used for recognizing the motion of the object under observation to which this motion/action/work recognizing apparatus 1100 is attached. Then, at the position of the object under observation, the motion of the object is displayed by computer-graphic animation using the articulation-structure-body-motion/action/work processing apparatus 1101. As shown in FIG. 38, in this example, the object under observation 1109 is walking briskly in front of the first private room 1108 while the objects under observation 1114 and 1115 are sitting at the cafeteria 1106.

In this way, the present embodiment allows what motion each object under observation is performing and at which location each object in motion is to be expressed by animation which can be understood by the observer very easily, exhibiting an effect that it is possible to present an easily understandable result of observation to the observer.

In addition, the present embodiment also exhibits an effect that observation using equipment such as a television camera becomes hardly affected by a blind spot or the like which is prone to result in the observation, making it possible to carry out good observation at any place.

Further, while a television camera generally provides a smaller picture of the object under observation as the distance to the object becomes longer, making the observation difficult, the present embodiment on the other hand exhibits an effect that good observation is possible at any place as long as the position of an object under observation is within a range that allows data representing results of the observation to be transmitted from the human-being-position measuring apparatus 1102 and the motion/action/work recognizing apparatus 1100 to the processing unit 1103 for displaying geographical information or information on the interiors of buildings and the articulation-structure-body-motion/action/work processing apparatus 1101 respectively.

Furthermore, while monitoring pictures generated by a television camera allows the observer to obtain information clearly indicating who and where the object under observation is, inadvertently giving rise to a possibility that privacy of the object is infringed, the present embodiment on the other hand exhibits an effect that, by expressing the motions, actions and/or work of only, for example, the objects 1114 and 1115 under observation shown in FIG. 38 by animation using computer graphics wherein the objects are represented by animation characters having the same shape as the other objects under observation except the ways they walk, it is possible to know the fact that the two objects 1114 and 1115 are sitting at locations in the cafeteria 1106 but impossible to know other personal information, leading to protection of personal privacy.

Figure 39:
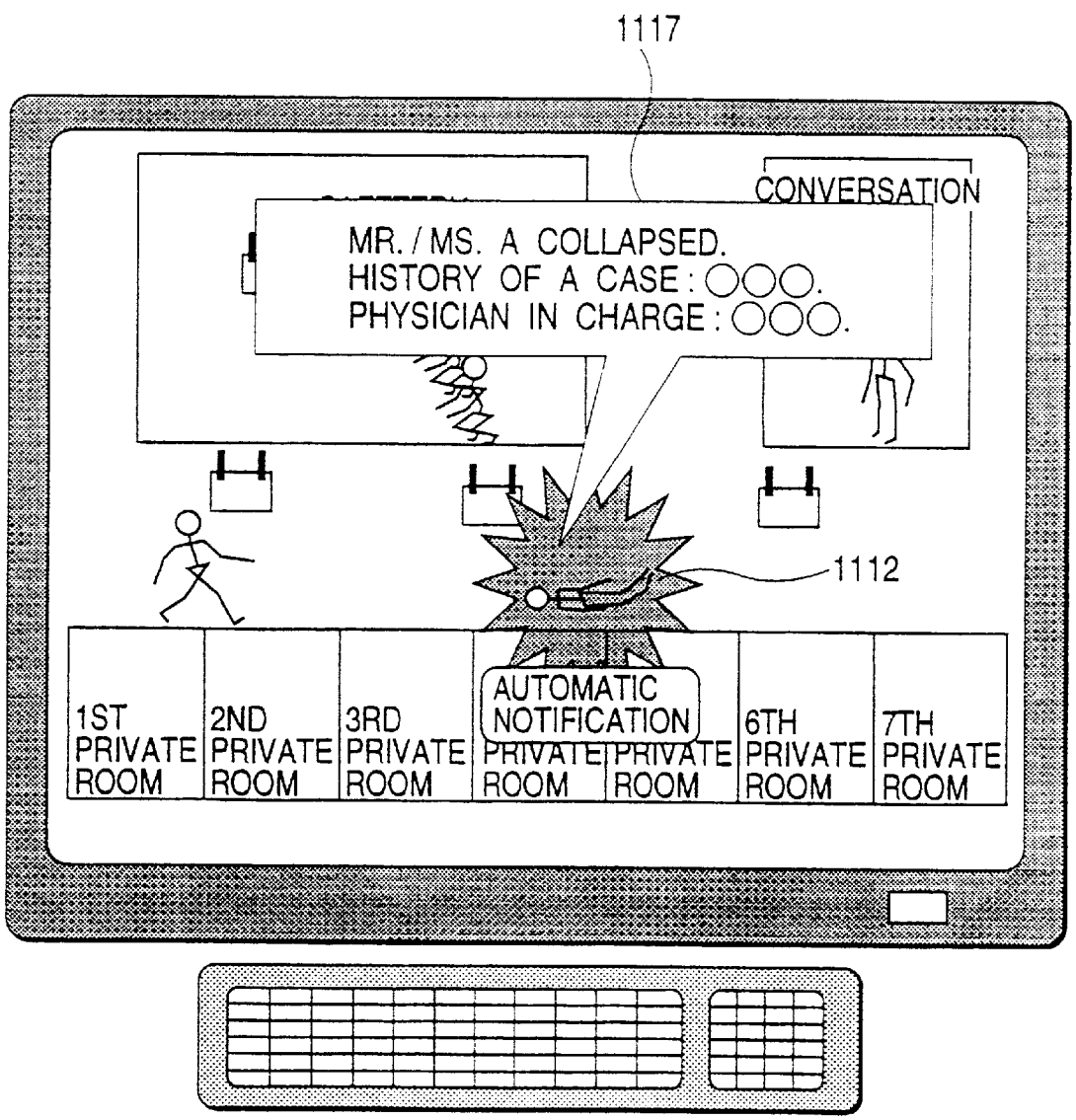
FIG. 39 is a diagram showing a display example illustrating the event of an emergency.

FIG. 39 is a diagram showing a display example illustrating the event of an emergency. Examples of emergencies are states of collapsing and critically suffering states a patient. In the example shown in the figure, the object under observation 1112 collapses in front of the fourth private room. As described above, in the displaying method adopted by the embodiment described before, personal information of all objects under observation is concealed for the sake of protection of privacy. In the case of the present embodiment, however, personal information of an object under observation is deliberately disclosed in the event of an emergency involving the object under observation. An emergency is recognized by using the method explained earlier with reference to FIG. 20. In the explanation of FIG. 20, a particular motion, action and/or work is recognized. In the case of the present embodiment, since a hospital is cited as an example, the particular motion, action and/or work refers to an emergency state of a patient. Having been explained with reference to FIG. 20, however, the description of the recognition method is not repeated. In the event of such an emergency, the position as well as the motion, the action and/or the work of the object under observation is displayed as the animation character 1112 and, at the same time, the display screen also includes information 1117 on the patient involved in the emergency such as the name, the history of a case, the physician in charge and the name of the patient's protector which are obtained by referring to the ID numbers of measuring and recognition apparatuses attached to the patient.

The present embodiment thus exhibits an effect that, in the event of an emergency, the observer is allowed to immediately obtain information on the location and the state of the emergency as well as minimum personal information on the object under observation involved in the emergency which is by all means required in handling the emergency while, at the same time, the privacy of other objects under observation remains protected.

Figure 40:
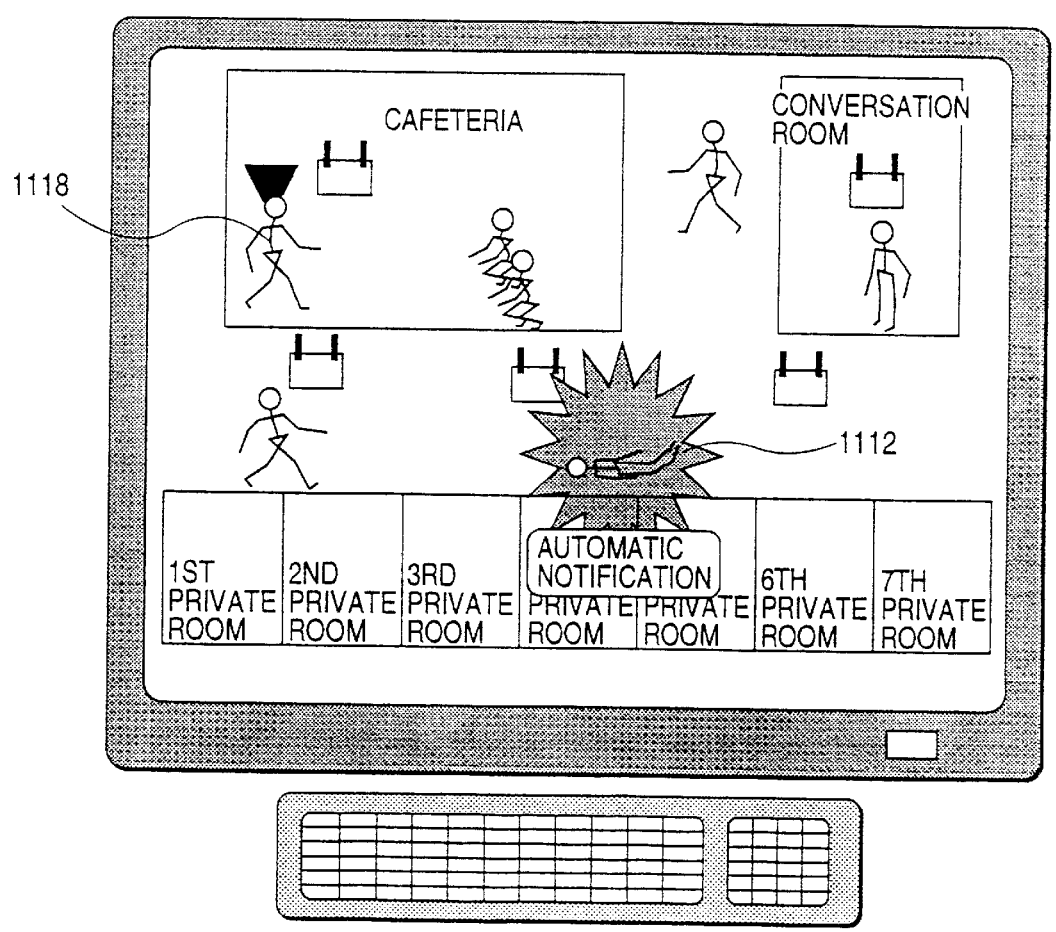
FIG. 40 is a diagram showing an example of illustrating positions as well as motions, actions and/or work of hospital staffs.

FIG. 40 is a diagram showing an example of illustrating positions and motions, actions as well as work of hospital staffs. In the embodiment described above, in the event of an emergency, it is necessary to select hospital staffs who are capable of handling the emergency. In order to select such staffs, it is necessary to display the current positions and motions, actions as well as work of the hospital staffs. In this example, an animation character 1118 is used for expressing a hospital staff. As shown in the figure, the animation character 1118 wears a hat for showing that the animation character is used for expressing a hospital staff. In this example, the hospital staff 1118 is merely walking, being in a condition which can be said to be sufficiently capable of handling the emergency. If a result of the recognition of the action taken or work done by the animation character 1118 indicates that the hospital staff is currently involved in an operation or handling taking care another patient in a critical condition, however, other hospital staffs in close proximity to the location of the emergency can be found by watching this screen without the need to directly check with the other hospital staffs.

The present embodiment thus exhibits an effect that people capable of handling an emergency can be judged without the need to directly check with those people.

In the case of the present embodiment, it is a human being who forms a judgment as to who should handle an emergency as described above. It should be noted, however, that in place of a human being, a computer can also be used for selecting optimum hospital staffs automatically by executing a variety of optimized algorithms based on the location of a patient in a critical condition, the cause of an emergency, the history of a case for the patient and the physician in charge of the patient as well as the locations, the working conditions and the specialties of hospital staffs in close proximity to the place of the emergency.

Figure 41:
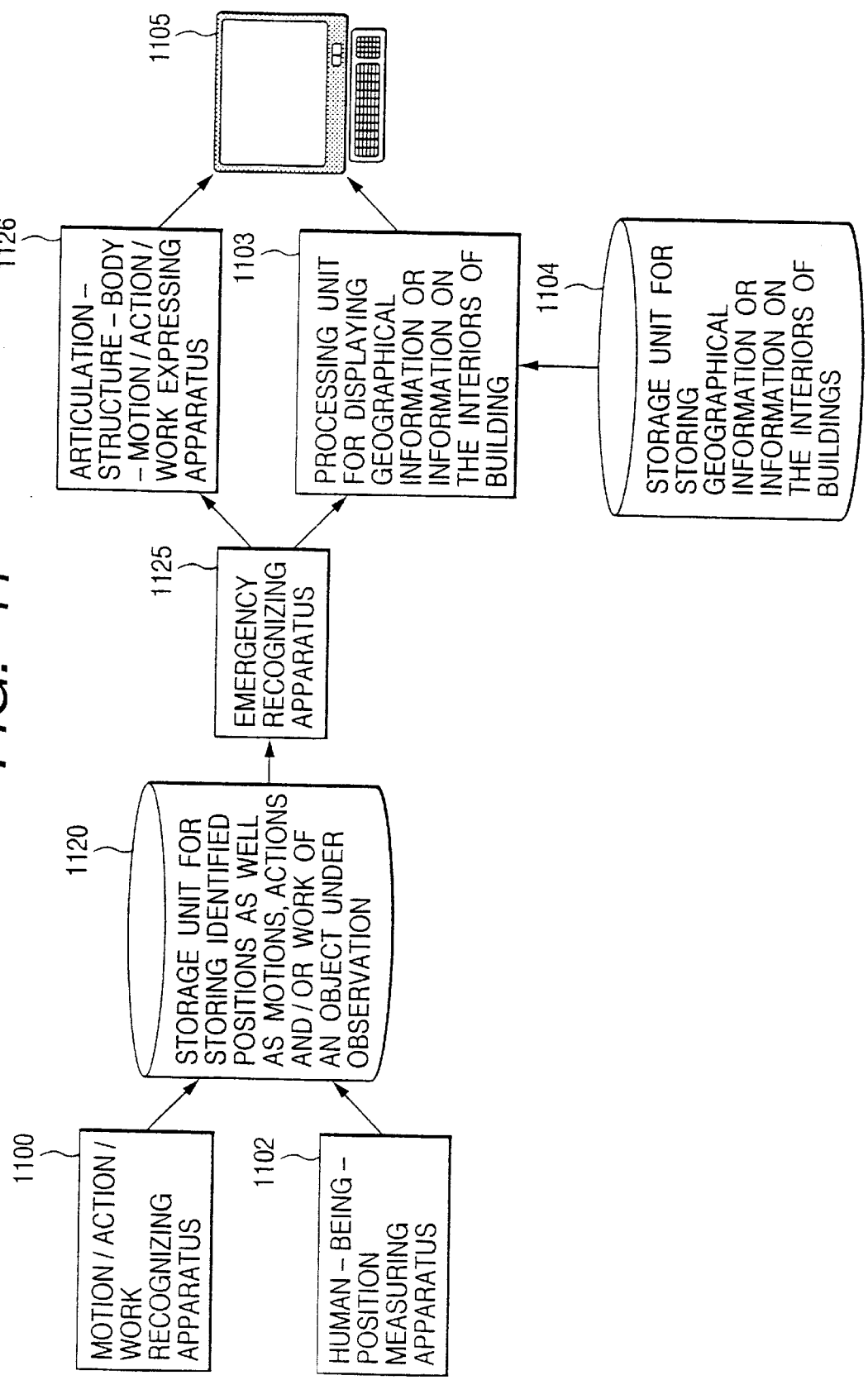
FIG. 41 is a diagram showing the configuration of a system for displaying a sequence of motion states leading to the event of an emergency and for carrying out processing to handle the emergency.

FIG. 41 is a diagram showing the configuration of a system for displaying a sequence of motion states leading to the event of an emergency and for carrying out processing to handle the emergency. An emergency is recognized by using the method explained earlier with reference to FIG. 20. The pieces of processing which are carried out by the system shown in FIG. 41 after an emergency has been recognized are thus pieces of post-emergency-recognition processing.

As shown in FIG. 41, the system includes a storage unit 1120 for storing information on the position as well as the motion, the action and/or the work of each object under observation, that is, a patient getting into a critical condition in this case. Specifically, the storage unit 1120 is used for storing the types of a motion, an action and/or work of each object under observation recognized by the motion/action/work recognizing apparatus 1100, information on the location of each object under observation identified by the human-being-position measuring apparatus 1102 and a time at which each motion is recognized. FIG. 42 is an example of the structure of data stored in the storage unit 1120 to represent the recognized motion, action and/or work of an object under observation as well as the position and the point of time at which the motion, the action and/or the work are recognized. As shown in the figure, the structure comprises an upper row 1122 for describing the states of the motion, action and/or work and a lower row 1123 for describing the coordinates x, y and z of the location and the time at which the motion, action and/or work occur. A new set of such information is added each time a state of a motion, an action and/or work is recognized. In this example, a set of information added last is recorded on a column 1125. That is to say, sets of information are added sequentially one after another in the right and down direction. The more a column is located to the left or the higher the position of a column in the data structure, the older chronologically the set of information recorded on the column.

Let a specific motion pattern 1121 of a patient in an emergency be collapsing, lying down and lying down forever as shown in FIG. 42. When this specific motion pattern is detected, an emergency recognizing apparatus 1125 carries out animation processing by using an articulation-structure-body-motion/action/work expressing apparatus 1126 for expressing also a transition of an object under observation from a location to another in order to display details of the emergency.

Figure 43:
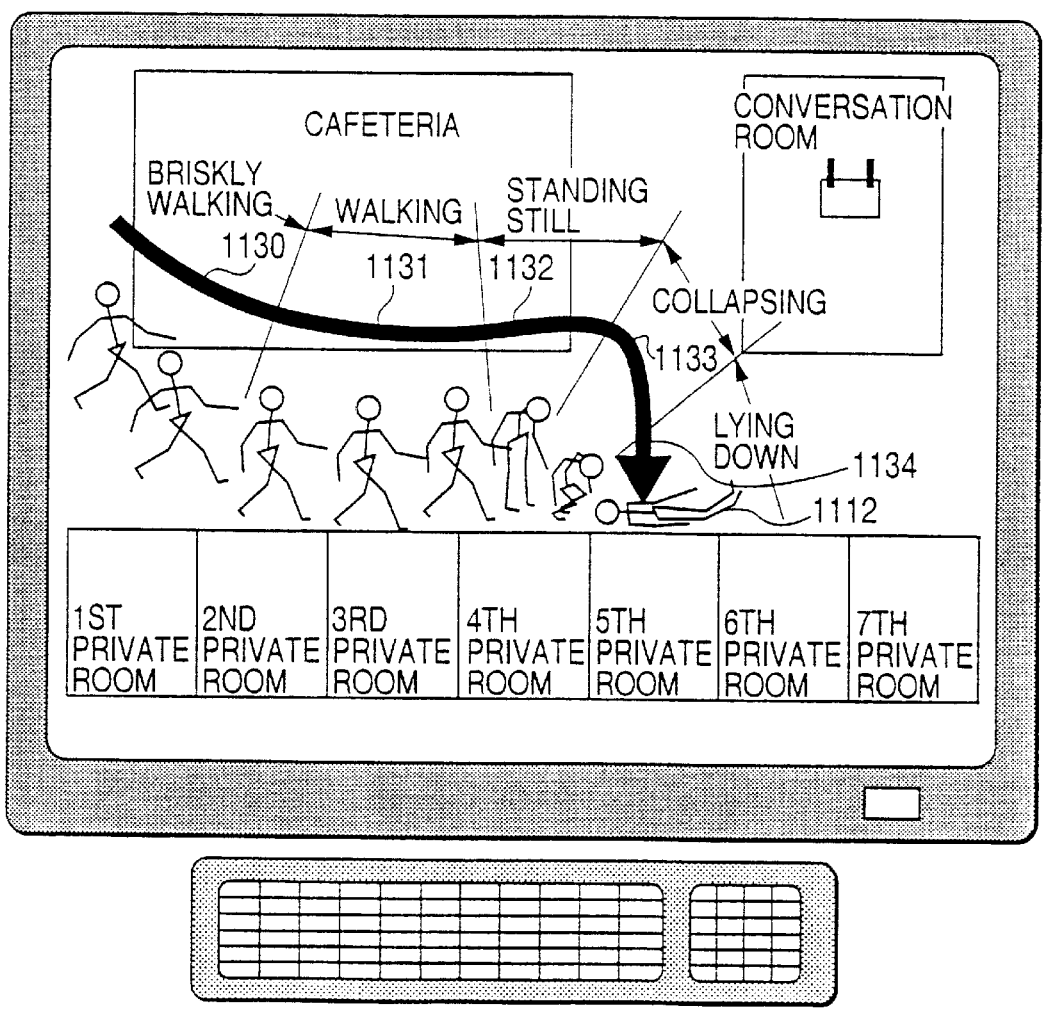
FIG. 43 is a diagram showing, in the event of an emergency, a typical display of a sequence of motion states leading to an emergency which are expressed by an articulation-structure-body-motion/action/work expressing apparatus.

FIG. 43 is a diagram showing, in the event of an emergency, a typical display of a sequence of motion states leading to the emergency which are expressed by the articulation-structure-body-motion/action/work expressing apparatus 1126. Reference numeral 1112 is a place at which a patient under observation collapses. As the emergency recognizing apparatus 1125 detects the specific motion pattern 1121 shown in FIG. 42, the storage unit 1120 used for storing the identified positions as well as the recognized motions, actions and/or work of the patient is traced back retroactively by a predetermined time to a column 1124 of the data structure for recording a brisk-walking state in the case of this example. Animation based on motions, actions and/or work of the patient under observation is then carried out, starting with the set of information recorded on the column 1124, progressing sequentially one set after another toward the chronologically newest set. The example shown in FIG. 43 illustrates animation wherein the retroactive trace of the emergency starts from a period 1130 in which the patient was briskly walking. In a subsequent period 1131, the patient was walking and, in the next period, 1132, the patient was standing still. Subsequently, during a period 1133 the patient collapsed and, in the following period 1134, the patient is lying down and does not move any more. It should be noted that, by repeating the process described above, a sequence of motion states leading to the event of an emergency can be displayed repeatedly.

The present embodiment thus exhibits an effect that, since a sequence of motion states leading to the event of an emergency can be displayed retroactively to a point of time in the past, detailed understanding of the emergency based on a sequence of circumstances leading to the emergency can thus be obtained with ease and actions to be taken for handling the emergency can therefore be studied easily.

Figure 44:
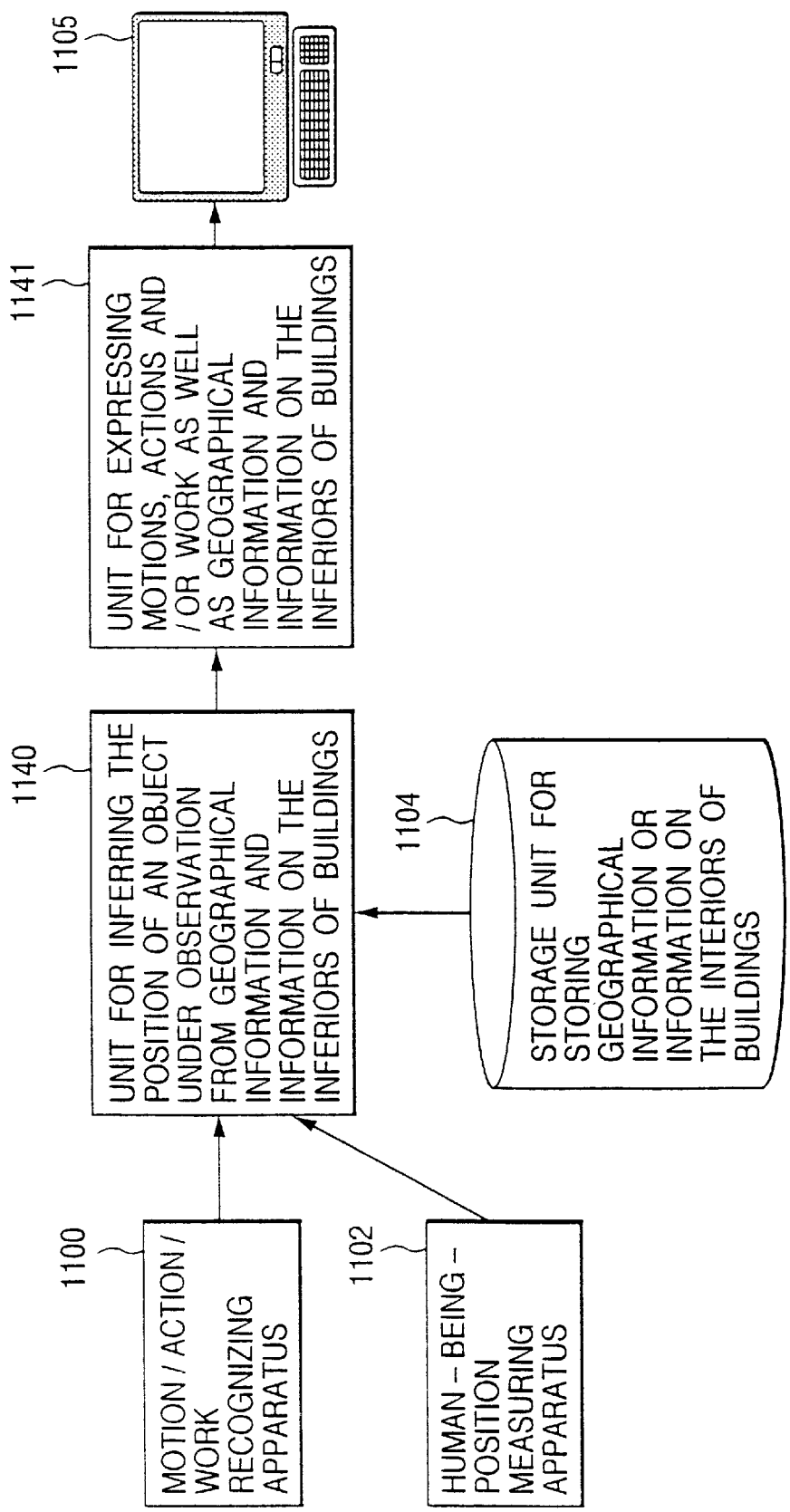
FIG. 44 is a diagram showing the configuration of a system for improving the accuracy of measured values obtained by means of a human-being-position measuring apparatus by using results of recognizing a motion, an action and/or work as a reference for consideration.
Figure 45:
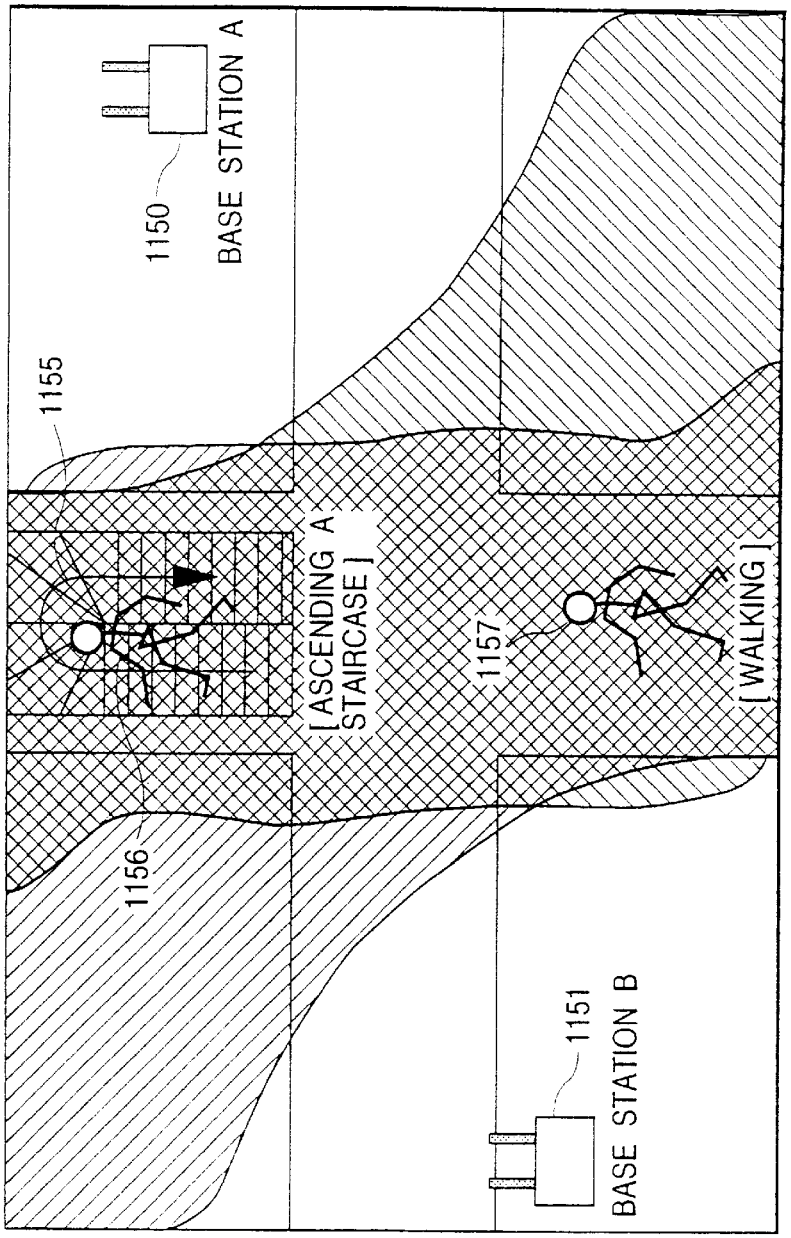
FIG. 45 is a diagram used for explaining how the accuracy of measured values obtained by means of the human-being-position measuring apparatus can be improved by using results of recognizing a motion, an action and/or work as a reference for consideration.

The following is description of an embodiment implementing a method for improving the accuracy of measured values obtained by means of the human-being-position measuring apparatus 1102 by using results of recognizing a motion, an action and/or work as a reference for consideration with reference to FIGS. 44 and 45. FIG. 44 is a diagram showing the configuration of a system for improving the accuracy of measured values obtained by means of the human-being-position measuring apparatus 1102 by using results of recognizing a motion, an action and/or work as a reference for consideration, and FIG. 45 is a diagram used for explaining how the accuracy of measured values obtained by means of the human-being-position measuring apparatus 1102 can be improved by using results of recognizing a motion, an action and/or work as a reference for consideration.

Having been described before, detailed explanation of the motion/action/work recognizing apparatus 1100 is omitted. In the human-being-position measuring apparatus 1102, the distribution of the electric-field intensity of an electric wave transmitted by each of a plurality of base stations is found by measurement or simulation in advance. The human-being-position measuring apparatus 1102 attached to an object under observation receives electric waves from the base stations and computes the intensity of each of the electric waves. The intensities of the electric waves are then compared with the distributions of electric-field intensity in order to identify some candidate positions. For example, assume that the human-being-position measuring apparatus 1102 attached to an object under observation receives an electric wave with an electric-field intensity Xdb from a base station A denoted by reference numeral 1150 and an electric wave with an electric-field intensity Ydb from a base station B denoted by reference numeral 1151 in FIG. 45. Reference numeral 1152 shown in the figure is a region of the distribution of electric-field intensity of the electric wave transmitted by the station A 1150 in which the electric-field intensity is equal to Xdb. By the same token, reference numeral 1153 is a region of the distribution of electric-field intensity of the electric wave transmitted by the station B 1151 in which the electric-field intensity is equal to Ydb. As described above, the distributions have been found by measurement or simulation in advance. Thus, a region in which the human-being-position measuring apparatus 1102 is capable of receiving the electric waves from both the stations A and B at the same time is a junction region 1154 of the regions of the distributions of electric-field intensity 1152 and 1153. That is to say, the object under observation is at a place somewhere in the junction region 1154. However, this region has a substantially large area due to a poor accuracy of measurement of an electric-field intensity by the human-being-position measuring apparatus 1102 and due to random reflection of the electric waves. As a result, it is merely possible no more than to identify roughly a position of the object under observation. In order to solve this problem, there is thus provided a unit 1140 adopting a method for inferring the position of an object under observation from geographical information and information on the inferiors of buildings. By using this method, a more precise position of an object under observation can be identified from a region, in which the object is present, found by the human-being-position measuring apparatus 1102, the state of a motion, an action and/or work of the object found by the motion/action/work recognizing apparatus 1100 as well as the geographical information and information on the interiors of buildings stored in the data base 1104. In the case of the example shown in FIG. 45, for example, assume that there are two objects 1156 and 1157 under observation in the region found by the human-being-position measuring apparatus 1102 but, according to the state of the motion, action and/or work of the object found by the motion/action/work recognizing apparatus 1100, the object is recognized to be in a motion of ascending a staircase. The geographical information and information on the inferiors of buildings stored in the data base 1104 is then searched for a place at which the staircase is located. From a result of the search, a place 1155 at which the staircase is located is identified as the position of the object under observation, that is, the object 1156 instead of the object 1157 in this case. If the motion/action/work recognizing apparatus 1100 suggests that the object is walking at an ordinary location with no particular shape as is the case with the object 1157, on the other hand, then the exact position of the object under observation can also be identified because, at least, the position of the object is clearly not the place at which the staircase is located. In addition, the position of an object under observation can also be identified from information on a point of time the object finishes the ascending of the staircase and a period of time during which the object is walking as follows.

Figure 46:
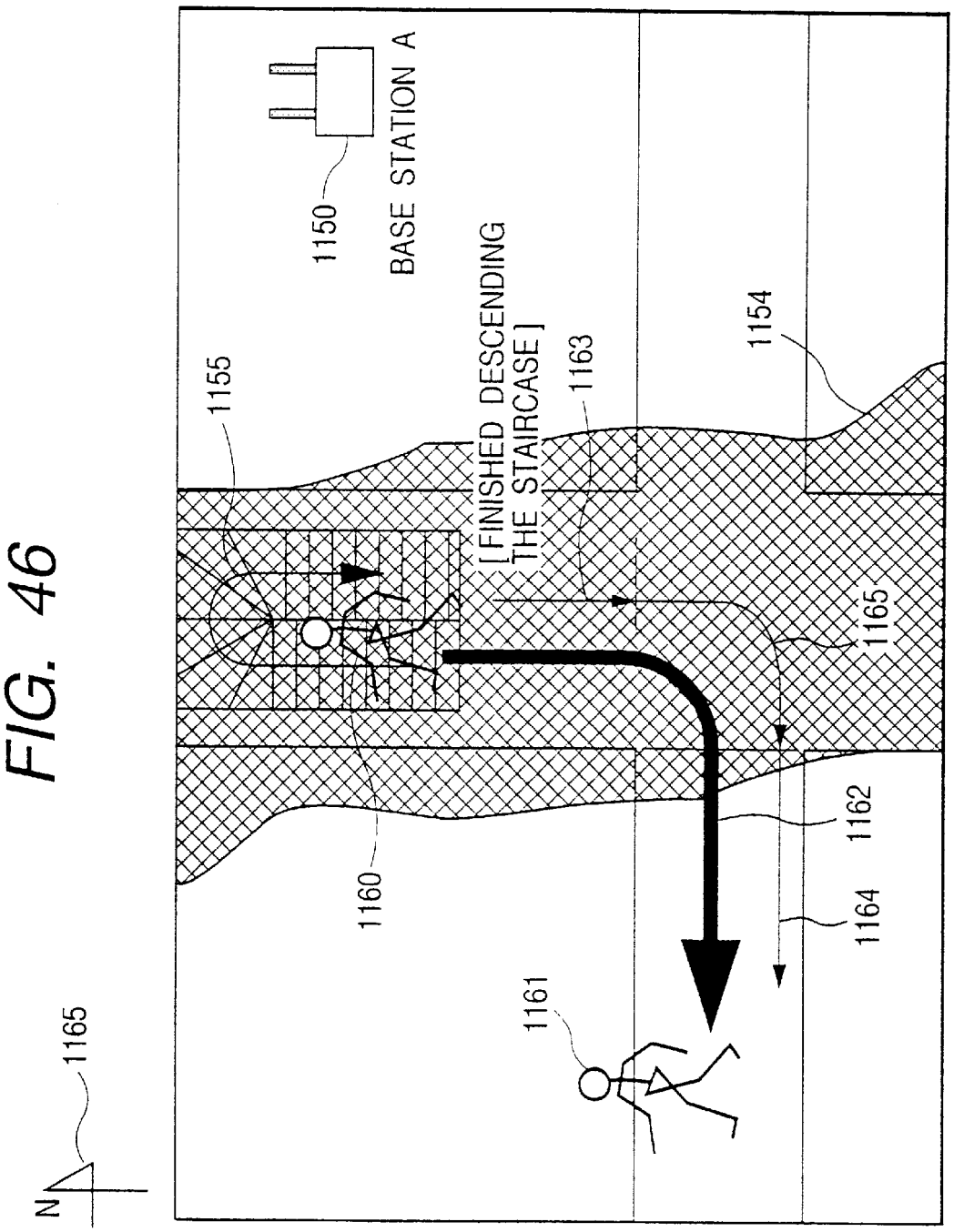
FIG. 46 is a diagram used for explaining a method for correcting a position identified by using results of recognizing a motion, an action and/or work output by a motion/action/work recognizing apparatus as a reference for consideration.

FIG. 46 is a diagram showing in detail how the position of an object under observation can be identified from information on a point of time the object finishes the ascending of the staircase and a period of time during which the object is walking. FIG. 46 is a diagram used for explaining a method for correcting a position identified by using results of recognizing a motion, an action and/or work output by the motion/action/work recognizing apparatus 1100 as a reference for consideration. Reference numeral 1165 is a orientation along which the object under observation is walking. In the example shown in this figure, the position of an object under observation is identified by using: an apparatus for determining a rough absolute position of the object by using an electric wave transmitted by a base station A 1150 of a cellular system; an apparatus for determining a relative position by using the number of walking steps output by an instrument attached to the object for counting the number of walking steps and information output by an instrument also attached to the object for monitoring changes in orientation and changes in onward-movement direction; and an apparatus for determining a position by using results of recognizing a motion, an action and/or work output by the motion/action/work recognizing apparatus 1100 described above with reference to FIG. 4.

As explained earlier, the measurement accuracy of a cellular system is not so high. As a result, even though the rough region satisfying the condition of the electric-field intensity, that is, a region in which the intensity of the electric fields is strong enough for reception, is identified, the absolute position of an object under observation can not be determined if the object is in motion. To solve this problem, a means for determining a relative position is resorted to. The apparatus for determining a relative position is used for calculating a moving distance of an object under observation by computing the product of the number of walking steps output by the instrument attached to the object for counting the number of walking steps and an average step length of the object. The apparatus for determining a relative position of an object under observation is also used for identifying the moving direction of the object by using information output by an instrument for monitoring changes in orientation and changes in onward-movement direction which is typically implemented by a orientation sensor or a gyro attached to the object. By integrating moving distances in their respective moving directions, the relative present position of the object under observation can be determined. As a result, it is possible to keep track of the movement of the object under observation in an identified rough region satisfying the condition of the electric-field intensity, that is, a region in which the intensity of the electric fields is strong enough for reception. Specifically, by using an absolute position measured by the cellular system as a reference (or an initial position), the absolute position of an object under observation is found from a relative position output by the relative-position measuring apparatus as a result of integration which is computed by integrating moving distances in their respective moving directions as described above. As described above, however, the measurement accuracy of the absolute-value measuring apparatus which is used for determining the initial position of the object under observation is poor. As a result, an initial error will affect subsequently found values. Further, in the apparatus for measuring a relative position, sampling-interval errors, measurement errors and integration errors are also accumulated as well. In order to solve this problem, the apparatus for determining a position by using results of recognizing a motion, an action and/or work is used for compensating the absolute position for the errors.

In the case of the example shown in FIG. 46, assume that a result of recognition of the state of a motion, an action and/or work indicates that the object under observation finished the ascending of the staircase. In this case, the upper end 1160 of the staircase is identified as the position of the object. The upper end 1160 of the staircase has a precision much higher than the junction region 1154 obtained as a result of measurement output by the cellular system. Then, with the upper end 1160 used as an initial value of the absolute position, it is thus possible to keep track of the position of the object under observation by using the apparatus for measuring a relative position.

Assume that, according to the orientation sensor or the gyro attached to object under observation, the object is moving from the initial value 1160 of the absolute position in a direction toward to the south. In addition, according to the instrument attached to the object for calculating the number of walking steps, a distance along which the object has walked can be calculated. In this way, a walking locus 1163 of the object can be identified. Assume that the object is turning the moving direction to the west along a locus segment 1165. By the same token, the walking locus at the segment 1165 can be identified from information output by the orientation sensor or the gyro and a walking-step count produced by the instrument for counting the number of walking steps. Loci traced by the object thereafter can also be found in the same way, allowing the present position 1161 of the object to be identified.

It should be noted that while the present invention has been described with reference to an embodiment wherein a cellular system is used as a typical means for measuring an absolute position, the description is not intended to be construed in a limiting sense. Another system for measuring an absolute position such as the GPS can also be used as well.

In the embodiment described above, a distance is calculated as a product of the number of walking steps and the length of a standard walking step. It is worth noting, however, that a result of recognition of a motion, an action and/or work may indicate that an object under observation is in a motion state of a leisurely walk or running. In this case, instead of using the length of the standard walking step, the length of the actual walking step in the motion, action and/or work is computed from items of recognition, that is, states of motion, and the degrees of recognition likelihood obtained for the items of recognition. Likewise, the distance is then calculated as a product of the number of walking steps and the length of the actual walking step. In this way, the distance can be found with a high degree of accuracy in comparison with that computed by using the length of the standard walking step.

Also as described above, in the present embodiment, a moving distance is calculated as a product of the number of walking steps and the length of a standard walking step as described above. It should be noted that, as an alternative, a sensor can be used for detecting the speed or the acceleration of an object under observation in the onward-movement direction. In the case of a speed sensor, the moving distance is then calculated by integration of measured values of the speed. In the case of an acceleration sensor, on the other hand, the moving distance is calculated by double-integration of measured values of the acceleration.

Also as described above, in the present embodiment, a position found by the apparatus for measuring an absolute position in conjunction with the motion/action/work recognizing apparatus is used as an initial position of a walking locus. It should be noted, however, that if the object under observation is in such a motion and/or takes such an action during a measurement carried out by the relative-position measuring apparatus that the position of the object can be identified, a position to be used as a new initial position can also be newly identified on the basis of the motion, the action and/or the work with relevant geographical information or relevant information on the interior of the building used as a reference. In this way, sampling-interval errors, measurement errors and integration errors can be prevented from being accumulated in the apparatus for measuring a relative position. This technique is particularly effective for a measurement of a position outside the service area of the cellular system. In the case of a measurement of a position outside the service area, since the apparatus for measuring an absolute position can not be used, the position is identified by resorting only to the apparatus for measuring a relative position which has the problem of error accumulation described above. By using this technique, however, the identified position is corrected from time to time, allowing the problem of error accumulation to be solved.

Also as described above, the present embodiment provides a method for measuring a position by using a cellular system based on a plurality of base stations. As an alternative, the cellular system can also be used in conjunction with a GPS for finding a position by means of a satellite or another position measuring apparatus in order to improve the accuracy of the position.

In addition, in the drawing method, it is possible to place the object under observation in a screen at a position found by the apparatuses and the methods provided by the present embodiment and to draw a drawing range in synchronization with the position of the object which changes from time to time, accompanying the movement of the object.

Further, a navigation system for guiding an object under observation can be built according to the same principle by using information on the position of the object found by the apparatuses and the methods provided by the present embodiment as a feedback.

Finally, the present embodiment exhibits an effect that a position obtained as a result of measurement by using the conventional position measuring apparatus can be compensated for errors to give a further improved accuracy.

What is claimed is:

1. A recognition system for recognizing motion and/or actions of an object under observation, said recognition apparatus comprising:

measurement means attached to said object under observation in order to measure a status change entailing the motions and/or actions of said object under observation;

characteristic quantity extraction means for extracting characteristic quantities from the measurements taken by said measurement means;

recognition means for recognizing the motions and/or actions of said object under observation in accordance with the characteristic quantities extracted from said measurements;

output means for outputting a recognized result; and wherein said characteristic quantity extraction means extracts said characteristic quantities by subjecting said measurements to time-frequency analysis.

2. A recognition system according to claim 1, wherein said time-frequency conversion is based on either Fourier transformation or wavelet transformation.

3. A recognition system according to claim 1, further comprising:

motion time measurement means for obtaining from said measurements a motion time representing a temporal characteristic of said motions and/or actions; and normalization means for normalizing said measurements on a time base provided by the acquired motion time;

wherein said characteristic quantity extraction means extracts said characteristic quantities by subjecting the normalized measurements to said time-frequency conversion.

4. A recognition system according to claim 1, further comprising:

motion time measurement means for obtaining from said measurements a motion time representing a temporal characteristic of said motions and/or actions; and characteristic quantity correction means for using said motion time to correct the characteristic quantities extracted by said characteristic quantity extraction means, thereby acquiring the corrected quantities as new characteristic quantities;

wherein said recognition means recognizes the motions and/or actions of said object under observation in accordance with the corrected characteristic quantities and with said stored characteristic quantities.

5. A recognition system according to claim 3, wherein said output means outputs not only the recognized result but also said motion time measured in connection with the recognized motions and actions.

6. A recognition system according to claim 1, further comprising expansion and contraction means for expanding and contracting said measurements on a time base;

wherein said characteristic quantity extraction means extracts said characteristic quantities from the measurements expanded and contracted by said expansion and contraction means.

7. A recognition system according to claim 1, further comprising expansion and contraction means for expanding and contracting said measurements on a measuring intensity base;

wherein said characteristic quantity extraction means extracts said characteristic quantities from the measurements expanded and contracted by said expansion and contraction means.

8. A recognition system according to claim 6, wherein said output means outputs a value representing an expansion-contraction ratio used by said expansion and contraction means in the processing thereof.

9. A recognition system for recognizing motions and/or actions of an object under observation, said recognition apparatus comprising:

measurement means attached to said object under observation in order to measure a status change entailing the motions and/or actions of said object under observation;

characteristic quantity extraction means for extracting characteristic quantities from the measurements taken by said measurement means;

recognition means for recognizing the motions and/or actions of said object under observation in accordance with the characteristic quantities extracted from said measurements, output means for outputting a recognized result;

further comprising characteristic quantity composition means for selecting a plurality of quantities from among the characteristic quantities stored in said storage means so as to compose the selected characteristic quantities into a new characteristic quantity;

wherein said recognition means recognizes, given the newly composed characteristic quantity and the characteristic quantities corresponding to said measurements, the motions and/or actions of said object under observation as those composed of a plurality of motions and/or actions corresponding to the selected characteristic quantities.

10. A recognition system according to claim 9, wherein said characteristic quantity composition means weights each of said selected characteristic quantities when composing them.

11. A recognition system for recognizing motions and/or actions of an object under observation, said recognition apparatus comprising:

measurement means attached to said object under observation in order to measure a status change entailing the motions and/or actions of said object under observation;

characteristic quantity extraction means for extracting characteristic quantities from the measurements taken by said measurement means;

recognition means for recognizing the motions and/or actions of said object under observation in accordance with the characteristic quantities extracted from said measurements;

output means for outputting a recognized result; and wherein, upon recognizing said motions and/or actions, said recognition means obtains correlations between the characteristic quantities corresponding to said measurements on the one hand, and the characteristic quantities stored in said storage means on the other hand, so that said recognition means recognizes said motions and/or actions in accordance with levels of the correlations thus obtained.

12. A recognition system for recognizing motions and/or actions of an object under observation, said recognition apparatus comprising:

measurement means attached to said object under observation in order to measure a status change entailing the motions and/or actions of said object under observation;

characteristic quantity extraction means for extracting characteristic quantities from the measurements taken by said measurement means;

recognition means for recognizing the motions and/or actions of said object under observation in accordance with the characteristic quantities extracted from said measurements;

output means for outputting a recognized result; and further comprising position measurement means for measuring positions of said object under observation.

13. A recognition system for monitoring motions and/or actions of an object under observation, said recognition system comprising a monitored-side device and a monitoring-side device;

wherein said monitored-side device includes a recognition unit for recognizing motions and/or actions of said object under observation, a storage unit for storing reference data about specific motions and/or actions to be reported, a judgment unit for judging whether any motions and/or actions of said object under observation need to be reported in accordance with the recognized motions and/or actions and with said reference data, and a report transmission unit for transmitting a report reflecting a judged result; and wherein said monitoring-side device includes a reception unit for receiving the report transmitted from said report transmission unit, and an output unit for effecting an output representing the received report.

14. A recognition system according to claim 13, wherein said monitored-side device further includes a history storage unit for storing a history of the recognized motions and/or actions;

wherein said storage unit stores predetermined reference data about specific action patterns to be reported, each of said patterns being composed of specific motions and/or actions; and wherein said judgment unit judges whether any pattern of combined motions and/or actions of said object under observation should be reported in accordance with the history stored in said history storage unit as well as with said reference data.

15. A recognition apparatus for recognizing gestures of an object under observation, said recognition apparatus comprising:

first storage means for storing reference data determined in advance about gestures to be recognized;

recognition means for recognizing a gesture corresponding to the motion of said object under observation on the basis of said reference data;

second storage means for storing in advance corresponding relations between said gestures to be recognized and meanings thereof;

meaning isolation means for isolating the meaning of any recognized gesture in accordance with the stored corresponding relations; and output means for outputting the isolated meaning of the recognized gesture.

16. An apparatus for displaying recognized motions and/or actions of an object under observation, said apparatus comprising:

measurement means attached to said object under observation in order to measure a status change entailing the motions and/or actions of said object under observation;

characteristic quantity extraction means for extracting characteristic quantities from the measurements taken by said measurement means;

motion generating means for generating a motion of animated object of said object under observation in accordance with the characteristic quantities extracted from said measurements; and display means for displaying said motion of animated object.

17. A recognition system according to claim 1, wherein the recognition means recognizes whether an object under observation is in a motion state of walking or running.

18. A recognition system according to claim 3, wherein the recognition means recognizes whether an object under observation is in a motion state of walking or running.

19. A recognition system according to claim 13, wherein the recognition means recognizes whether an object under observation is in a motion state of walking or running.

20. A recognition system according to claim 15, wherein the recognition means recognizes whether an object under observation is in a motion state of walking or running.

21. A recognition system according to claim 16, wherein the recognition means recognizes whether an object under observation is in a motion state of walking or running.

22. An apparatus for measuring a moving distance of an object under observation comprising:

measurement means attached to said object under observation in order to measure a status change in said object's position;

recognition means for recognizing the motions and/or actions of said object under observation; and calculation means for calculating the moving distance of an object by computing a product of a number of walking steps output by the measurement means and an average step length of said object.

23. A recognition apparatus according to claim 22, wherein the recognition means is capable of recognizing the moving up or moving down of an object and is further capable of map-matching the motion to stairs by recognizing such motion.

24. A recognition method for recognizing motions and/or actions of an object under observation, said recognition method comprising the steps of:

measuring a status change entailing the motions and/or actions of an object under observation;

extracting characteristic quantities from the measurements of status change;

recognizing the motions and/or actions of said object under observation in accordance with the characteristic quantities extracted; and outputting a recognized result, wherein said characteristic quantities are extracted by subjecting said measurements to time-frequency analysis.

25. A recognition method according to claim 24, wherein said time-frequency conversion is based on either Fourier transformation or wavelet transformation.

26. A recognition method according to claim 24, further comprising the steps of:

obtaining from said measurements a motion time representing a temporal characteristic of said motions and/or actions; and normalizing said measurements on a time base provided by the acquired motion time, said characteristic quantities are extracted by subjecting the normalized measurements to said time-frequency conversion.

27. A recognition method according to claim 24, further comprising the steps of:

obtaining from said measurements a motion time representing a temporal characteristic of said motions and/or actions; and using said motion time to correct the characteristic quantities extracted, thereby acquiring the corrected quantities as new characteristic quantities, wherein the motions and/or actions of said object under observation are recognized in accordance with the corrected characteristic quantities and with said stored characteristic quantities.

28. A recognition method according to claim 24, further comprising the step of expanding and contracting said measurements on a time base, wherein said characteristic quantities extracted from the measurements are expanded and contracted.

29. A recognition method according to claim 24, further comprising the step of expanding and contracting said measurements on a measuring intensity base;

wherein said characteristic quantities extracted from the measurements are expanded and contracted.

* * * * *